United States Patent [19]

Shinjo et al.

[11] Patent Number: 5,292,453

[45] Date of Patent: Mar. 8, 1994

[54] FERROELECTRIC LIQUID CRYSTAL COMPOSITION WITH IMPROVED DRIVING VOLTAGE AND TEMPERATURE MARGINS AND LIQUID CRYSTAL DEVICE USING SAME

[75] Inventors: Kenji Shinjo, Atsugi; Takao Takiguchi, Tokyo; Hiroyuki Kitayama, Sagamihara; Kazuharu Katagiri, Tama; Masataka Yamashita, Hiratsuka; Masahiro Terada, Atsugi; Takeshi Togano, Yokohama; Yoshiko Kimura, Hiratsuka; Masanobu Asaoka, Yokohama; Junko Sato, Hiratsuka, all of Japan

[73] Assignee: Canon Kabushiki Kaisha, Tokyo, Japan

[21] Appl. No.: 48,071

[22] Filed: Apr. 19, 1993

Related U.S. Application Data

[63] Continuation of Ser. No. 944,030, Sep. 11, 1992, abandoned, which is a continuation of Ser. No. 370,724, Jun. 23, 1989, abandoned.

[30] Foreign Application Priority Data

| Jun. 24, 1988 [JP] | Japan | 63-157675 |
| Jul. 29, 1988 [JP] | Japan | 63-188110 |
| Jul. 29, 1988 [JP] | Japan | 63-188112 |
| Jun. 9, 1989 [JP] | Japan | 1-147990 |

[51] Int. Cl.$^5$ ............... C09K 19/34; C09K 19/30; C09K 19/20; G02F 1/13
[52] U.S. Cl. ............... 252/299.61; 252/299.63; 252/299.67; 359/103
[58] Field of Search ......... 252/299.61, 299.63, 252/299.67; 359/103

[56] References Cited

U.S. PATENT DOCUMENTS

| 4,279,770 | 7/1981 | Inukai et al. | 252/299.62 |
| 4,479,885 | 10/1984 | Mukoh et al. | 252/299.62 |
| 4,542,230 | 9/1985 | Gray et al. | 560/1 |
| 4,798,680 | 1/1989 | Nohira et al. | 252/299.01 |
| 4,834,904 | 5/1989 | Krouse et al. | 252/299.01 |
| 4,911,863 | 3/1990 | Sage et al. | 252/299.65 |
| 4,917,821 | 4/1990 | Mori et al. | 252/299.63 |

FOREIGN PATENT DOCUMENTS

| 0178647 | 4/1986 | European Pat. Off. |
| 0237007 | 9/1987 | European Pat. Off. |
| 0255962 | 2/1988 | European Pat. Off. |
| 0267585 | 5/1988 | European Pat. Off. |
| 0293910 | 12/1988 | European Pat. Off. |
| 0315958 | 5/1989 | European Pat. Off. |

*Primary Examiner*—Robert L. Stoll
*Assistant Examiner*—C. Harris
*Attorney, Agent, or Firm*—Fitzpatrick, Cella, Harper & Scinto

[57] ABSTRACT

A ferroelectric chiral smectic liquid crystal composition, comprising: at least one optically active compound represented by the following formula (II):

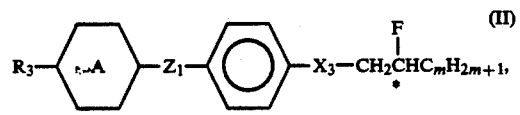

wherein $R_3$ denotes a linear or branched alkyl group having 1-18 carbon atoms capable of having a substituent; $X_3$ denotes a single bond,

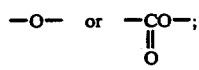

$Z_1$ denotes a single bond or (Abstract continued on next page.)

-continued

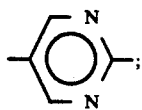

and m is 1-12; at least one compound represented by the following formula (III):

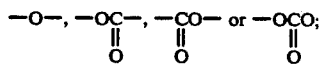  (III)

wherein $R_4$ and $R_5$ respectively denote a linear or branched alkyl group having 1-18 carbon atoms capable of having a substituent, at lease one of $R_4$ and $R_5$ being optically active; $X_4$ denotes a single bond,

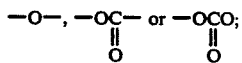

and $X_5$ denotes a single bond,

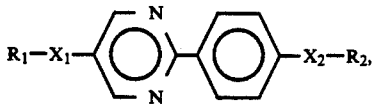

and at least one compound represented by the following formula (I) or (IV):

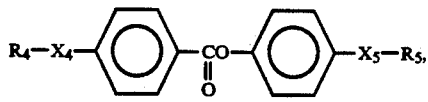  (I)

wherein $R_1$ and $R_2$ respectively denote a linear or branched alkyl group having 1-18 carbon atoms capable of having a substituent of $C_1$-$C_{12}$ alkoxy group; $X_1$ and $X_2$ respectively denote a single bond, point and non-selected

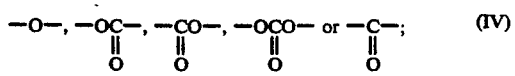  (IV)

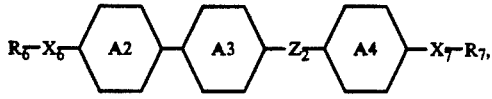

wherein $R_6$ and $R_7$ respectively denote a linear or branched alkyl group having 1-18 carbon atoms capable of having a substituent; $X_6$ and $X_7$ respectively denote a single bond,

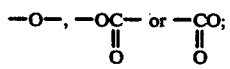

$Z_2$ denotes

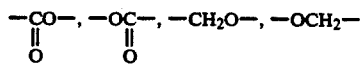

or a single bond;

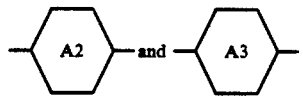

respectively denote

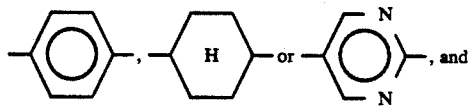, and

(Abstract continued on next page.)

denotes
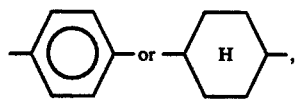
with the proviso that at least one of
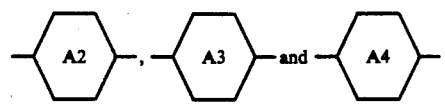
is
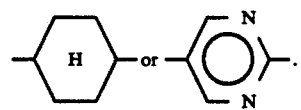
7 Claims, 3 Drawing Sheets

FERROELECTRIC LIQUID CRYSTAL COMPOSITION WITH IMPROVED DRIVING VOLTAGE AND TEMPERATURE MARGINS AND LIQUID CRYSTAL DEVICE USING SAME

This application is a continuation of application Ser. No. 944,030, filed Sep. 11, 1992, now abandoned, which is a continuation of application Ser. No. 370,724, filed Jun. 23, 1989, now abandoned.

FIELD OF THE INVENTION AND RELATED ART

The present invention relates to a liquid crystal composition used in a liquid crystal display device, a liquid crystal-optical shutter, etc., more particularly to a novel liquid crystal composition with improved responsiveness to an electric field and a liquid crystal device using the liquid crystal composition.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127-128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected or regions where a scanning electrode is not selected and a signal electrode is selected (which regions are so called "half-selected points"). If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected points when scanning is repeatedly effected. As a result, this leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, it is the present state that the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216, U.S. Pat. No. 4367924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, ferroelectric liquid crystal materials developed heretofore cannot be said to satisfy sufficient characteristics required for a liquid crystal device including low-temperature operation characteristic, high-speed responsiveness, etc. A high response speed can be obtained by (a) increasing the spontaneous polarization, (b) lowering the viscosity $\eta$, or (c) increasing the applied voltage. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Further, if it is assumed that the operation temperature of an actual display is 5°–40° C., the response speed changes by a factor of about 20, so that it actually exceeds the range controllable by driving voltage and frequency.

As described hereinabove, commercialization of a ferroelectric liquid crystal device requires a ferroelectric chiral smectic liquid crystal composition having a low viscosity, a high-speed responsiveness and a small temperature-dependence of response speed.

In a representative FLC cell structure, a pair of substrates are disposed, each substrate of e.g. glass being provided with an electrode pattern of e.g. ITO, further thereon with a layer of e.g. $SiO_2$ (about 1000 Å) for preventing short circuit between the pair of substrates and further thereon with a film of e.g. polyimide (PI; such as SP-510, 710, ... available from Toray K. K.) of about 500 Å in thickness, which is then treated for alignment control by rubbing with e.g. an acetate fiber-planted cloth. Such a pair of substrates are disposed opposite to each other so that their alignment control directions are symmetrical and the spacing between the substrates is held at 1–3 microns.

On the other hand, it is known that the ferroelectric liquid crystal molecules under such non-helical conditions are disposed in succession so that their directors (longer molecular axes) are gradually twisted between the substrates and do not show a uniaxial orientation or alignment (i.e., in a splay alignment state). A problem in this case is a low transmittance through the liquid crystal layer.

Transmitted light intensity I through a liquid crystal is given by the following equation with respect to the incident light intensity $I_0$ under cross nicols when the uniaxial alignment of the molecules is assumed:

$$I = I_0 \sin^2(4\theta a)\sin^2(\pi \Delta nd/\lambda) \qquad (1)$$

wherein $\Delta n$ denotes the refractive index anisotropy of the FLC; d, the cell thickness; $\lambda$, the wavelength of the incident light; and $\theta a$, a half of the angle between two stable states (tilt angle).

When a conventional FLC cell is used, it has been experimentally known that $\theta a$ is 5–8 degrees under a twisted alignment condition. The control of physical properties affecting the term $\Delta nd\pi/\lambda$ cannot be easily performed, so that it is desired to increase $\theta a$ to increase I. However, this has not been successfully accomplished by only a static alignment technique.

With respect to such a problem, it has been proposed to utilize a torque relating to a dielectric anisotropy $\Delta \epsilon$ of an FLC (1983 SID report from AT & T; Japanese Laid-Open Patent Applns. 245142/1986, 246722/1986, 246723/1986, 246724/1986, 249024/1986 and 249025/1986). More specifically, a liquid crystal molecule having a negative $\Delta \epsilon$ tends to become parallel to the substrates under application of an electric field. By utilizing this property, if an effective value of AC electric field is applied even in a period other than switching, the above-mentioned twisted alignment is removed, so that $\theta a$ is increased to provide an increased transmittance (AC stabilization effect). A torque $\Gamma P_S$ acting on FLC molecules involved in switching of states and a torque $\Gamma \Delta \epsilon$ acting on FLC molecules relating to the AC stabilization effect are respectively proportional to physical properties as shown in the following formulas:

$$\Gamma P_S \propto P_S \cdot E \qquad (2)$$

$$\Gamma \Delta \epsilon \propto \tfrac{1}{2}\Delta\epsilon \cdot \epsilon_0 \cdot E^2 \qquad (3)$$

The above formula (3) apparently shows that the sign and absolute value of $\Delta \epsilon$ of the FLC play an important role.

FIG. 4 attached hereto shows the change of $\theta a$ versus Vrms experimentally measured for 4 FLCs having different values of $\Delta \epsilon$. The measurement was conducted under application of AC rectangular pulses of 60 KHz so as to remove the influence of $P_S$. The curves (I)–(IV) correspond to the results obtained by using FLCs showing the following $\Delta \epsilon$ values
(I) $\Delta \epsilon \neq -5.5$, (II) $\Delta \epsilon \neq -3.0$,
(III) $\Delta \epsilon \neq -0$, (IV) $\Delta \epsilon \neq 1.0$.

As is clear from the graph in FIG. 8, a larger negative value of $\Delta \epsilon$ provides a large $\theta a$ at a lower voltage and thus contributes to provision of an increased I.

The transmittances obtained by using the liquid crystals (I) and (III) were 15% for (I) and 6% for (III) (under application of rectangular AC waveforms of 60 kHz and ±8 V), thus showing a clear difference.

As is known from the above examples, the display characteristics of an SSFLC (Surface-Stabilized FLC) can be remarkably changed by controlling the properties relating to $\Delta \epsilon$ and $P_S$.

In order to provide a ferroelectric liquid crystal composition having a negatively large $\Delta \epsilon$, it is most effective to include a compound having a negative $\Delta \epsilon$ with a large absolute value. For example, it is possible to obtain a compound having a negatively large $\Delta \epsilon$ by introducing a halogen or cyano group in a shorter axis direction of a molecule or by introducing a heterocyclic skeleton in a molecule.

The magnitude of $\Delta \epsilon$ of a compound having a negative $\Delta \epsilon$ substantially varies depending on the structure thereof. Some examples of such compounds are shown below:

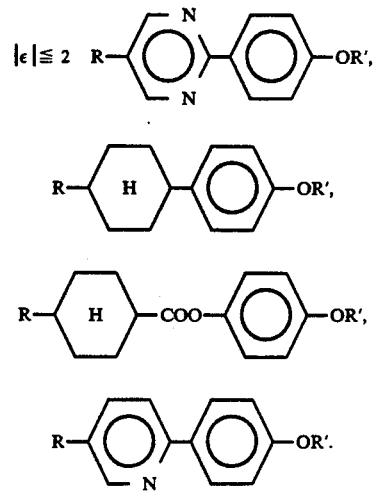

-continued $2 < |\epsilon| \leq 5$ 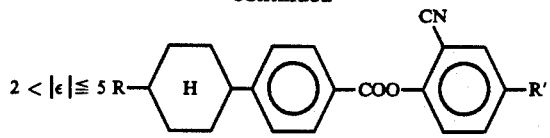

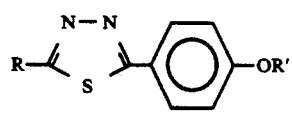

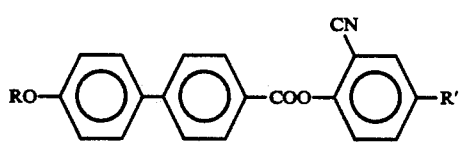

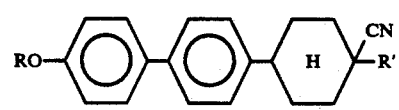

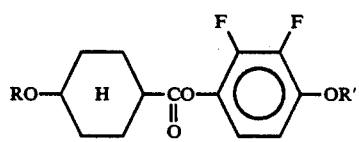

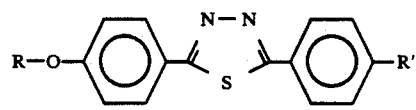

$5 < |\epsilon| \leq 10$ 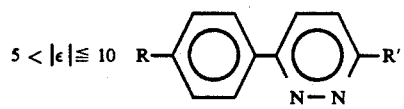

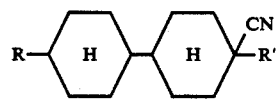

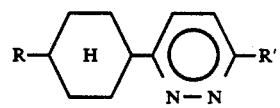

$|\epsilon| > 10$ 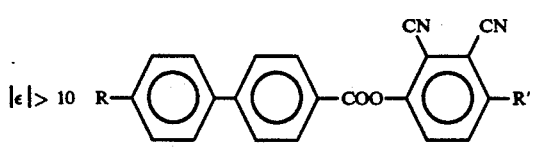

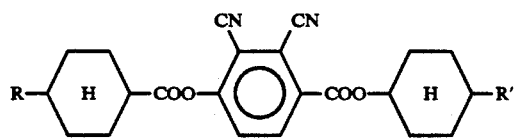

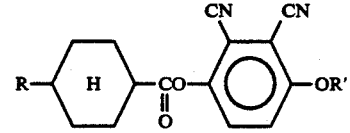

Herein, R and R' respectively denote an alkyl group. These may be classified roughly into three groups including compounds having a negatively small $\Delta\epsilon$ ($|\Delta\epsilon| \leq 2$), compounds having a negative medium $\Delta\epsilon$ ($2 < |\Delta\epsilon| 10$) and compounds having a negatively large $\Delta\epsilon$ ($|\Delta\epsilon| > 10$). Among these, compounds having a $|\Delta\epsilon|$ of $\leq 2$ have little effect of increasing $|\Delta\epsilon|$. Compounds having a $|\Delta\epsilon|$ of $>10$ are very effective in increasing $|\Delta\epsilon|$ but those available heretofore are only dicyanohydroquinone derivatives.

However, a dicyanohydroquinone derivative, while it has a large $|\Delta\epsilon|$-increasing effect, has a high viscosity, so that it is liable to degrade a switching characteristic when its content is increased. On the other hand, among the compounds having a medium $|\Delta\epsilon|$ ($2 < |\Delta\epsilon| \leq 10$), some compounds have a moderately low viscosity while their $|\Delta\epsilon|$-increasing effect is somewhat lower than those having a large $|\Delta\epsilon|$.

From the above consideration, it is essential to select a compound having a negative anisotropy, preferably one having a $|\Delta\epsilon|$ of $>2$, and mixing it with an appropriately selected other compound in a properly selected mixing ratio.

SUMMARY OF THE INVENTION

An object of the present invention is to provide a chiral smectic liquid crystal composition having a large response speed and a decrease temperature-dependence of the response speed adapted for providing a practical ferroelectric liquid crystal device.

Another object of the present invention is to provide a liquid crystal composition further containing a mesomorphic compound having a negative dielectric anisotropy to show an AC stabilization effect providing remarkably improved display characteristics.

A further object of the present invention is to provide a liquid crystal device using such a liquid crystal composition and showing improved driving and display characteristics.

According to the present invention, there is provided a ferroelectric chiral smectic liquid crystal composition, comprising:

at least one optically active compound represented by the following formula (II):

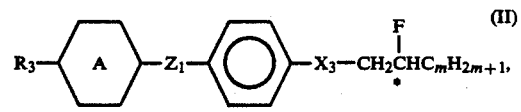

wherein $R_3$ denotes a linear or branched alkyl group having 1-18 carbon atoms capable of having a substituent; $X_3$ denotes a single bond, $$-O- \quad \text{or} \quad -\underset{\underset{O}{\|}}{C}O-;$$

$Z_1$ denotes a single bond or

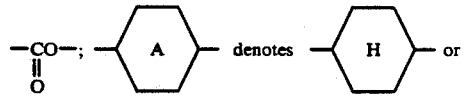

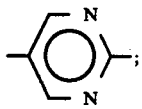

and m is 1-12;

at least one compound represented by the following formula (III):

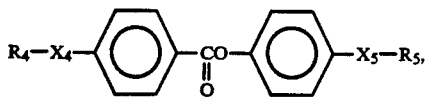

wherein $R_4$ and $R_5$ respectively denote a linear or branched alkyl group having 1-18 carbon atoms capable of having a substituent, at lease one of $R_4$ and $R_5$ being optically active; $X_4$ denotes a single bond,

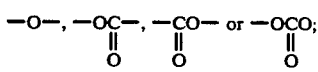

$X_5$ denotes a single bond,

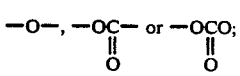

and at least one compound represented by the following formula (I) or (IV):

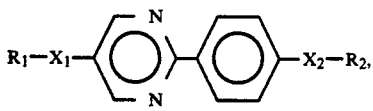

wherein $R_1$ and $R_2$ respectively denote a linear or branched alkyl group having 1-18 carbon atoms capable of having a substituent of $C_1$-$C_{12}$ alkoxy group; $X_1$ and $X_2$ respectively denote a single bond, —O—,

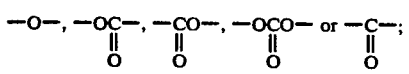

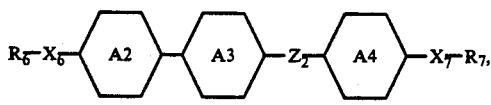

wherein $R_6$ and $R_7$ respectively denote a linear or branched alkyl group having 1-18 carbon atoms capable of having a substituent; $X_6$ and $X_7$ respectively denote a single bond,

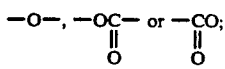

$Z_2$ denotes

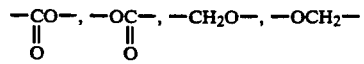

or a single bond

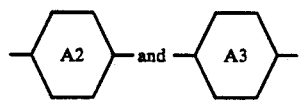

respectively denote

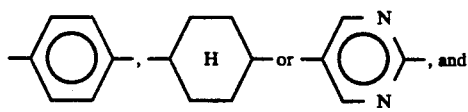

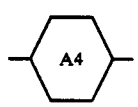

denotes

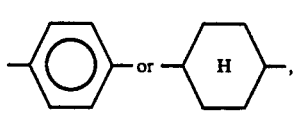

with proviso that at least one of

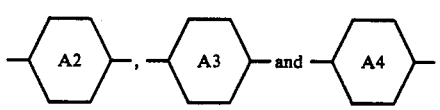

is

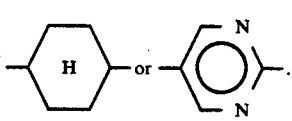

According to the present invention, there is further provided a ferroelectric liquid crystal composition as described above further comprising a mesomorphic compound having a negative dielectric anisotropy, which is preferably one having a $\Delta\epsilon < -2$, more preferably $\Delta\epsilon < -5$, most preferably $\Delta\epsilon < -10$.

The present invention further provides a liquid crystal device comprising a pair of substrates and such a ferroelectric liquid crystal composition as described above disposed between the electrode plates.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
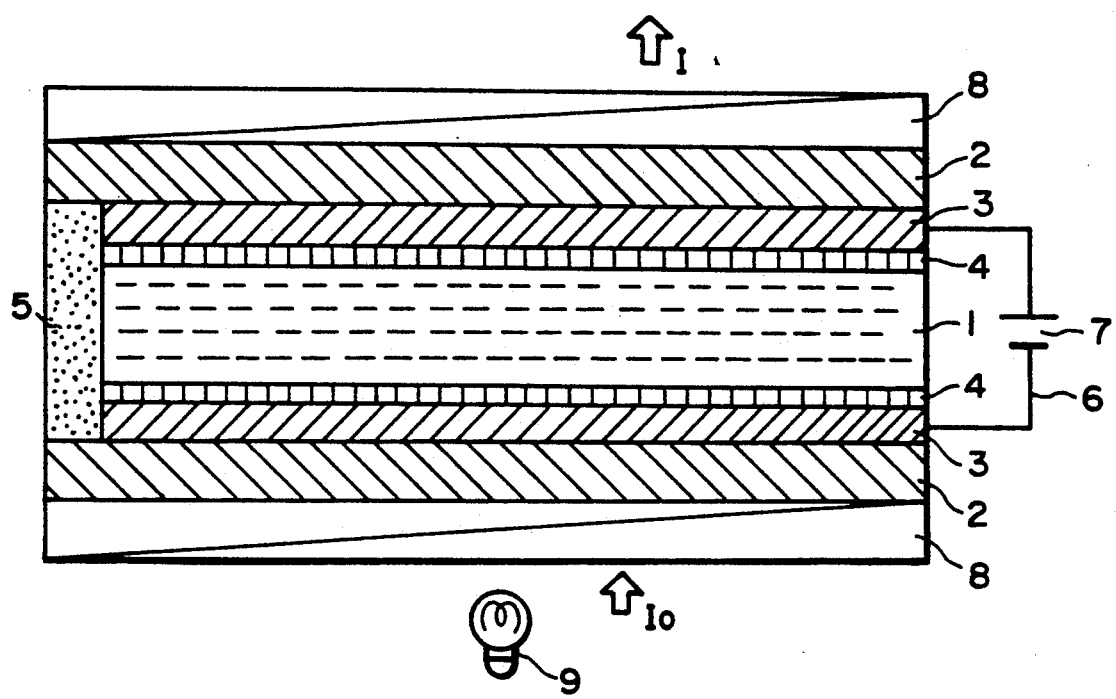
FIG. 1 is a schematic sectional view of a liquid crystal display device using a ferroelectric liquid crystal.

Preferred examples of the compounds represented by the above-mentioned general formula (I) may include those represented by the following formulas (I-a) to (I-p).

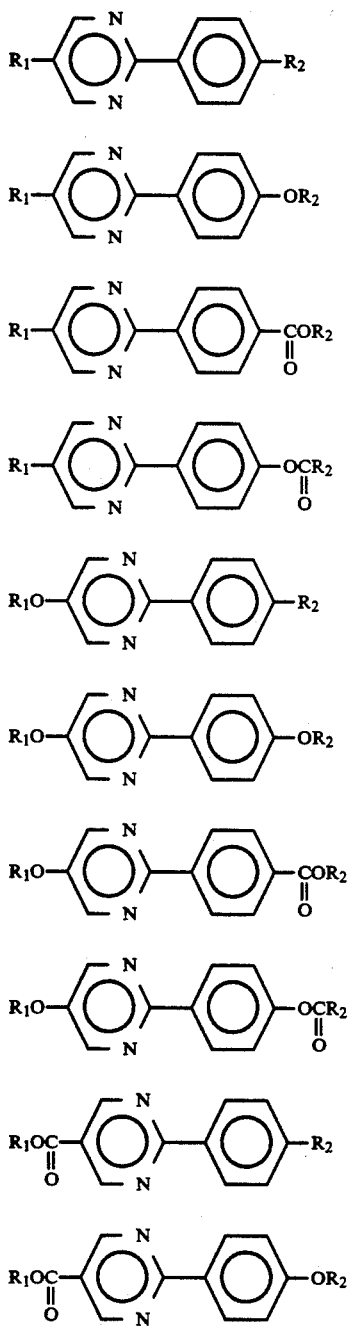
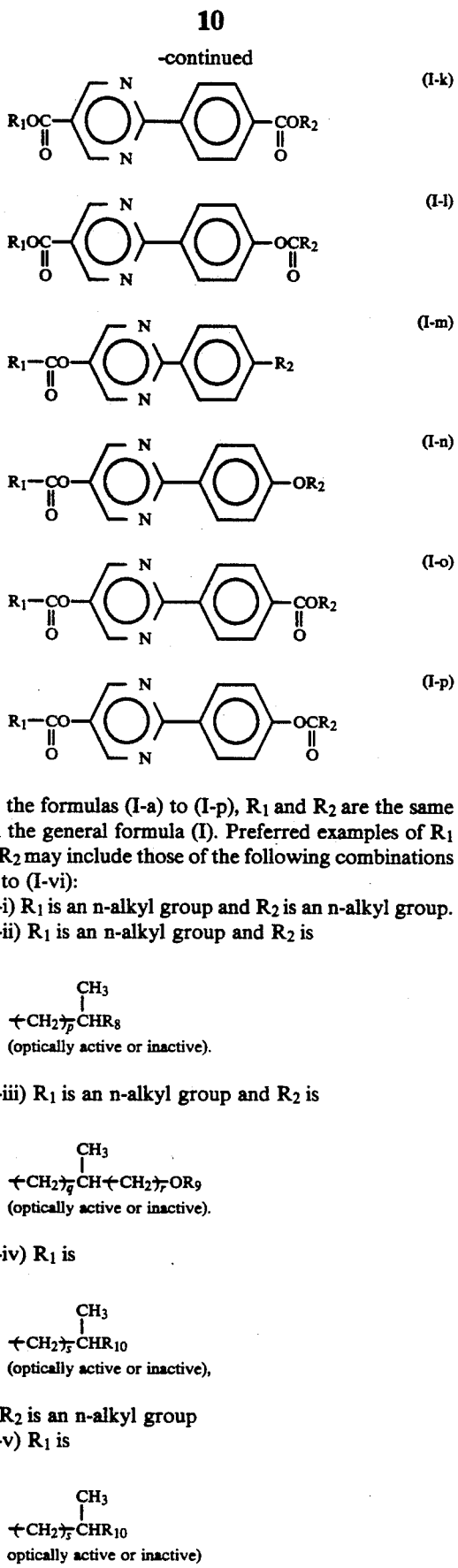

In the formulas (I-a) to (I-p), $R_1$ and $R_2$ are the same as in the general formula (I). Preferred examples of $R_1$ and $R_2$ may include those of the following combinations (I-i) to (I-vi):

(I-i) $R_1$ is an n-alkyl group and $R_2$ is an n-alkyl group.

(I-ii) $R_1$ is an n-alkyl group and $R_2$ is $$\mathrm{{+}CH_2{\mathord{\Rightarrow}_{\mathit{p}}}CHR_8}$$
$$\overset{|}{CH_3}$$

(optically active or inactive).

(I-iii) $R_1$ is an n-alkyl group and $R_2$ is $$\mathrm{{+}CH_2{\mathord{\Rightarrow}_{\mathit{q}}}CH{+}CH_2{\mathord{\Rightarrow}_{\mathit{r}}}OR_9}$$
$$\overset{|}{CH_3}$$

(optically active or inactive).

(I-iv) $R_1$ is $$\mathrm{{+}CH_2{\mathord{\Rightarrow}_{\mathit{s}}}CHR_{10}}$$
$$\overset{|}{CH_3}$$

(optically active or inactive), and $R_2$ is an n-alkyl group (I-v) $R_1$ is $$\mathrm{{+}CH_2{\mathord{\Rightarrow}_{\mathit{s}}}CHR_{10}}$$
$$\overset{|}{CH_3}$$

optically active or inactive)

and $R_2$ is

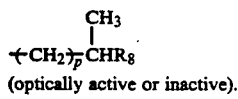
(optically active or inactive).

(I-vi) $R_1$ is

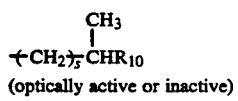
(optically active or inactive)

and $R_2$ is

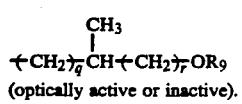
(optically active or inactive).

In the above formulas (I-i) to (I-vi), $R_8$, $R_9$ and $R_{10}$ respectively denote a linear or branched alkyl group; p, q and s are respectively 0–7; and r is 0 or 1.

Further, preferred examples of the compounds represented by the above-mentioned general formula (II) may include those represented by the following formulas (II-a) and (II-b).

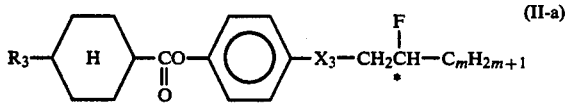
(II-a)

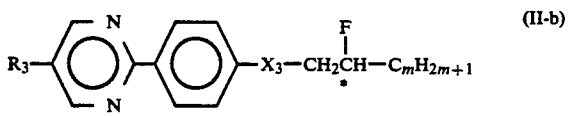
(II-b)

In the above-formulas (II-a) and (II-b), $R_1$, $X_1$ and m are the same as in the general formula (II).

Further, in the above-mentioned general formula (III), $X_4$ may preferably be

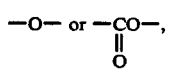

and $X_5$ may preferably be

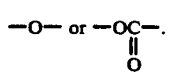

Preferred examples of $R_4$ and $R_5$ may include those of the following combinations (III-i) to (III-v).

(III-i) $R_4$ is an n-alkyl group and $R_5$ is

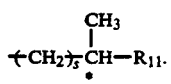

(III-ii) $R_4$ is

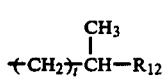

and $R_5$ is an n-alkyl group.

(III-iii) $R_4$ is

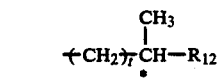

and $R_5$ is

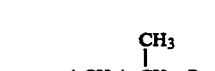

(III-iv) $R_4$ is an n-alkyl group and $R_5$ is

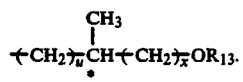

(III-v) $R_4$ is

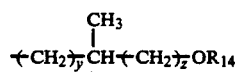

and $R_5$ is an n-alkyl group.

In the above combinations (III-i) to (III-v), $R_{11}$ to $R_{14}$ respectively denote a linear or branched alkyl group; s, t, u and y are respectively 0–7, and x and z are respectively 0 or 1.

Further, preferred examples of the compounds represented by the above-mentioned general formula (IV) may include those represented by the following formulas (IV-a) to (IV-q).

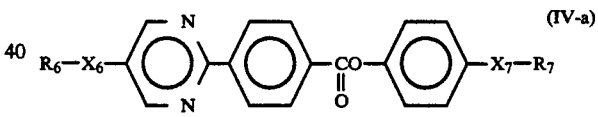
(IV-a)

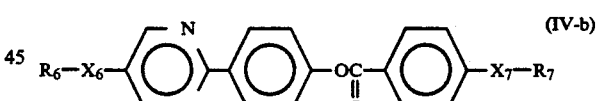
(IV-b)

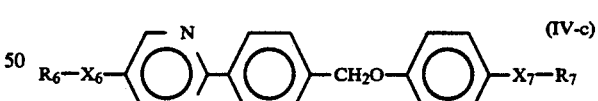
(IV-c)

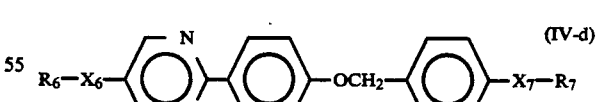
(IV-d)

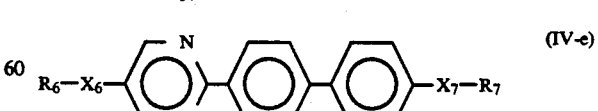
(IV-e)

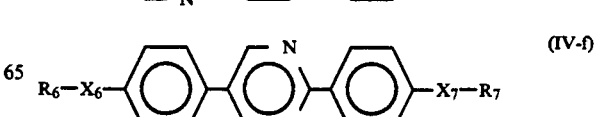
(IV-f)

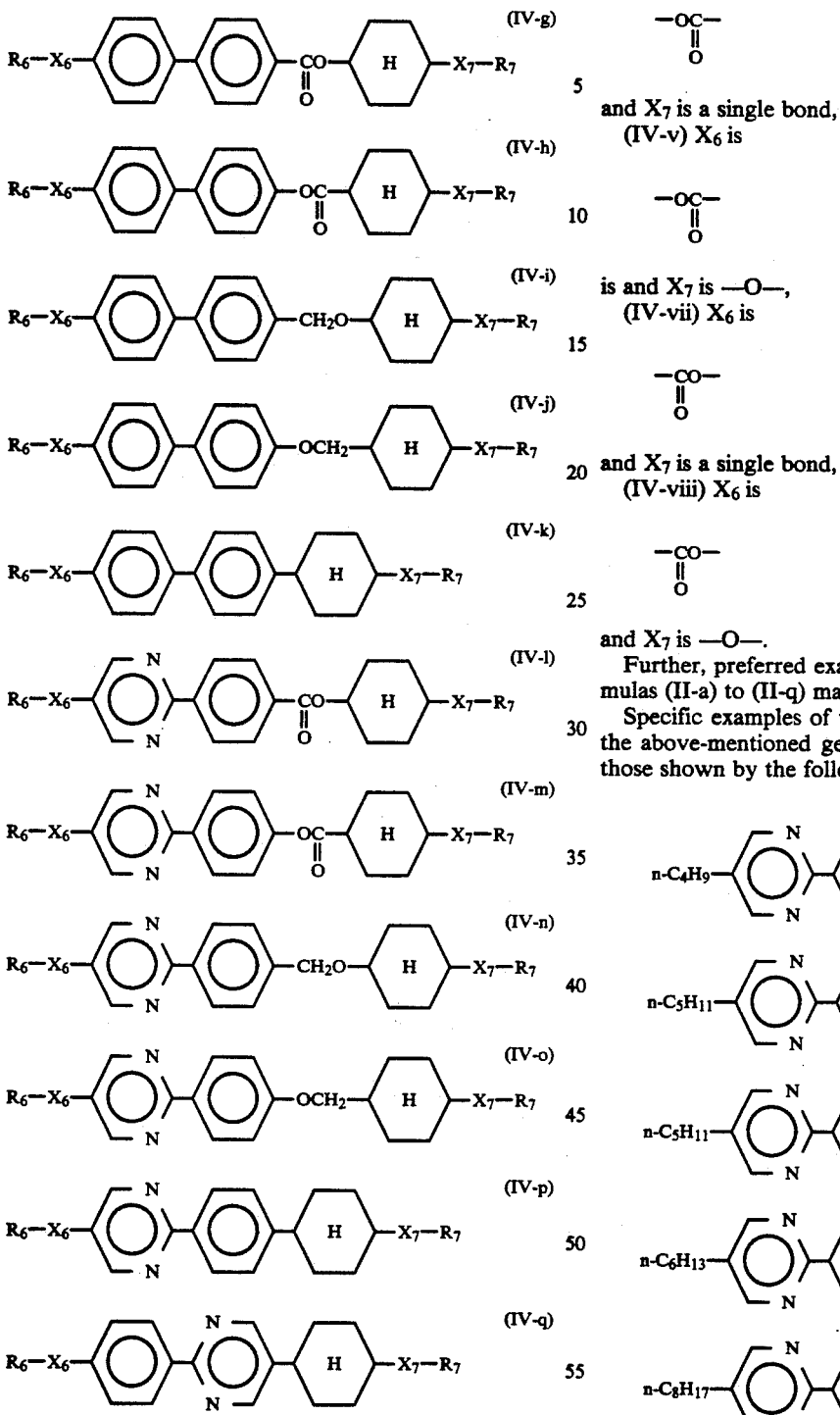

−OC−
‖
O and $X_7$ is a single bond,
(IV-v) $X_6$ is

is and $X_7$ is —O—,
(IV-vii) $X_6$ is

and $X_7$ is a single bond,
(IV-viii) $X_6$ is

and $X_7$ is —O—.

Further, preferred examples of $R_6$ and $R_7$ in the formulas (II-a) to (II-q) may include linear alkyl groups.

Specific examples of the compounds represented by the above-mentioned general formula (I) may include those shown by the following structural formulas.

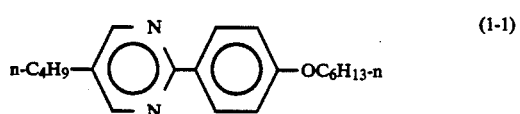 (1-1)

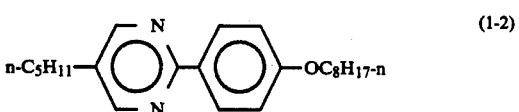 (1-2)

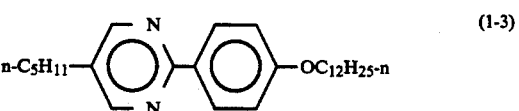 (1-3)

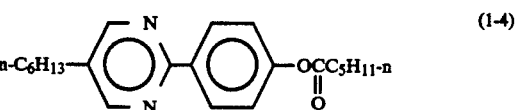 (1-4)

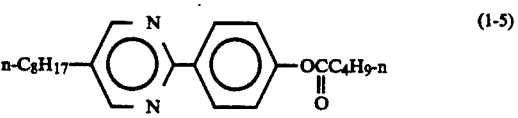 (1-5)

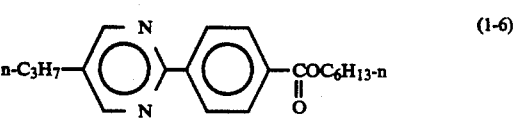 (1-6)

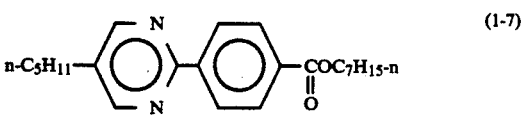 (1-7)

In the formulas (IV-a) to (IV-q), $R_6$, $R_7$, $X_6$ and $X_7$ are respectively the same as in the general formula (IV). Preferred examples of $X_6$ and $X_7$ may include the following combinations (IV-i) to (IV-viii):

(IV-i) $X_6$ is a single bond and $X_7$ is a single bond,
(IV-ii) $X_6$ is a single bond and $X_7$ is —O—,
(IV-iii) $X_6$ is —O— and $X_7$ is a single bond,
(IV-iv) $X_6$ is —O— and $X_7$ is —O—,
(IV-v) $X_6$ is

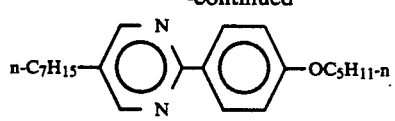 (1-8)
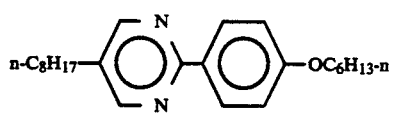 (1-9)
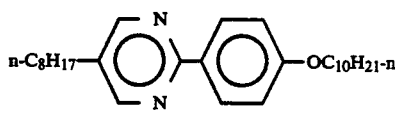 (1-10)
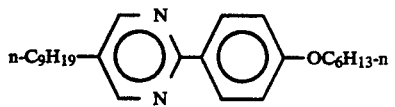 (1-11)
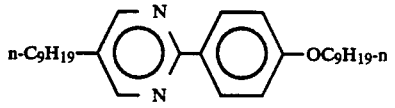 (1-12)
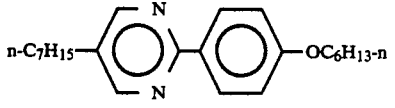 (1-13)
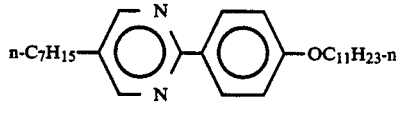 (1-14)
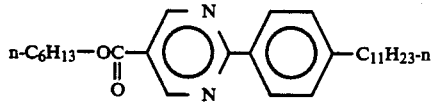 (1-15)
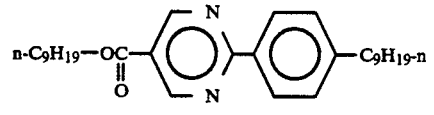 (1-16)
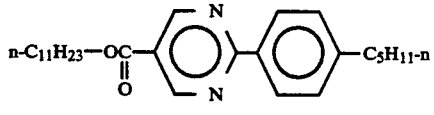 (1-17)
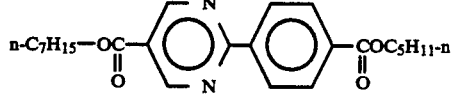 (1-18)
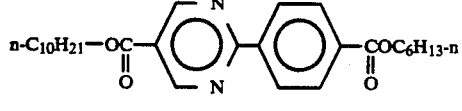 (1-19)
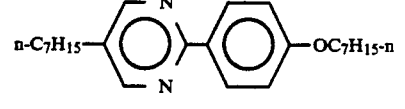 (1-20)
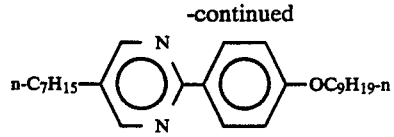 (1-21)
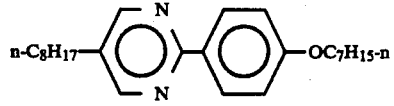 (1-22)
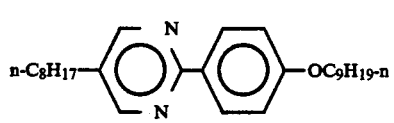 (1-23)
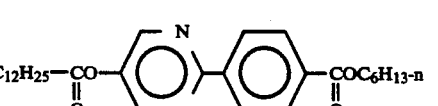 (1-24)
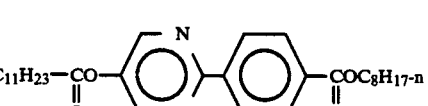 (1-25)
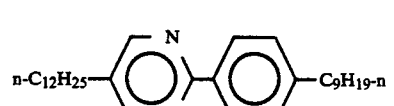 (1-26)
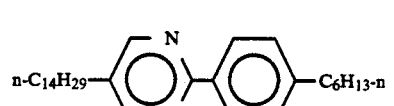 (1-27)
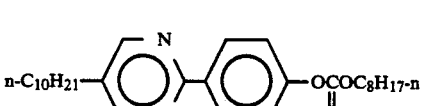 (1-28)
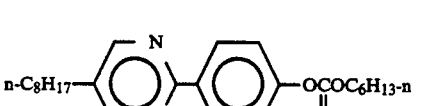 (1-29)
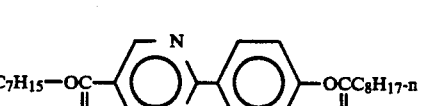 (1-30)
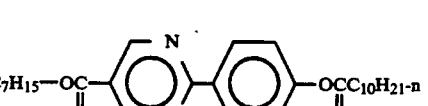 (1-31)
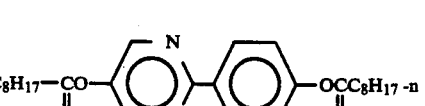 (1-32)
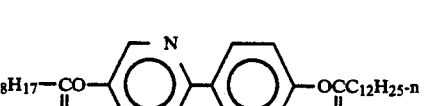 (1-33)

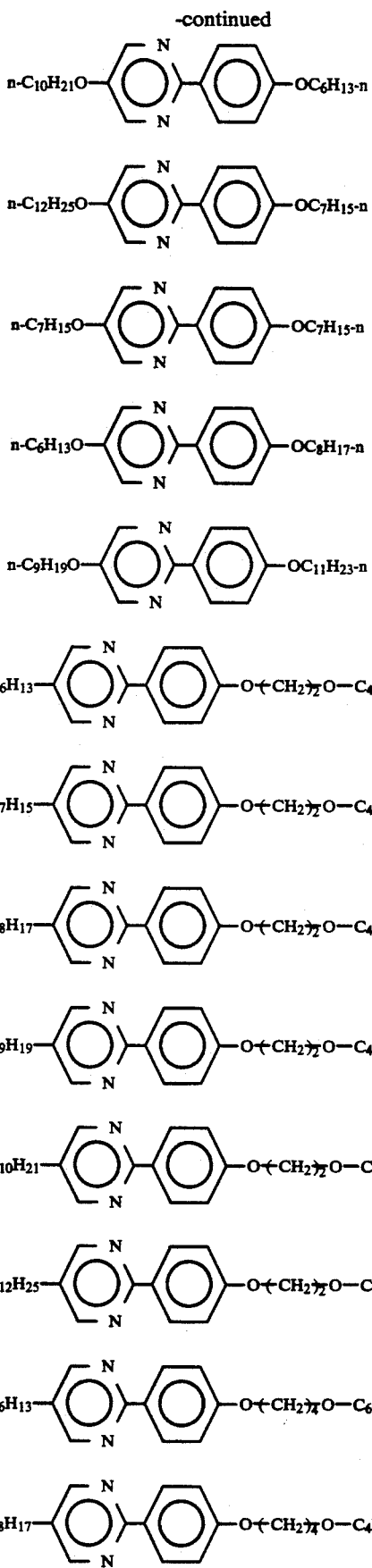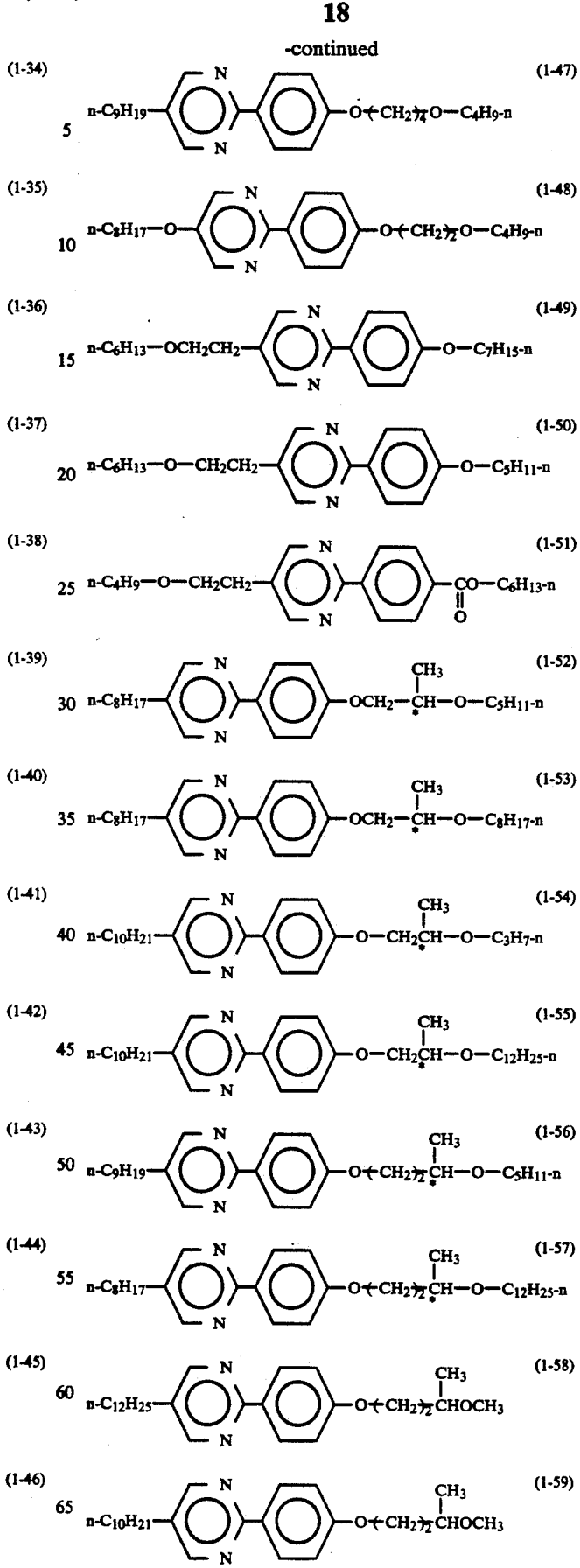

(Chemical structure table, compounds 1-60 through 1-85)

-continued
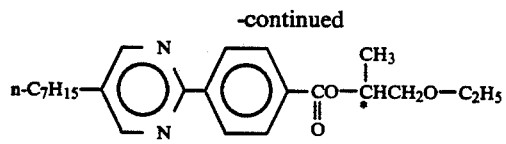 (1-86)
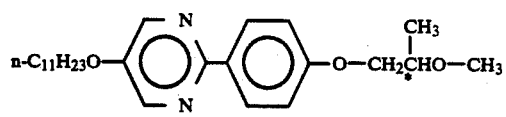 (1-87)
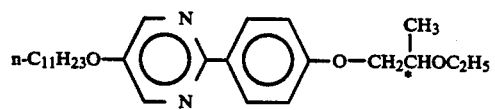 (1-88)
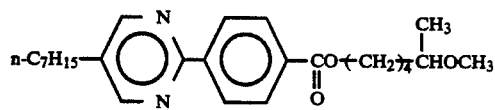 (1-89)
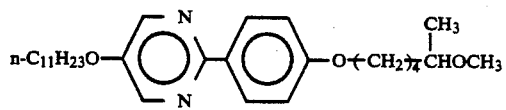 (1-90)
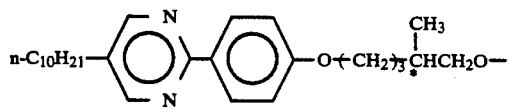 (1-91)
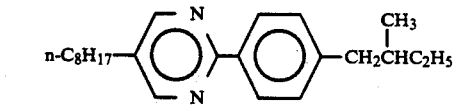 (1-92)
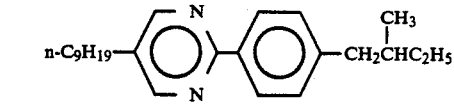 (1-93)
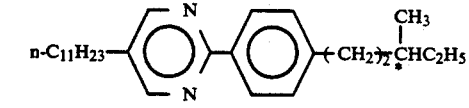 (1-94)
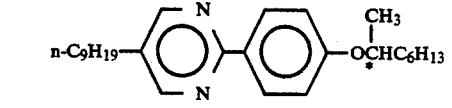 (1-95)
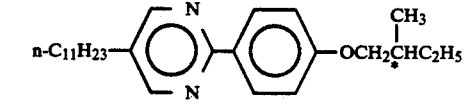 (1-96)
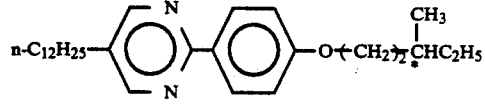 (1-97)
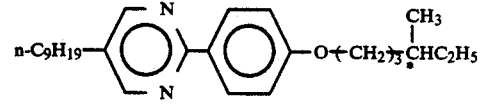 (1-98)
-continued
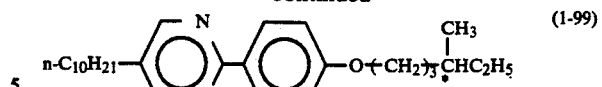 (1-99)
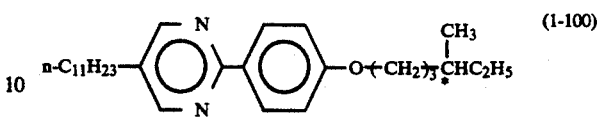 (1-100)
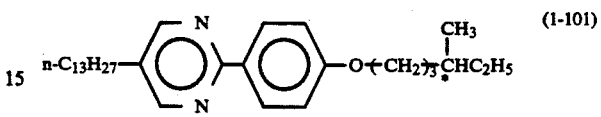 (1-101)
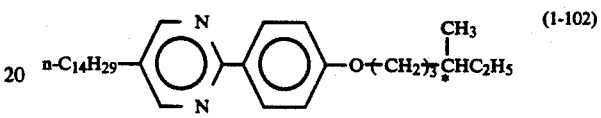 (1-102)
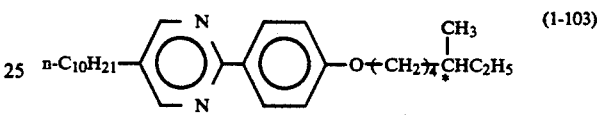 (1-103)
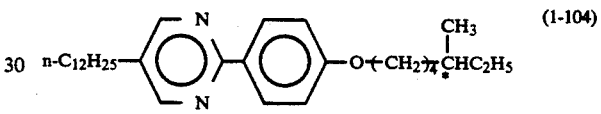 (1-104)
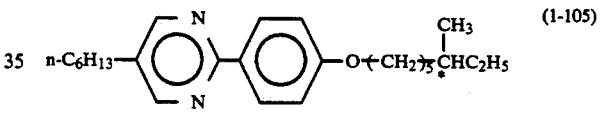 (1-105)
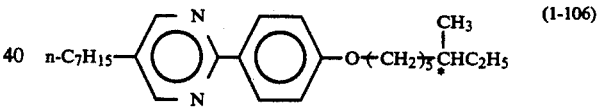 (1-106)
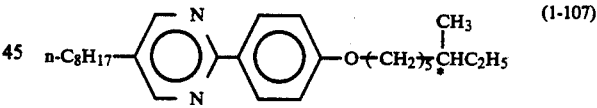 (1-107)
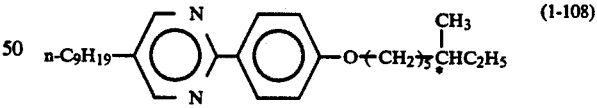 (1-108)
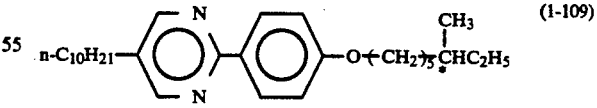 (1-109)
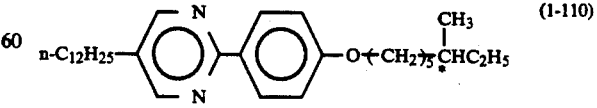 (1-110)
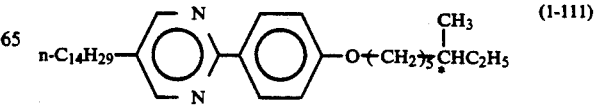 (1-111)

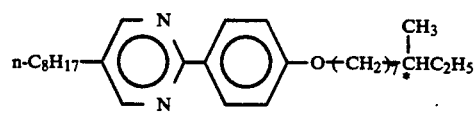 (1-112)
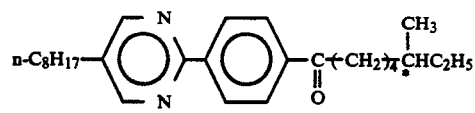 (1-113)
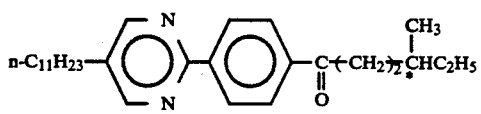 (1-114)
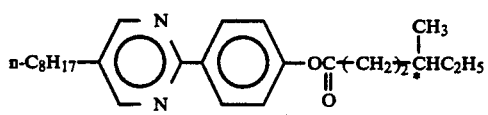 (1-115)
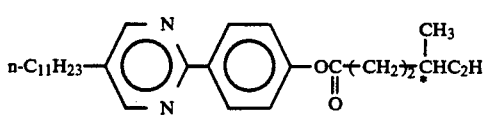 (1-116)
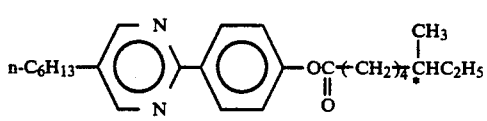 (1-117)
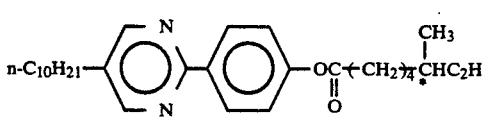 (1-118)
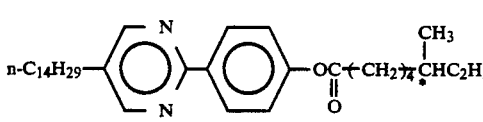 (1-119)
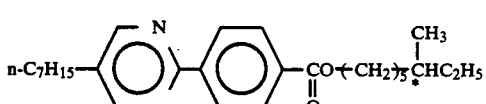 (1-120)
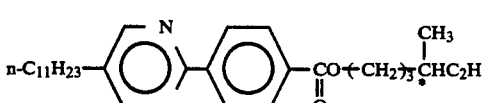 (1-121)
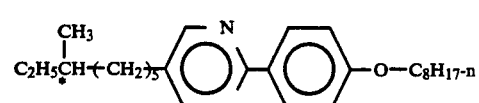 (1-122)
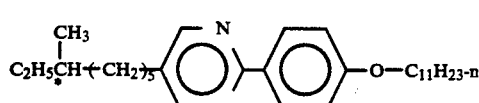 (1-123)
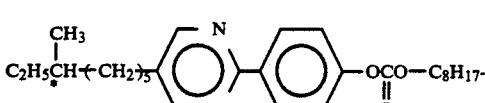 (1-124)
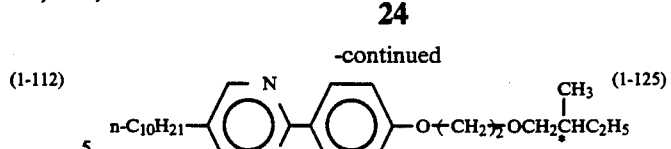 (1-125)
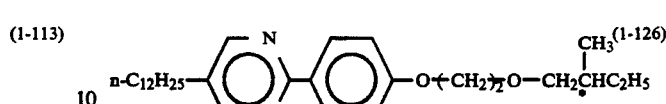 (1-126)
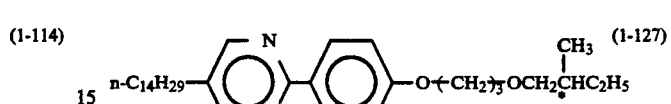 (1-127)
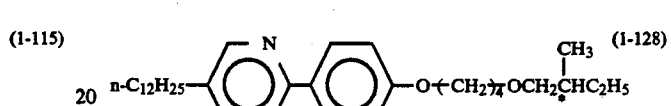 (1-128)
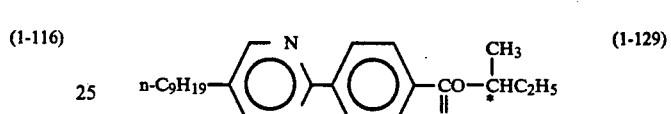 (1-129)
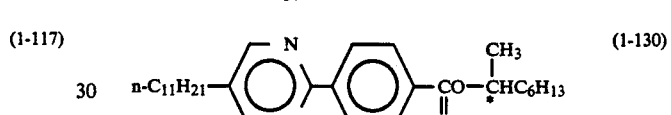 (1-130)
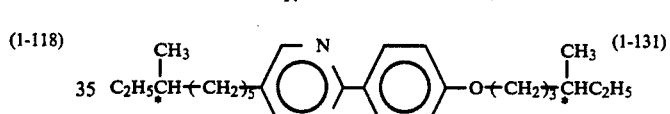 (1-131)
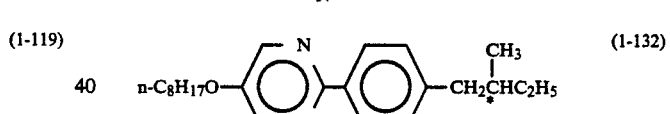 (1-132)
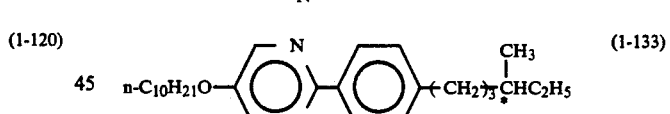 (1-133)
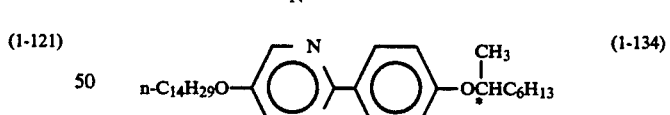 (1-134)
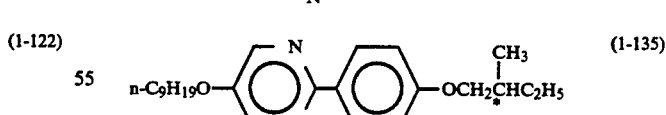 (1-135)
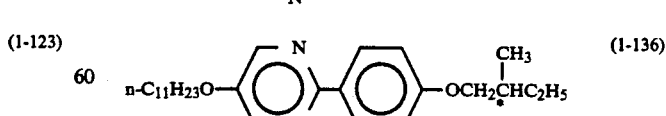 (1-136)
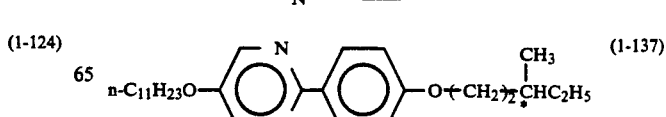 (1-137)

-continued
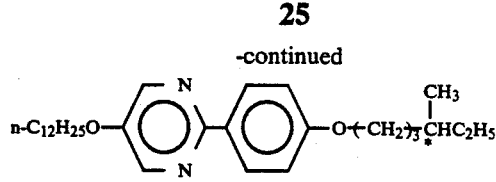 (1-138)
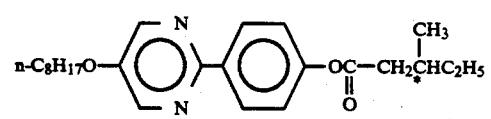 (1-139)
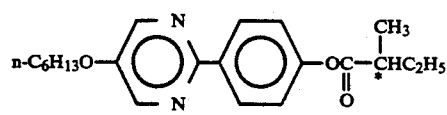 (1-140)
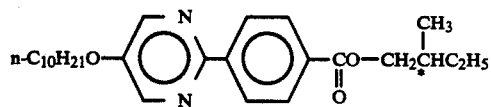 (1-141)
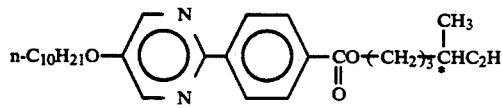 (1-142)
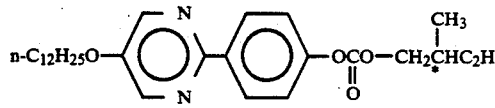 (1-143)
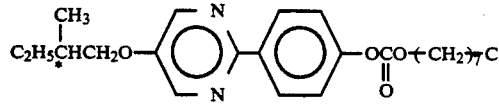 (1-144)
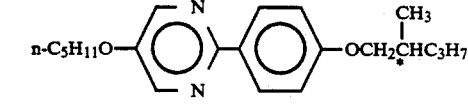 (1-145)
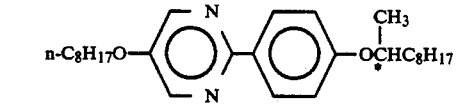 (1-146)
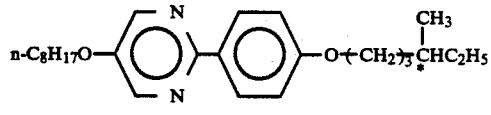 (1-147)
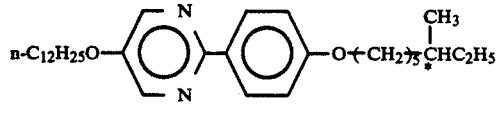 (1-148)
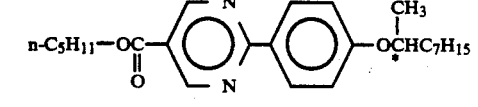 (1-149)
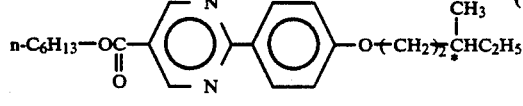 (1-150)
-continued
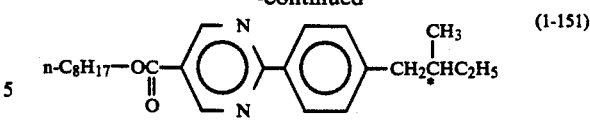 (1-151)
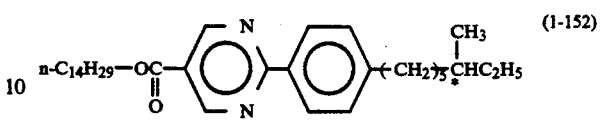 (1-152)
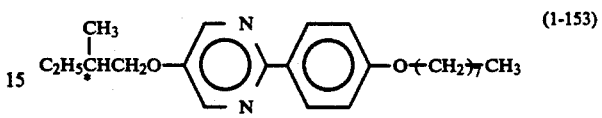 (1-153)
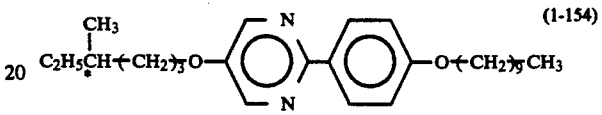 (1-154)
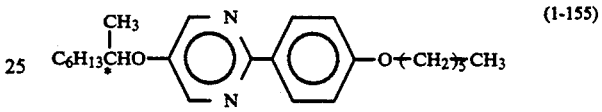 (1-155)
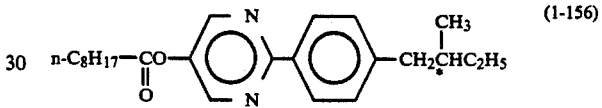 (1-156)
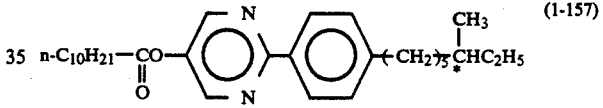 (1-157)
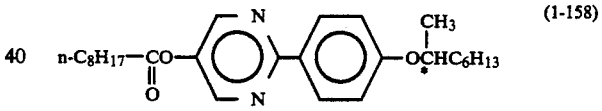 (1-158)
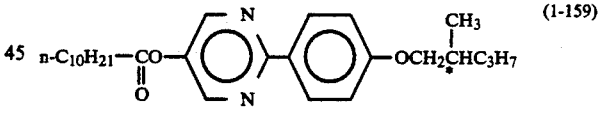 (1-159)
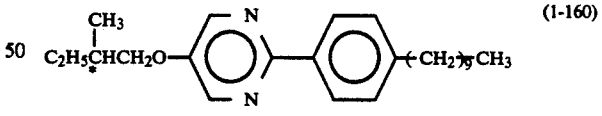 (1-160)
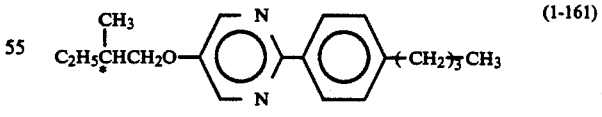 (1-161)
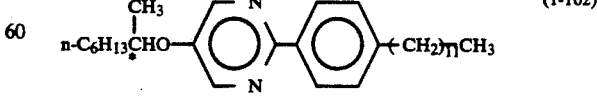 (1-162)
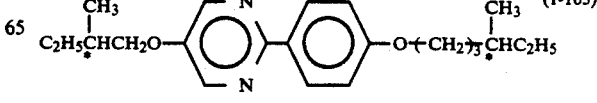 (1-163)

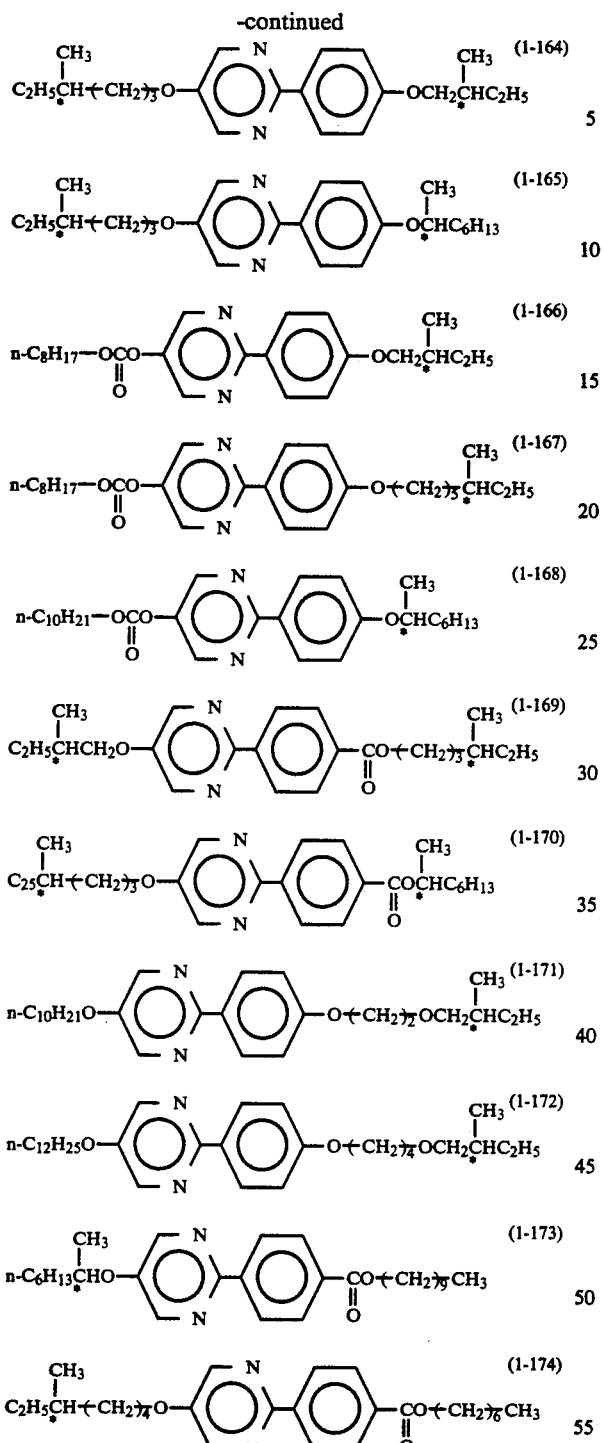

The compounds represented by the formula (I) may be synthesized through processes as disclosed by, e.g., Japanese Laid-Open Patent Applications (KOKAI) 93170/1986, 24576/1986, 129170/1986, 200972/1986, 200973/1986, 215372/1986 and 291574/1986, and East German Patent 95892 (1973). For example, the following reaction scheme may be used for the synthesis.

$R_1$, $R_2$ and $X_2$ are the same as defined above.

A representative example of synthesis of a compound represented by the formula (I) is described below.

SYNTHESIS EXAMPLE 1

Synthesis of Compound Example No. 1-71

A solution of 1.83 g (9.6 mmol) of p-toluene-sulfonic acid chloride in 5 ml of pyridine was added dropwise to a solution of 1.06 g (8.0 mmol) of 5-methoxyhexanol in 5 ml of pyridine below 5° C. on an iced water bath. After stirring for 6 hours at room temperature, the reaction mixture was injected into 100 ml of cold water and, after being acidified with 6N-hydrochloric acid, was extracted with isopropyl ether. The organic layer was washed with water and dried with anhydrous magnesium sulfate, followed by distilling-off of the solvent to obtain 5-methoxyhexyl-p-toluenesulfonate.

Separately, 2.0 g (6.41 mmol) of 5-decyl-2-(p-hydroxyphenyl)pyrimidine and 0.61 g of potassium hydroxide were added to 10 ml of dimethylformamide, and the mixture was stirred for 40 min. at 100° C. To the mixture was added the above-prepared 5-methoxyhexyl-p- toluenesulfonate followed by 4 hours of stirring under heating at 100° C. After the reaction, the reaction mixture was poured into 100 ml of cold water and extracted with benzene, followed by washing with water, drying with anhydrous magnesium sulfate and distilling-off of the solvent, to obtain a pale yellow oily product. The product was purified by column chromatography (silica gel—ethyl acetate/benzene=1/9) and recrystallized from hexane to obtain 1.35 g of 5-decyl-2-[4-(5'-methoxyhexyloxy)phenyl]pyrimidine.

Phase transition temperature (°C.)

Cry. $\underset{0.2}{\overset{3.5}{\rightleftarrows}}$ SmC $\underset{26.7}{\overset{27.9}{\rightleftarrows}}$ SmA $\underset{37.6}{\overset{40.3}{\rightleftarrows}}$ Iso.

SYNTHESIS EXAMPLE 2

Synthesis of Compound Example No. 1-76

2.04 g of 6-pentyloxyheptanol was dissolved in 8 ml of pyridine and cooled on an ice bath. Then, a solution of 2.26 g of tosyl chloride in 5 ml of pyridine was gradually added dropwise thereto below 5° C. in 5 min., followed by 5 hours of stirring at room temperature.

The reaction mixture was poured into 150 ml of iced water and acidified to about pH 3 with 6N-hydrochloric acid aqueous solution, followed by extraction with ethyl acetate. The extract liquid was then washed with water, dried with anhydrous magnesium sulfate and subjected to distilling-off of the solvent to obtain 2.98 g of 6-pentyloxyheptyl p-toluene-sulfonate.

3.12 g of 5-n-decyl-2-(4-hydroxyphenyl)pyrimidine and 0.53 g of potassium hydroxide were dissolved in 14 ml of dimethylformamide, and the mixture was stirred for 3 hours under heating at 100° C., followed by addition of the 2.98 g of 6-pentyloxyheptyl p-toluenesulfonate and 5 hours of stirring under heating at 100° C.

The reaction mixture was poured into 200 ml of iced water, acidified to pH of about 3 and extracted with benzene. The extract liquid was washed with water, dried with anhydrous magnesium sulfate and subjected to distilling-off of the solvent to obtain 4.71 g of a crude product, which was then purified by silica gel column chromatography (n-hexane/ethyl acetate=10/2) and recrystallized from hexane to obtain 1.56 g of 5-n-decyl-2-[4-(6-pentyloxyheptyloxy)phenyl]pyrimidine.

IR (cm$^{-1}$): 2924, 2852, 1610, 1586, 1472, 1436, 1254, 1168, 1096, 798

Phase transition temperature (°C.)

Cryst. $\underset{22.7}{\overset{30.4}{\rightleftarrows}}$ Sm3 $\underset{33.3}{\overset{35.5}{\rightleftarrows}}$ SmC* $\underset{39.8}{\overset{41.4}{\rightleftarrows}}$ Iso.

The compounds other than those of the above-mentioned Synthesis Examples may be prepared along the following reaction scheme A or B.

Reaction Scheme A:

$R_1-X_1-\underset{N}{\overset{N}{\bigcirc}}-\bigcirc-OH$ $\downarrow$ $Cl-\underset{O}{\overset{CH_3}{\underset{\|}{C}}}(CH_2)_q\overset{|}{C}H(CH_2)_r-O-R_9$ $R_1-X_1-\underset{N}{\overset{N}{\bigcirc}}-\bigcirc-OC(CH_2)_q\overset{CH_3}{\underset{|}{C}H}(CH_2)_r-OR_9$ Reaction Scheme B:

$R_1-X_1-\underset{N}{\overset{N}{\bigcirc}}-\bigcirc-\underset{O}{\overset{\|}{C}}-Cl$ $\downarrow HO(CH_2)_q\overset{CH_3}{\underset{|}{C}H}(CH_2)_r-O-R_9$ $R_1-X_1-\underset{N}{\overset{N}{\bigcirc}}-\bigcirc-\underset{O}{\overset{\|}{C}O}(CH_2)_q\overset{CH_3}{\underset{|}{C}H}(CH_2)_r-OR_9$ In the above schemes, $R_1$, $R_9$, $X_1$, q and r are the same as defined before.

Specific examples of the compounds represented by the above-mentioned general formula (II) may include those shown by the following structural formulas.

(2-1) n-C$_4$H$_9$—⟨H⟩—CO—O—⟨⟩—CO—O—CH$_2$CH*—C$_5$H$_{11}$-n, with F on CH*

(2-2) n-C$_3$H$_7$—⟨H⟩—CO—O—⟨⟩—CO—O—CH$_2$CH*—C$_8$H$_{17}$-n, with F on CH*

(2-3) n-C$_5$H$_{11}$—⟨H⟩—CO—O—⟨⟩—CO—O—CH$_2$CH*—C$_6$H$_{13}$-n, with F on CH*

(2-4) n-C$_8$H$_{17}$—⟨H⟩—CO—O—⟨⟩—CO—O—CH$_2$CH*—C$_4$H$_9$-n, with F on CH*

(2-5) n-C$_3$H$_7$—⟨H⟩—CO—O—⟨⟩—CO—O—CH$_2$CH*—C$_6$H$_{13}$-n, with F on CH*

(2-6) n-C$_4$H$_9$—⟨H⟩—CO—O—⟨⟩—CO—O—CH$_2$CH*—C$_6$H$_{13}$-n, with F on CH*

(2-7) n-C$_5$H$_{11}$—⟨H⟩—CO—O—⟨⟩—CO—O—CH$_2$CH*—C$_7$H$_{15}$-n, with F on CH*

(2-8) n-C$_3$H$_7$—⟨H⟩—CO—O—⟨⟩—CO—O—CH$_2$CH*—C$_7$H$_{15}$-n, with F on CH*

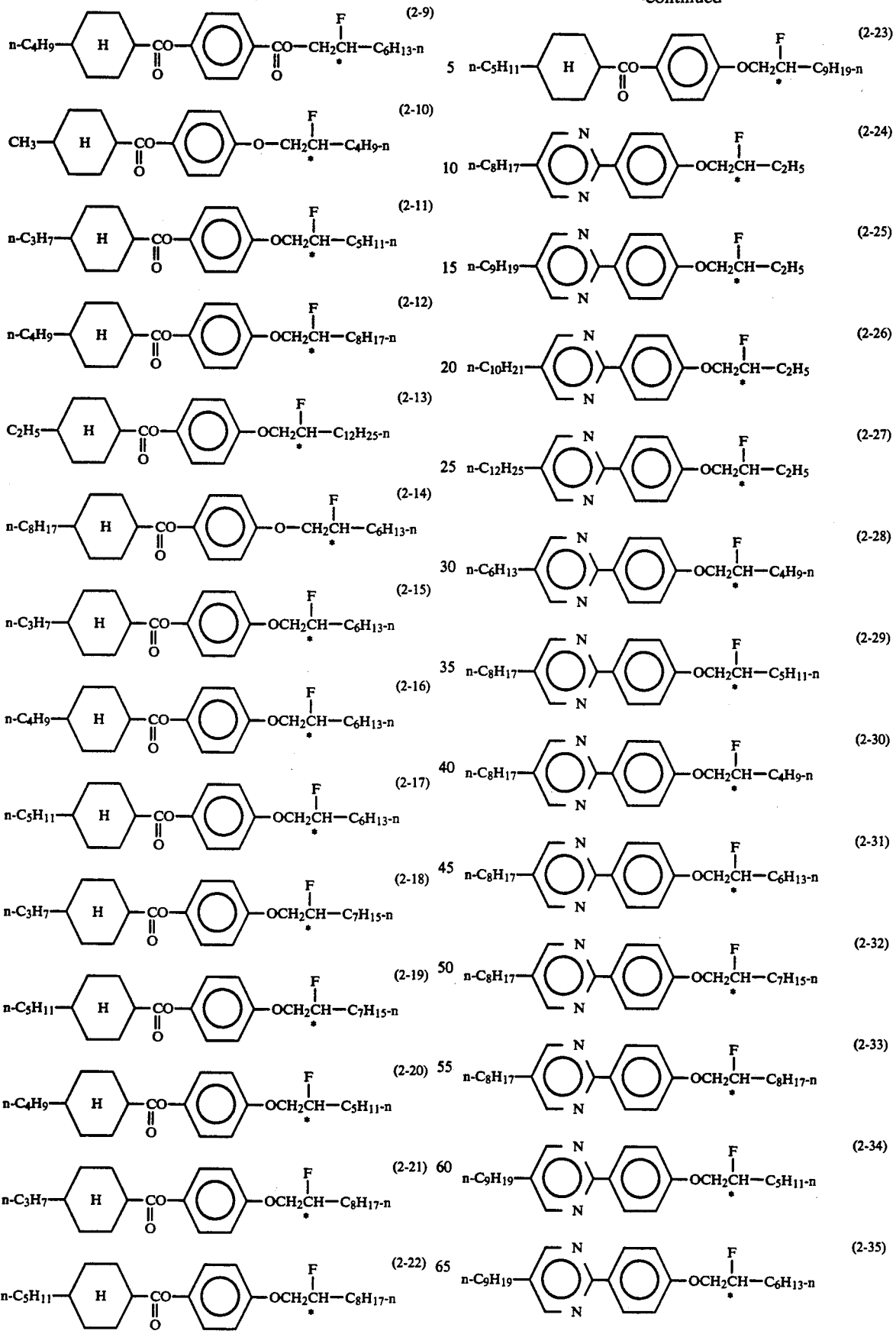

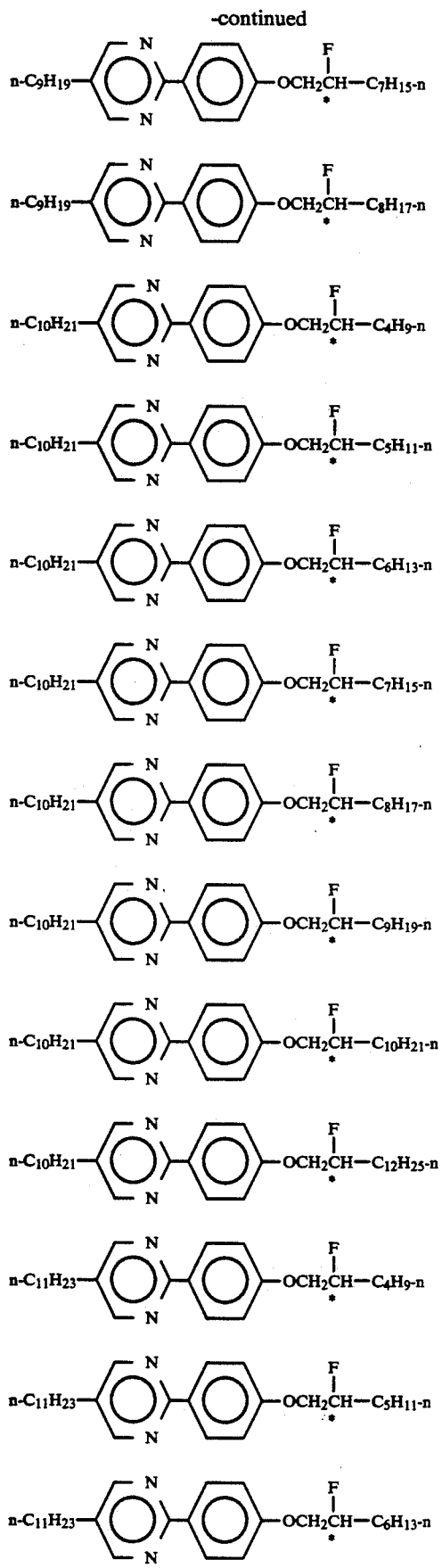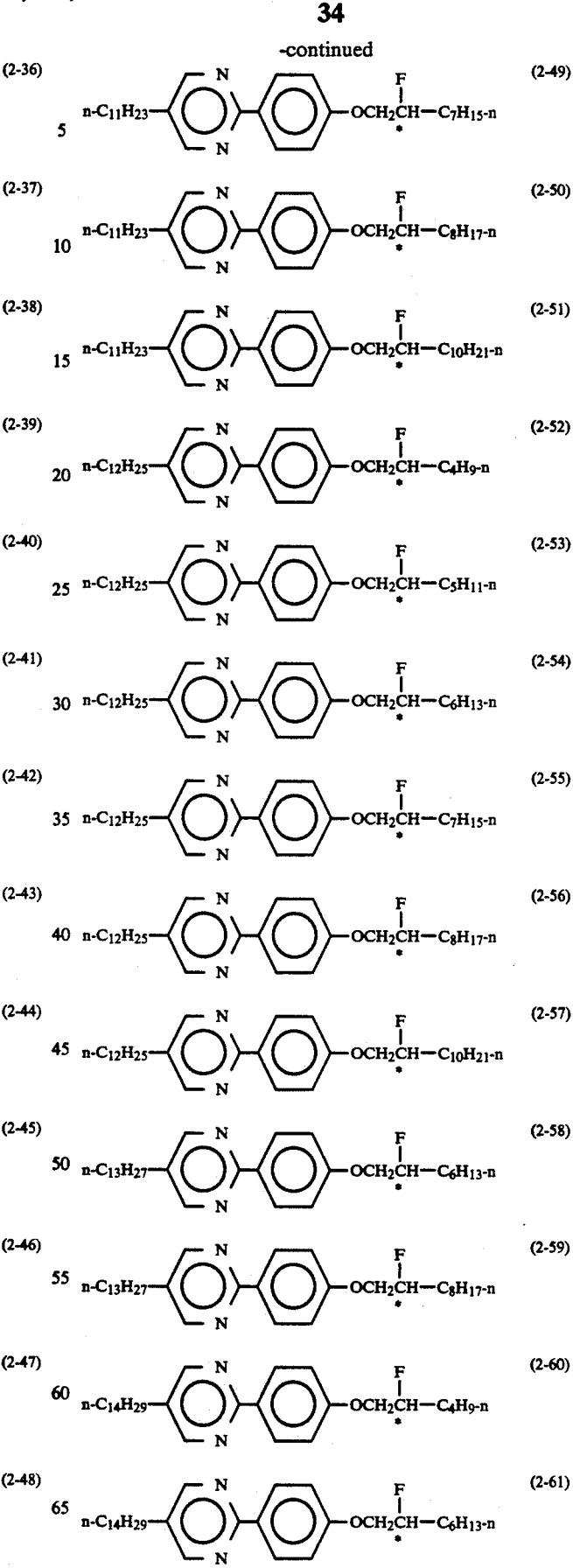

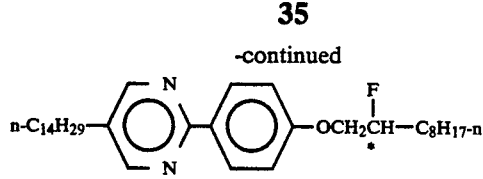 (2-62)
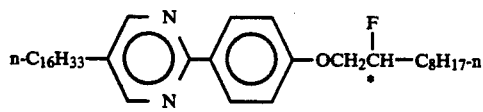 (2-63)
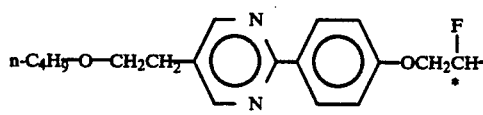 (2-64)
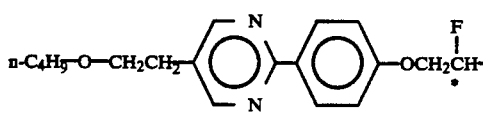 (2-65)
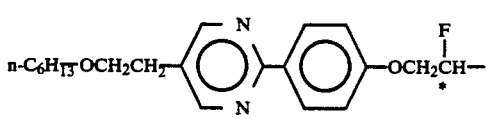 (2-66)
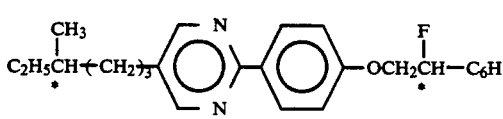 (2-67)
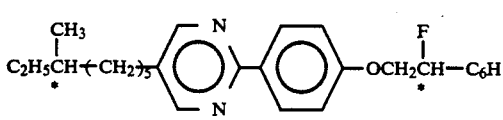 (2-68)
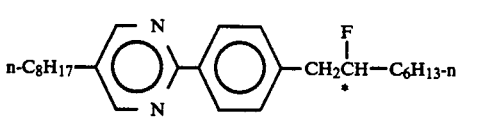 (2-69)
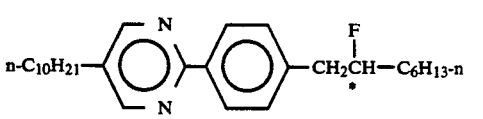 (2-70)
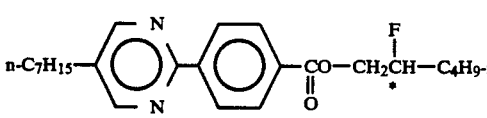 (2-71)
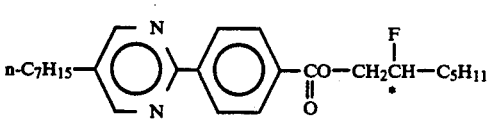 (2-72)
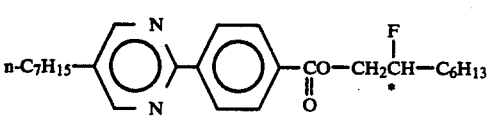 (2-73)
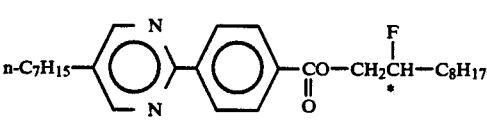 (2-74)
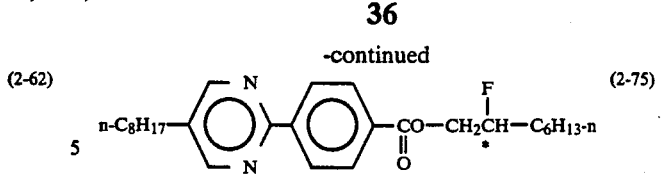 (2-75)
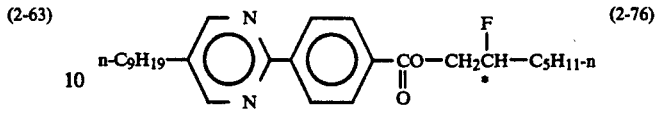 (2-76)
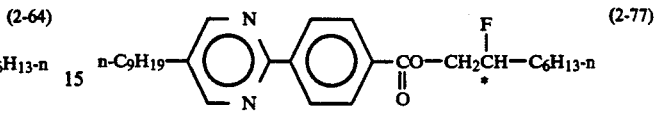 (2-77)
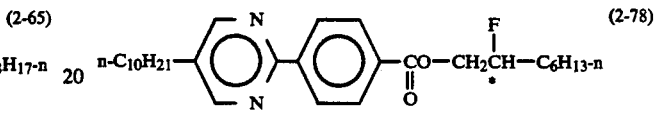 (2-78)
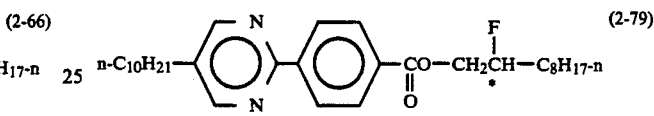 (2-79)
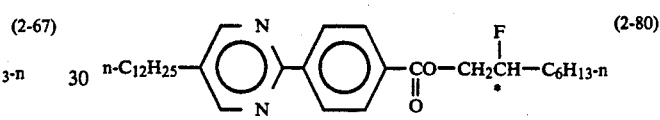 (2-80)
(2-81)
(2-82)
The compounds represented by the general formula (II) may be synthesized through the following reaction schemes A, B and C.
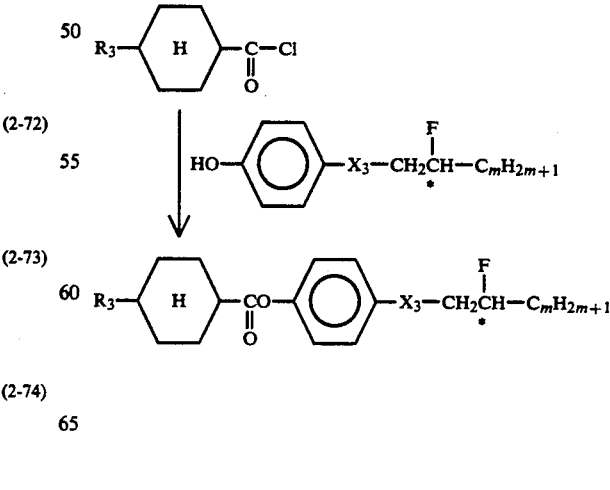
Reaction scheme A Reaction scheme B
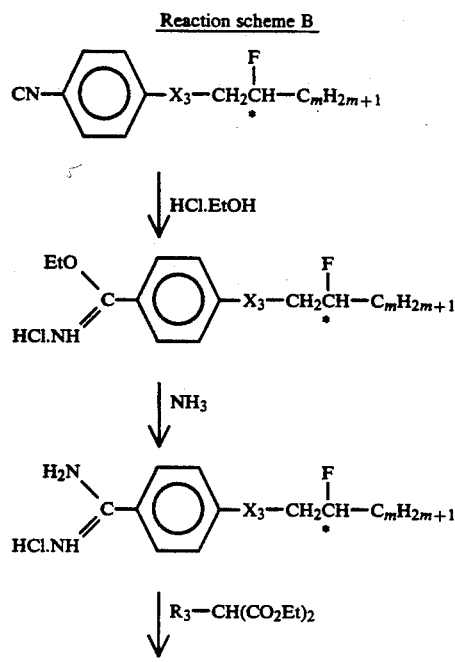
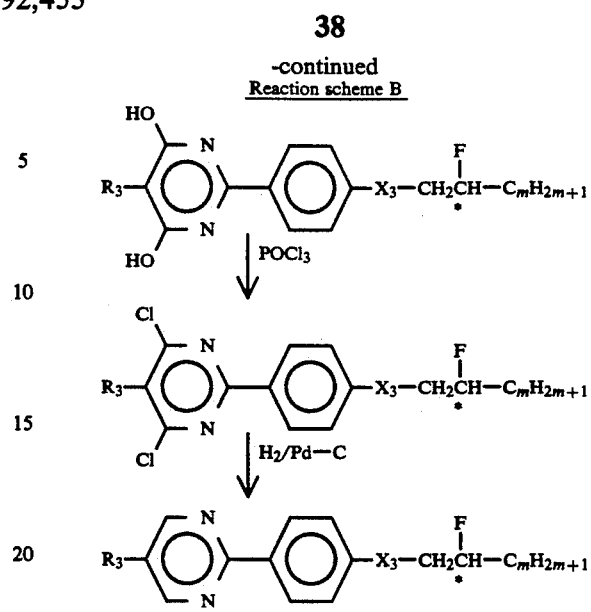
Reaction scheme C
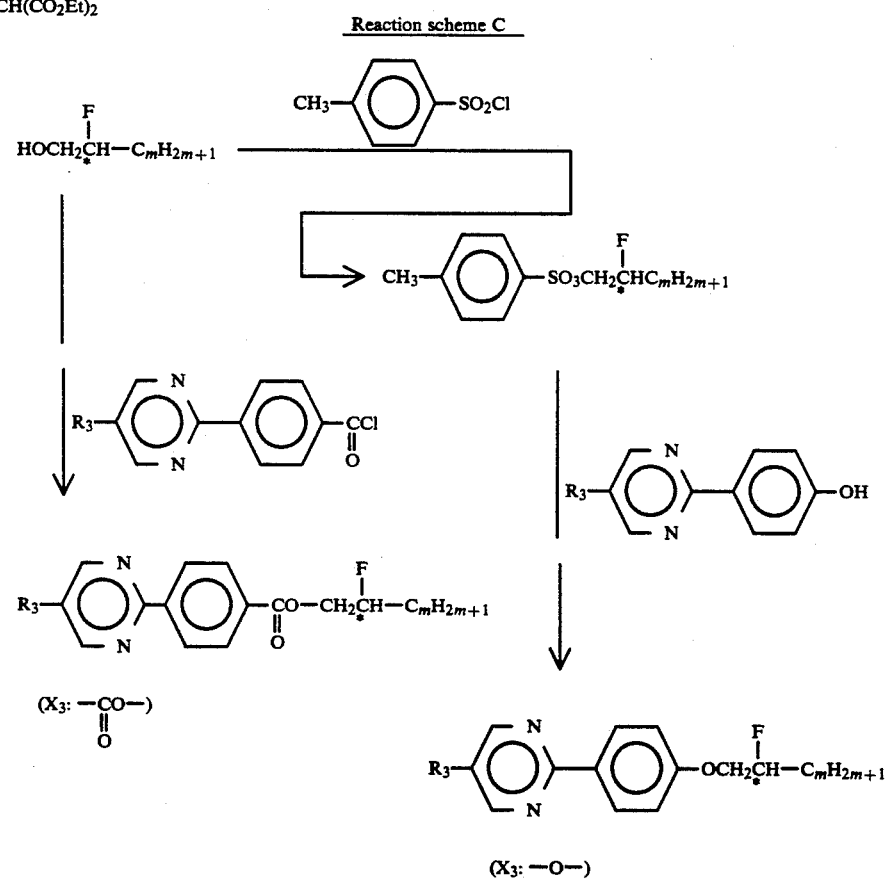
Representative examples of synthesis of the compound represented by the general formula (II) are shown hereinbelow.
SYNTHESIS EXAMPLE 3
Synthesis of Compound Example 2-17
1.00 g (4.16 mM) of p-2-fluorooctyloxyphenol was dissolved in a mixture of 10 ml of pyridine and 5 ml of toluene, and a solution of 1.30 g (6.0 mM) of trans-4-n- pentylcyclohexanecarbonyl chloride was added dropwise thereto in 20–40 min. at below 5° C. After the addition, the mixture was stirred overnight at room temperature to obtain a white precipitate.

After the reaction, the reaction product was extracted with benzene, and the resultant benzene layer was washed with distilled water, followed by drying with magnesium sulfate and distilling-off of the benzene, purification by silica gel column chromatography and recrystallization from ethanol/methanol to obtain 1.20 g (2.85 mM) of trans-4-n-pentylcyclohexanecarboxylic acid-p-2-fluorooctyloxyphenyl-ester. (Yield: 68.6 %)

NMR data (ppm) 0.83–2.83 ppm (34H, m); 4.00–4.50 ppm (2H, q); 7.11 ppm (4H, s)

IR data (cm$^{-1}$): 3456, 2928, 2852, 1742, 1508, 1470, 1248, 1200, 1166, 1132, 854.

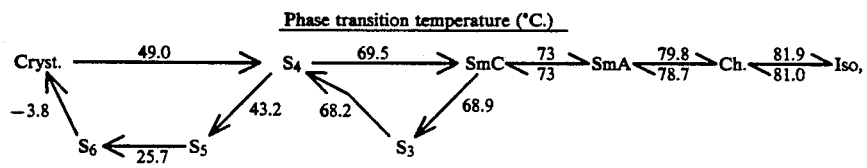

Herein, the respective symbols denote the following phases, Iso.: isotropic phase, Ch.: cholesteric phase, SmA: smectic A phase, SmC: smectic C phase, $S_3$–$S_6$: phases of higher other than SmC or SmC* (chiral smectic C phase), and Cryst.: crystal phase.

SYNTHESIS EXAMPLE 4

Synthesis of Compound Example 2-29

In a vessel sufficiently replaced with nitrogen, 0.40 g (3.0 mmol) of (−)-2-fluoroheptanol and 1.00 g (13 mmol) of dry pyridine were placed and dried for 30 min. under cooling on an ice bath. Into the solution, 0.69 g (3.6 mmol) of p-toluenesulfonyl chloride was added, and the mixture was stirred for 5 hours. After the reaction, 10 ml of 1N-HCl was added, and the resultant mixture was subjected to two times of extraction with 10 ml of methylene chloride. The extract liquid was washed once with 10 ml of distilled water and dried with an appropriate amount of anhydrous sodium sulfate, followed by distilling-off of the solvent to obtain 0.59 g (2.0 mmol) of (+)-2-fluoroheptyl p-toluenesulfonate.

The yield was 66 %, and the product showed the following optical rotation and IR data.

Optical rotation:

$[\alpha]_D^{26.4}$ +2.59 degrees (c=1, CHCl$_3$) $[\alpha]_{435}^{23.6}$ +9.58 degrees (c=1, CHCl$_3$)

IR (cm$^{-1}$): 2900, 2850, 1600, 1450, 1350, 1170, 1090 980, 810, 660, 550

0.43 g (1.5 mmol) of the thus obtained (+)-2-fluoroheptyl p-toluenesulfonate and 0.28 g (1.0 mmol) of 5-octyl-2-(4-hydroxyphenyl)pyrimidine were mixed with 0.2 ml of 1-butanol, followed by sufficient stirring. To the solution was quickly added a previously obtained alkaline solution of 0.048 g (1.2 mmol) of sodium hydroxide in 1.0 ml of 1-butanol, followed by 5.5 hours of heat-refluxing. After the reaction, 10 ml of distilled water was added, and the mixture was extracted respectively once with 10 ml of benzene and 5 ml of benzene, followed by drying with an appropriate amount of anhydrous sodium sulfate, distilling-off of the solvent and purification by silica gel column chromatography (chloroform) to obtain 0.17 g (0.43 mmol) of objective (+)-5-octyl-2-[4-(2-fluoroheptyloxy)phenyl]pyrimidine.

The yield was 43%, and the product showed the following optical rotation and IR data.

Optical rotation:

$[\alpha]_D^{25.6}$ +0.44 degree (c=1, CHCl$_3$) $[\alpha]_{435}^{22.4}$ +4.19 degrees (c=1, CHCl$_3$)

IR (cm$^{-1}$): 900, 2850, 1600, 1580, 1420, 1250 260, 800, 720, 650, 550.

Specific examples of the compounds represented by the above-mentioned general formula (III) may include those shown by the following structural formulas.

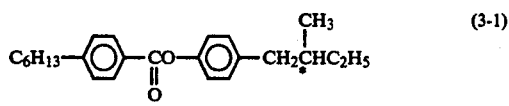 (3-1)

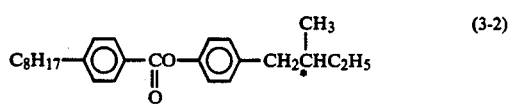 (3-2)

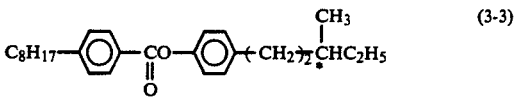 (3-3)

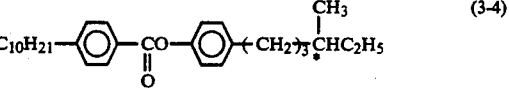 (3-4)

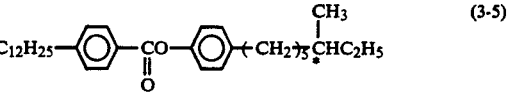 (3-5)

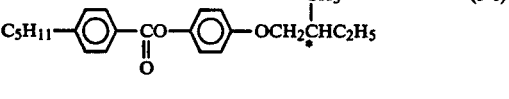 (3-6)

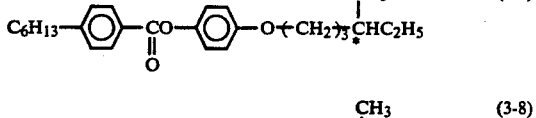 (3-7)

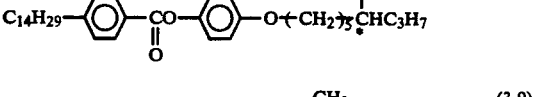 (3-8)

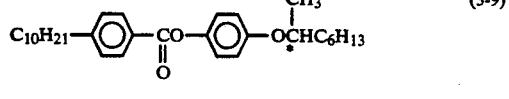 (3-9)

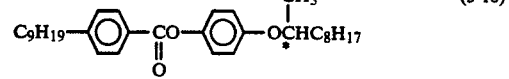 (3-10)

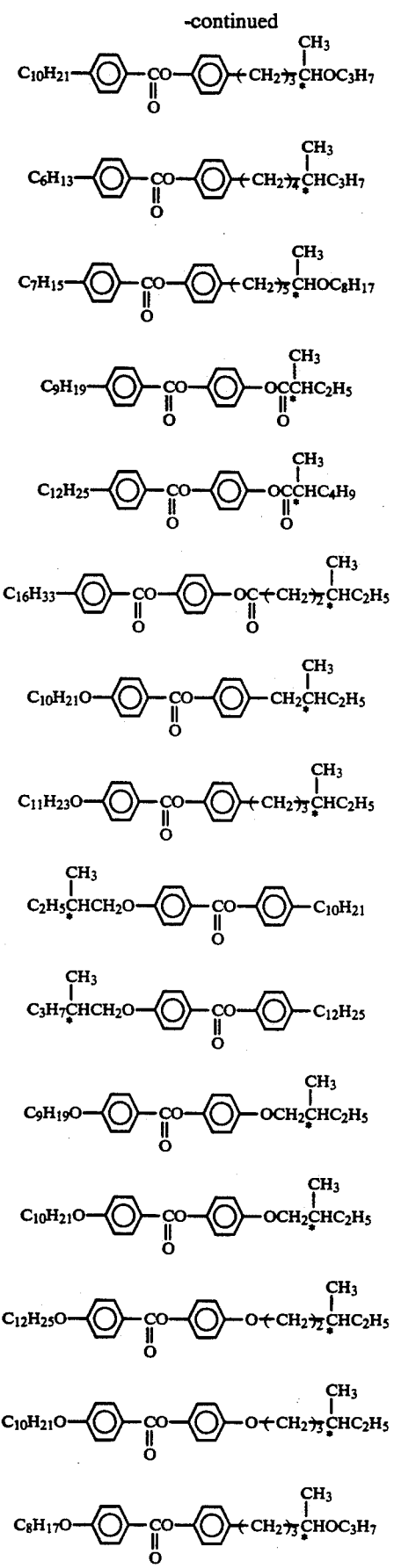
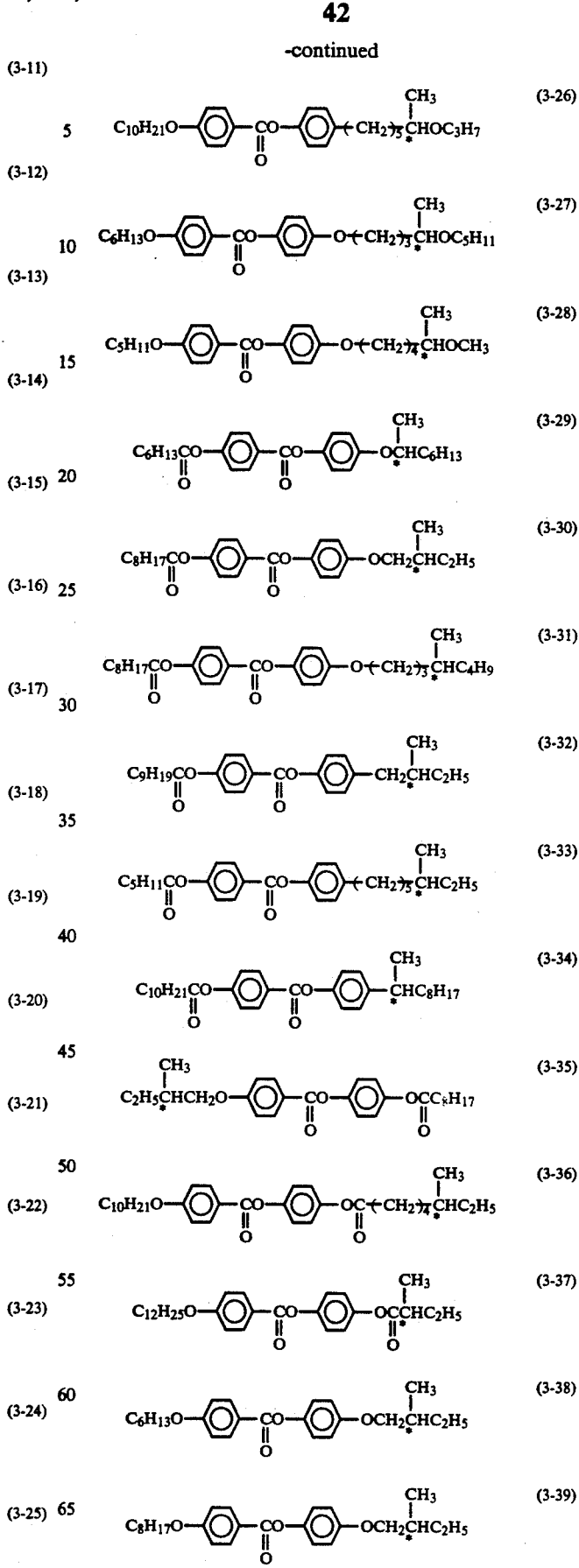

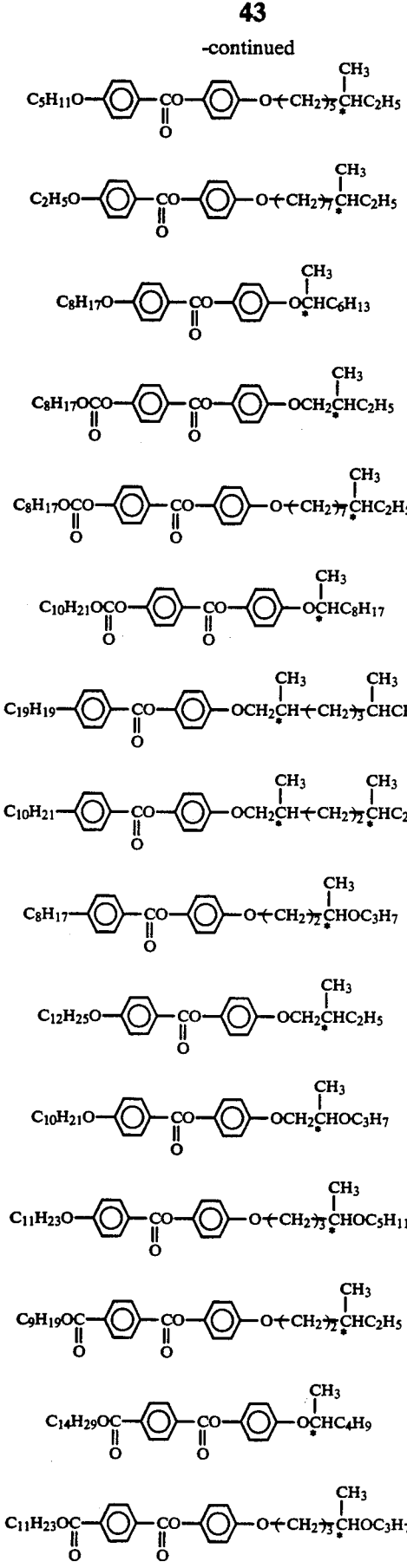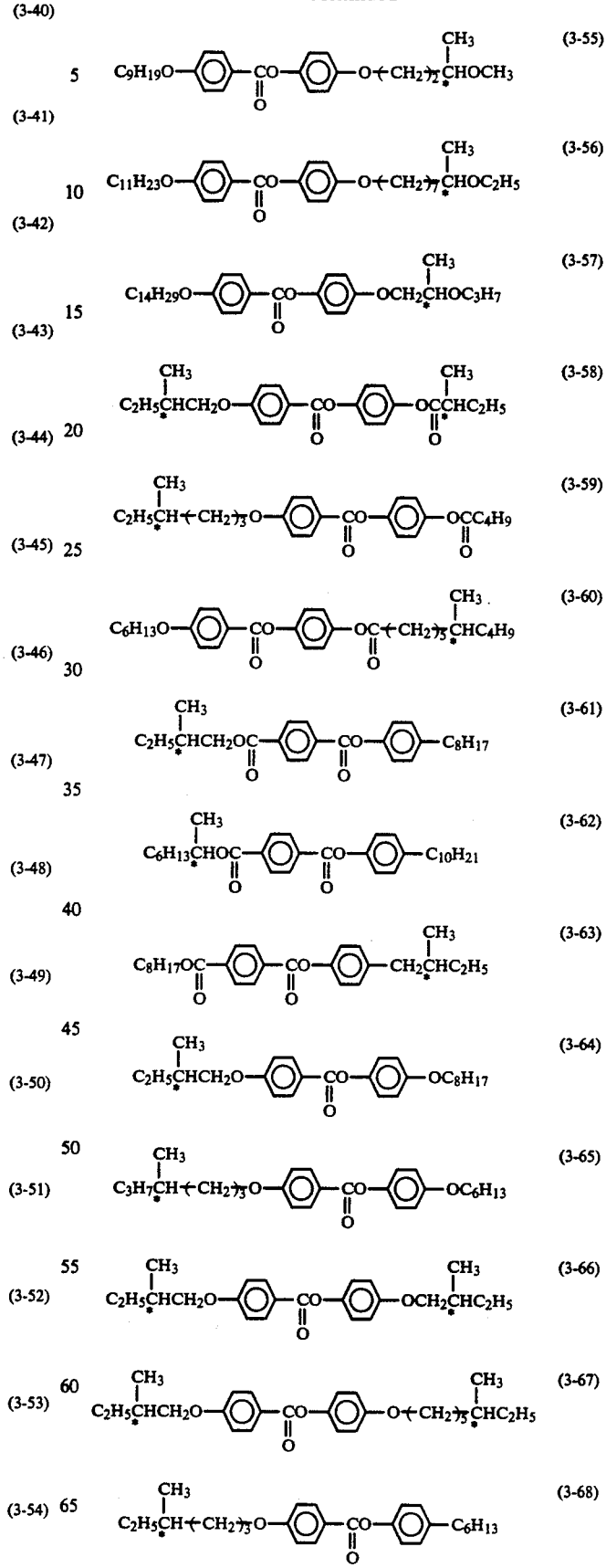

-continued
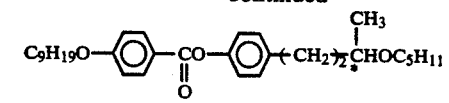 (3-69)
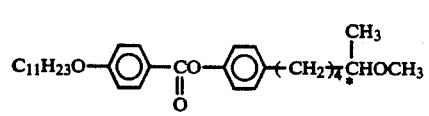 (3-70)
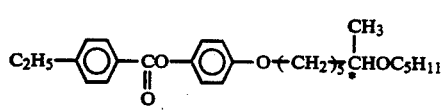 (3-71)
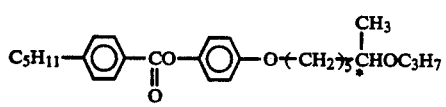 (3-72)
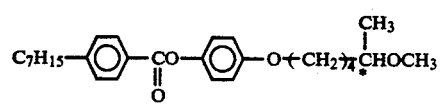 (3-73)
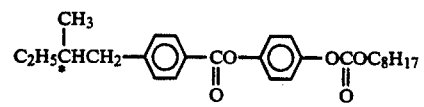 (3-74)
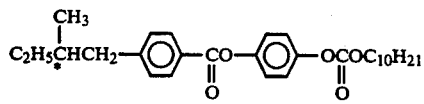 (2-75)
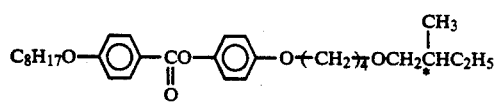 (3-76)
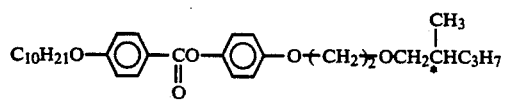 (3-77)
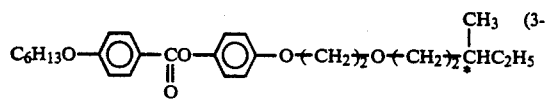 (3-78)
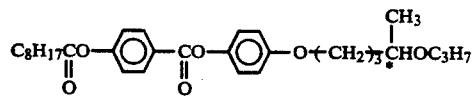 (3-79)
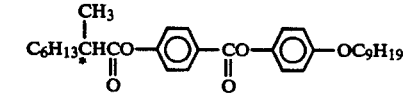 (3-80)
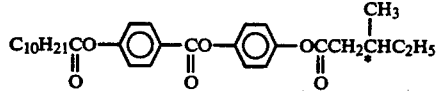 (3-81)
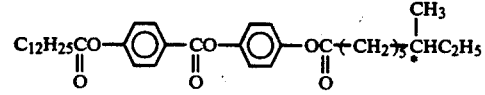 (3-82)
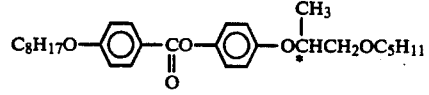 (3-83)
-continued
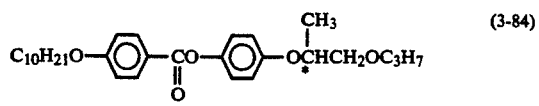 (3-84)
The compounds represented by the formula (III), for example,
may be synthesized through the following reaction scheme.
Reaction scheme:
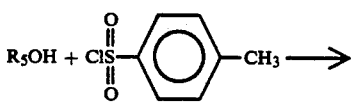
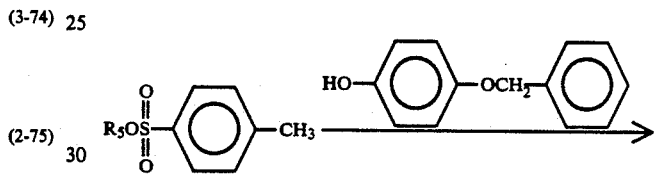
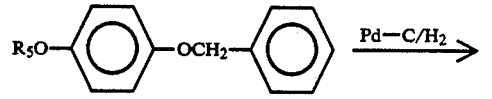
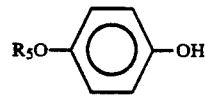
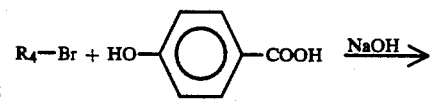
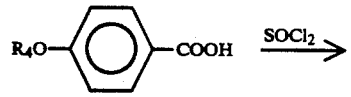
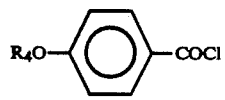
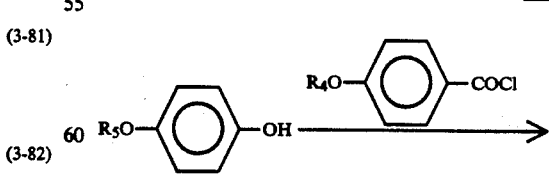
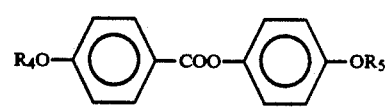
$R_4$ and $R_5$ are the same as defined above.

Specific examples of the compounds represented by the above-mentioned general formula (IV) may include those shown by the following structural formulas.
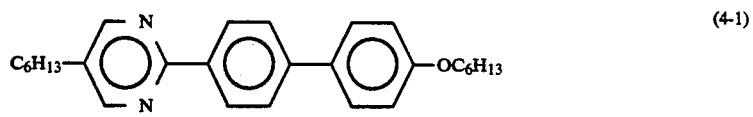 (4-1)
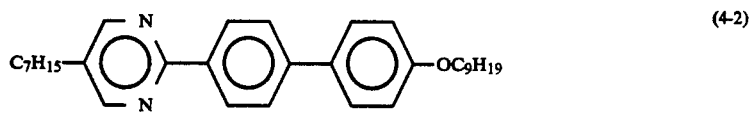 (4-2)
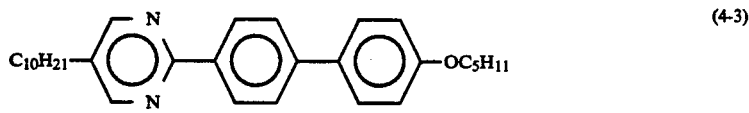 (4-3)
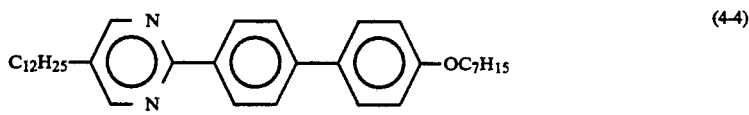 (4-4)
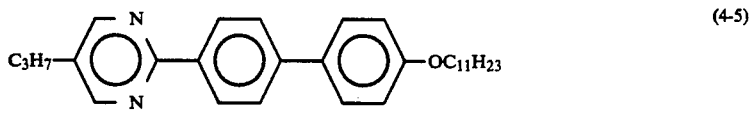 (4-5)
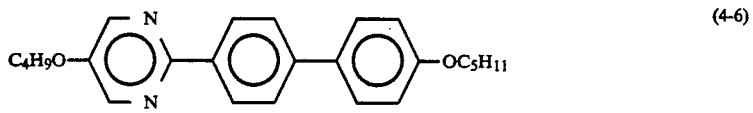 (4-6)
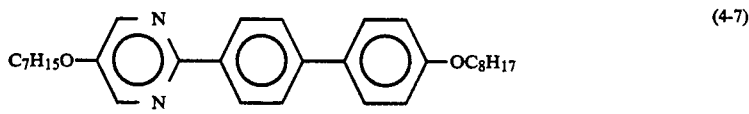 (4-7)
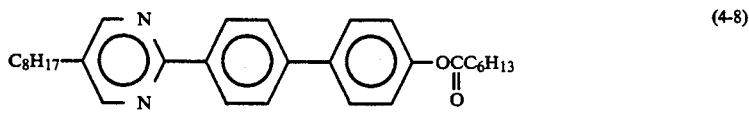 (4-8)
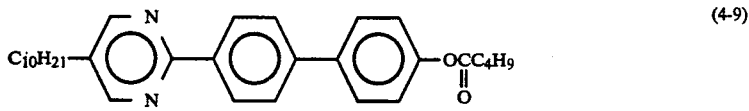 (4-9)
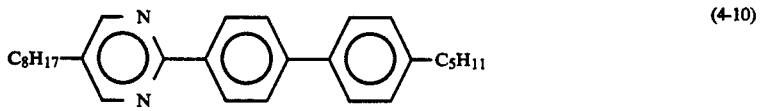 (4-10)
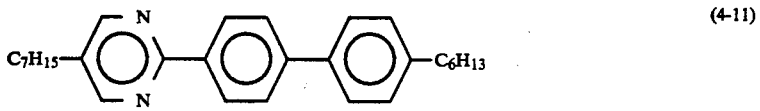 (4-11)
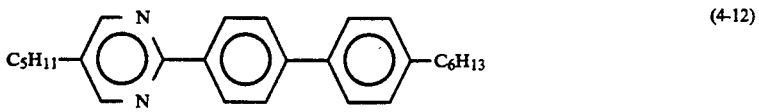 (4-12)

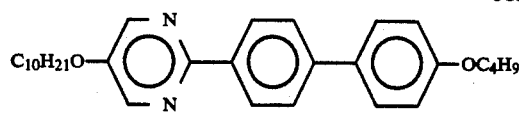 (4-13)
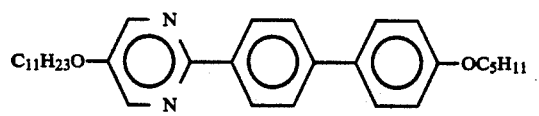 (4-14)
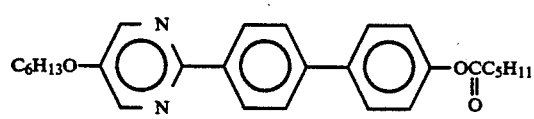 (4-15)
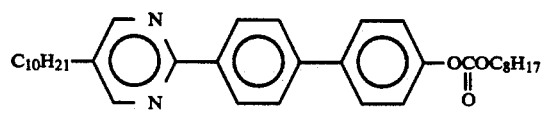 (4-16)
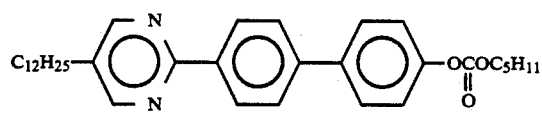 (4-17)
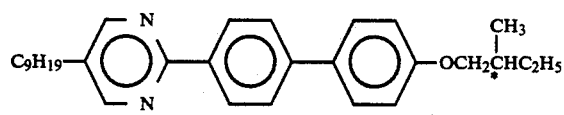 (4-18)
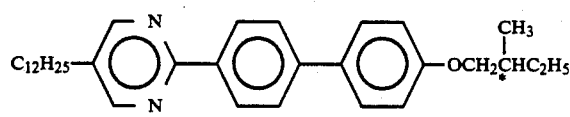 (4-19)
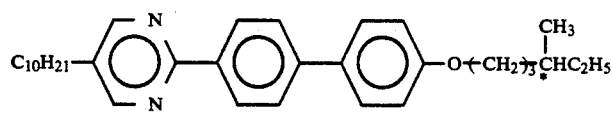 (4-20)
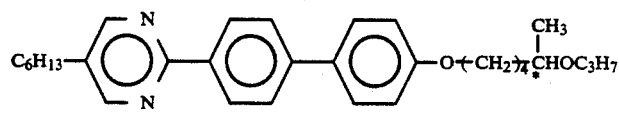 (4-21)
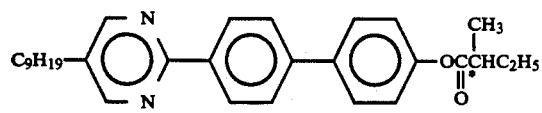 (4-22)
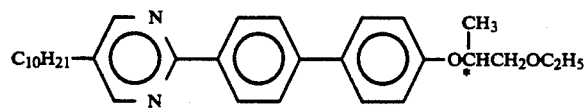 (4-23)
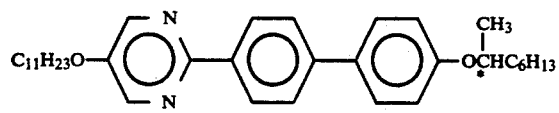 (4-24)
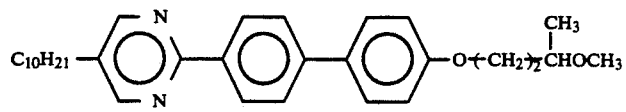 (4-25)

-continued
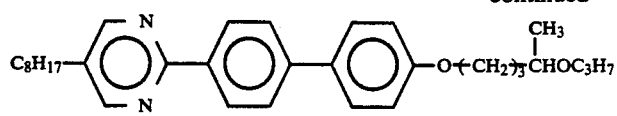 (4-26)
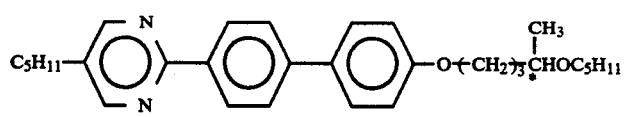 (4-27)
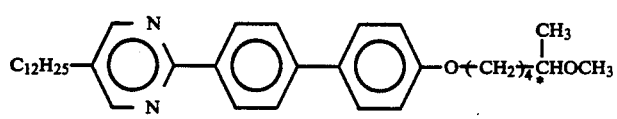 (4-28)
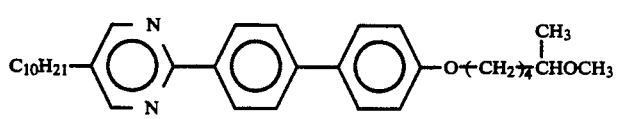 (4-29)
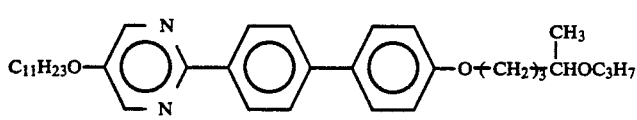 (4-30)
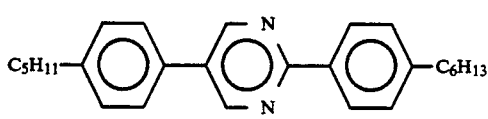 (4-31)
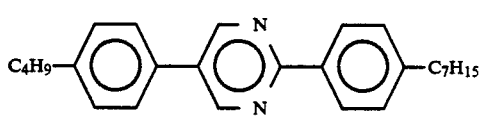 (4-32)
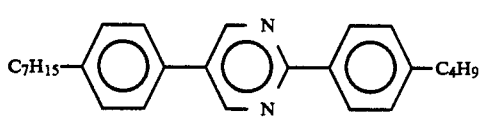 (4-33)
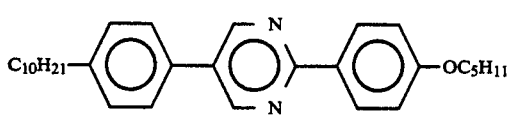 (4-34)
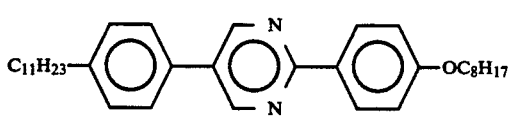 (4-35)
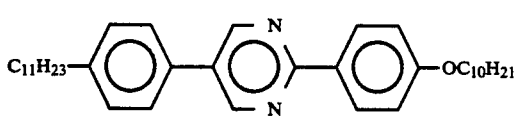 (4-36)
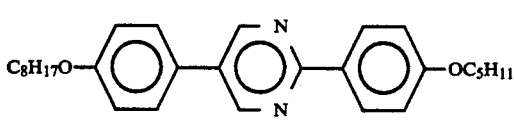 (4-37)
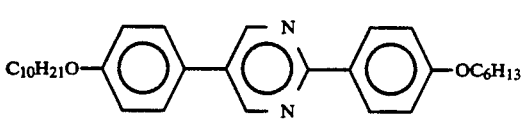 (4-38)

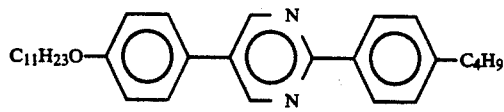 (4-39)
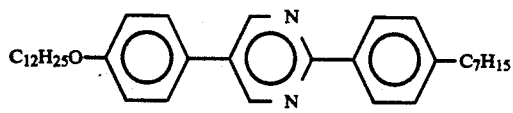 (4-40)
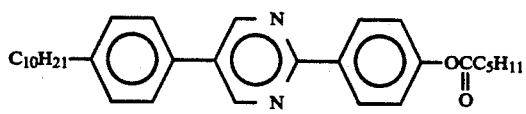 (4-41)
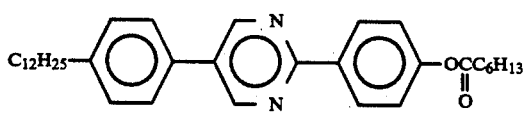 (4-42)
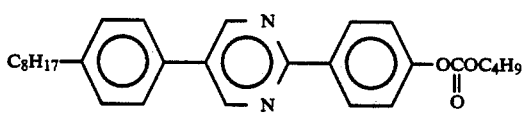 (4-43)
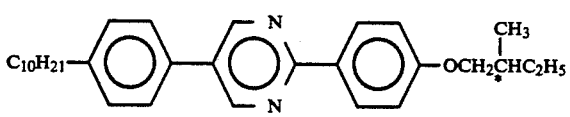 (4-44)
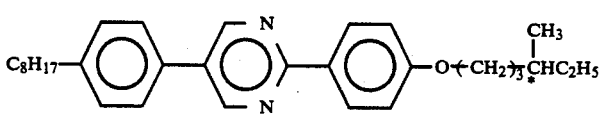 (4-45)
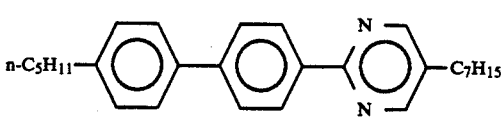 (4-46)
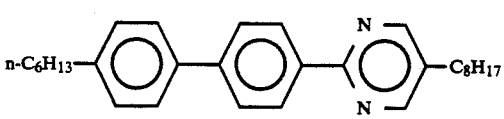 (4-47)
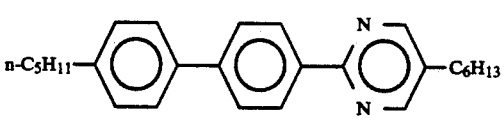 (4-48)
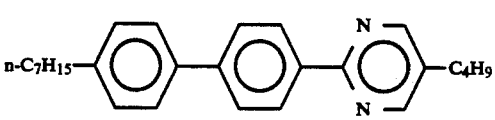 (4-49)
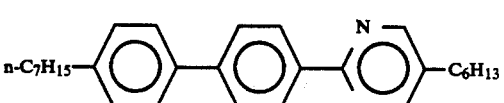 (4-50)
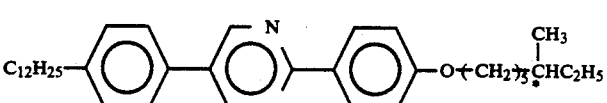 (4-51)

-continued
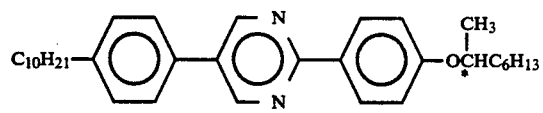 (4-52)
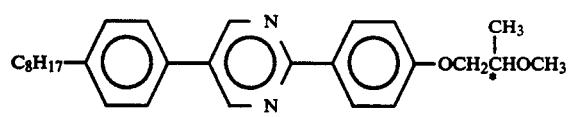 (4-53)
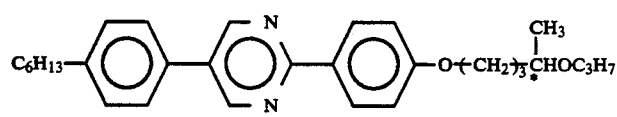 (4-54)
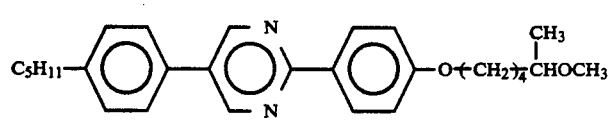 (4-55)
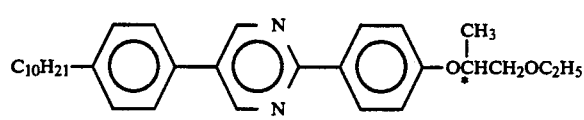 (4-56)
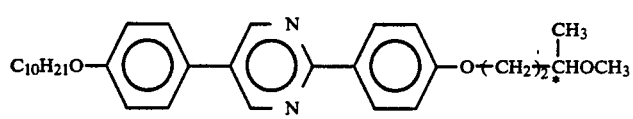 (4-57)
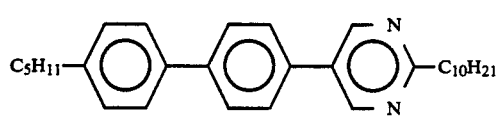 (4-58)
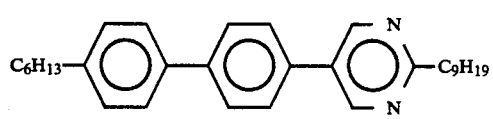 (4-59)
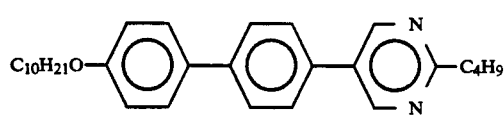 (4-60)
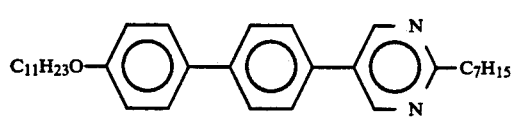 (4-61)
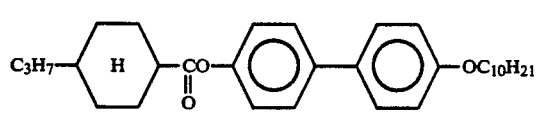 (4-62)
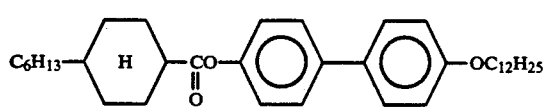 (4-63)
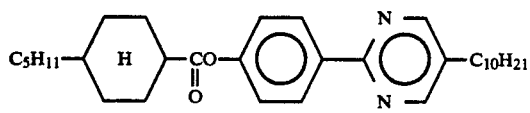 (4-64)

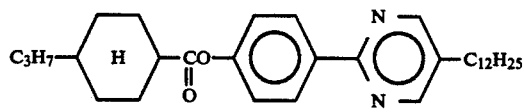 (4-65)
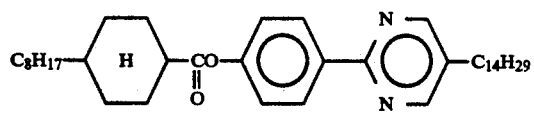 (4-66)
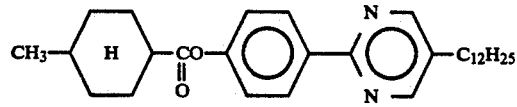 (4-67)
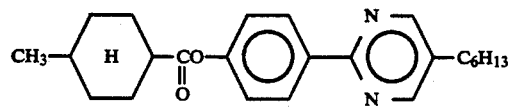 (4-68)
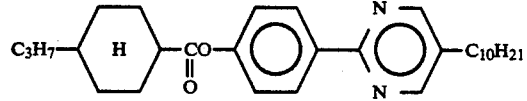 (4-69)
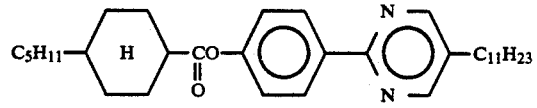 (4-70)
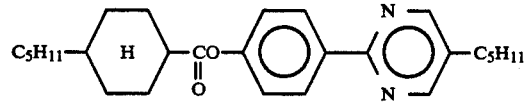 (4-71)
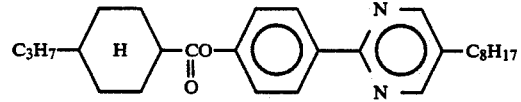 (4-72)
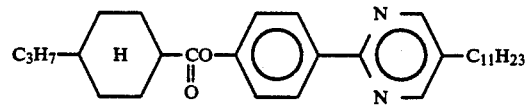 (4-73)
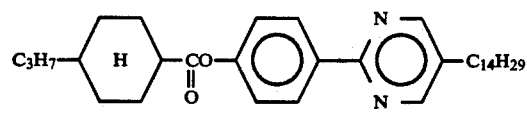 (4-74)
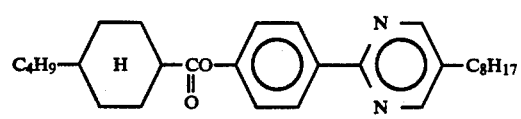 (4-75)
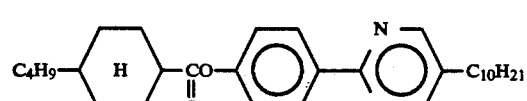 (4-76)
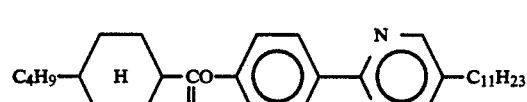 (4-77)

-continued
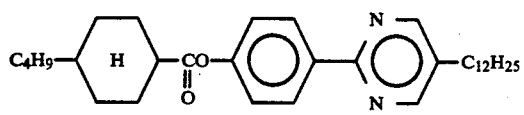 (4-78)
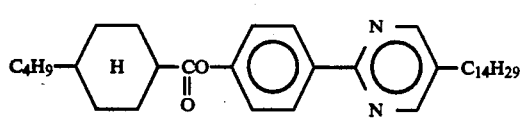 (4-79)
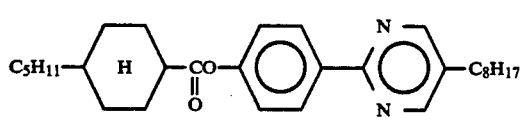 (4-80)
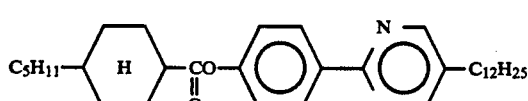 (4-81)
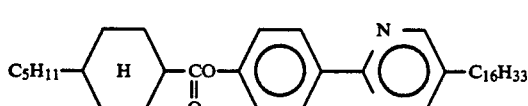 (4-82)
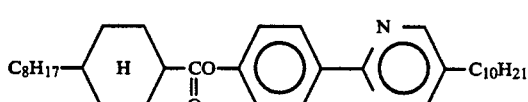 (4-83)
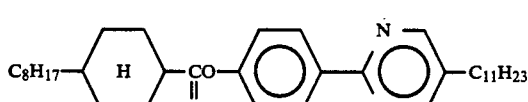 (4-84)
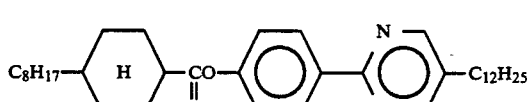 (4-85)
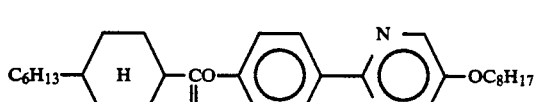 (4-86)
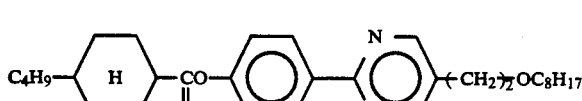 (4-87)
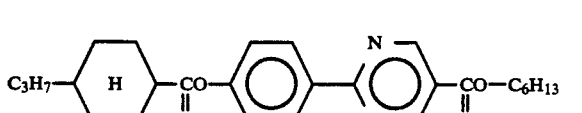 (4-88)
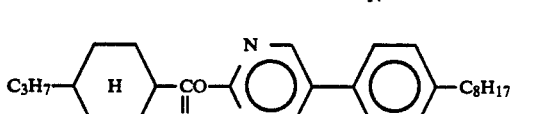 (4-89)
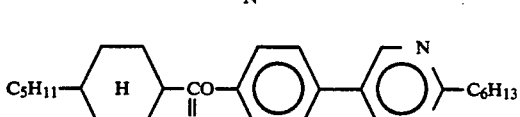 (4-90)

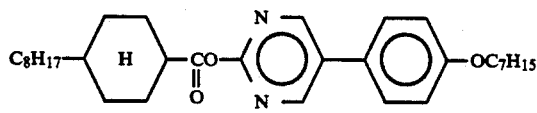 (4-91)
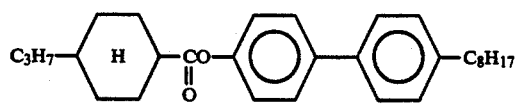 (4-92)
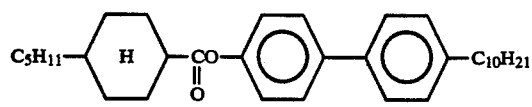 (4-93)
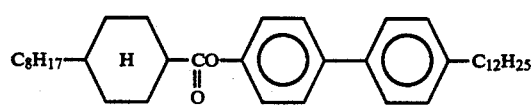 (4-94)
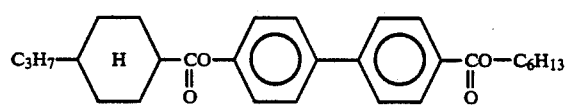 (4-95)
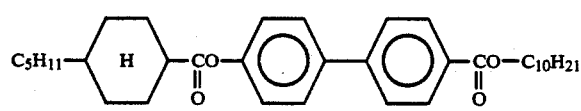 (4-96)
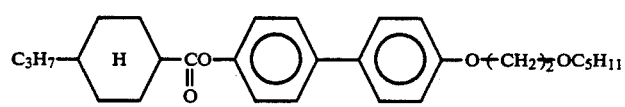 (4-97)
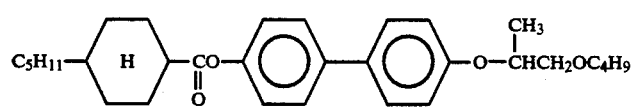 (4-98)
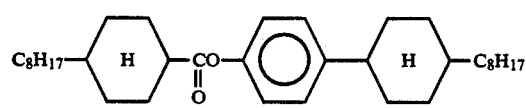 (4-99)
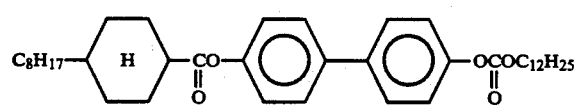 (4-100)
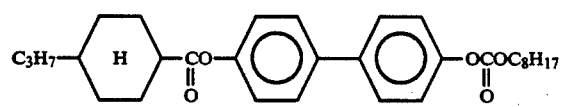 (4-101)
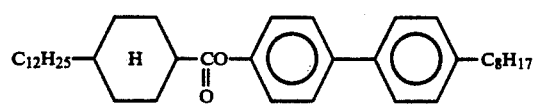 (4-102)
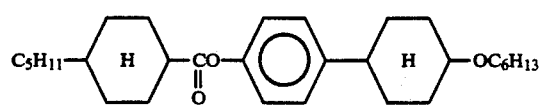 (4-103)

-continued
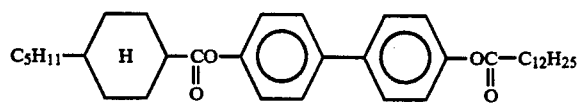 (4-104)
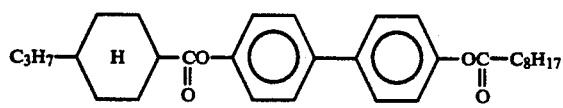 (4-105)
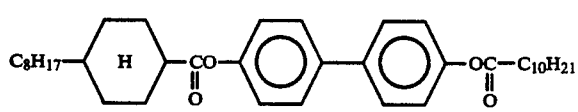 (4-106)
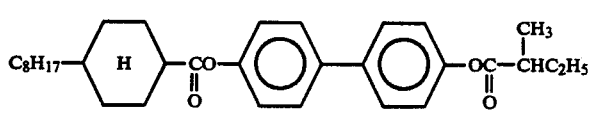 (4-107)
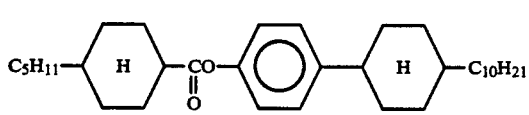 (4-108)
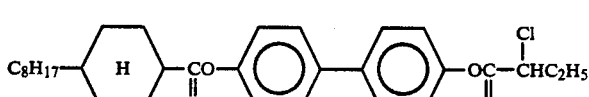 (4-109)
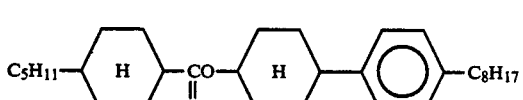 (4-110)
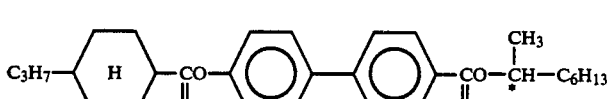 (4-111)
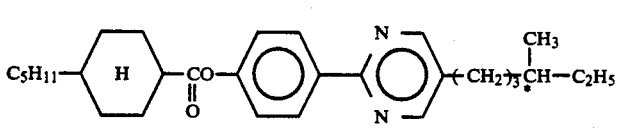 (4-112)
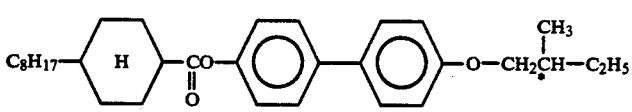 (4-113)
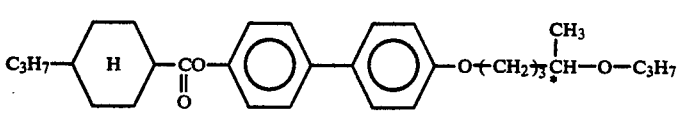 (4-114)
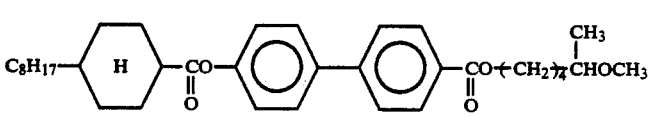 (4-115)
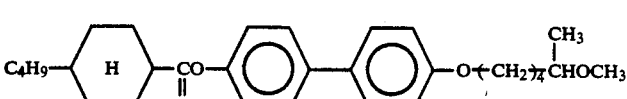 (4-116)

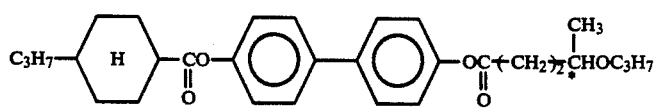 (4-117)
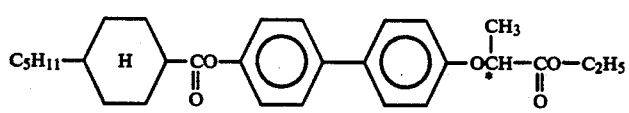 (4-118)
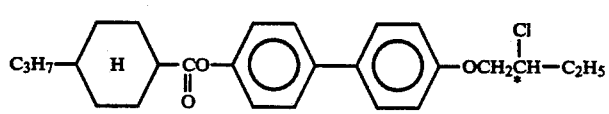 (4-119)
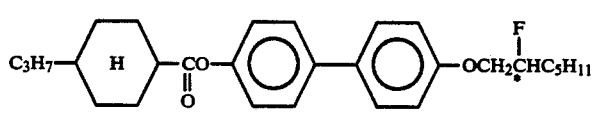 (4-120)
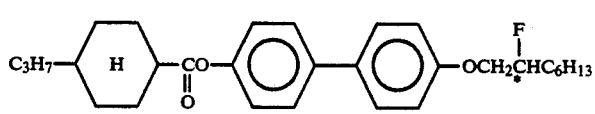 (4-121)
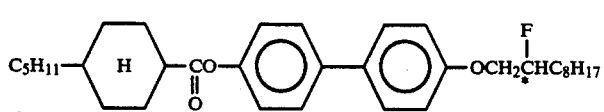 (4-122)
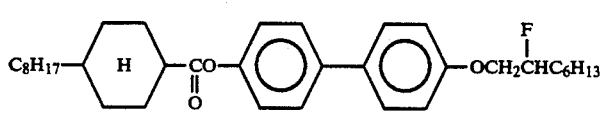 (4-123)
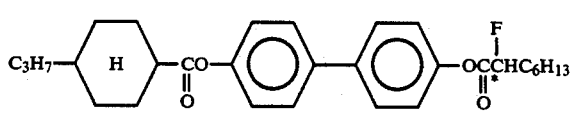 (4-124)
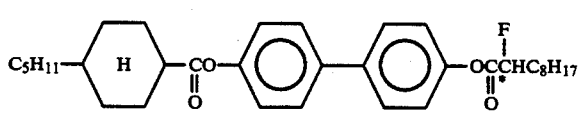 (4-125)
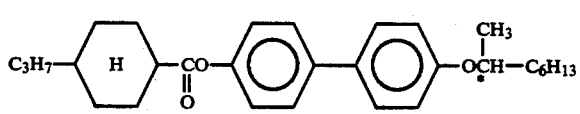 (4-126)
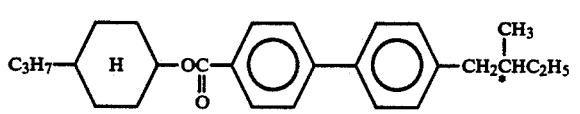 (4-127)
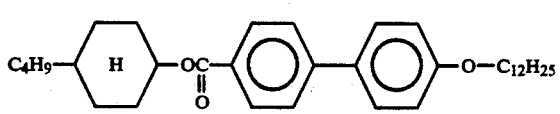 (4-128)
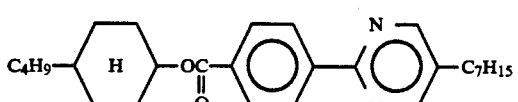 (4-129)

-continued
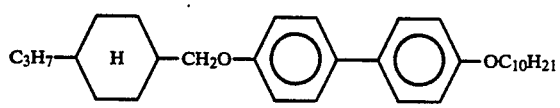 (4-130)
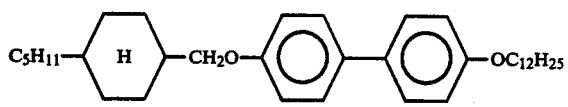 (4-131)
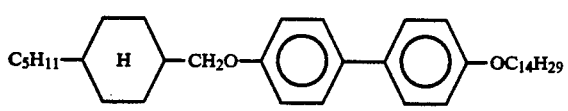 (4-132)
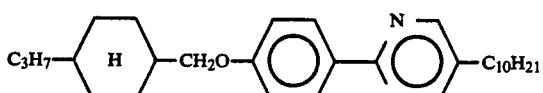 (4-133)
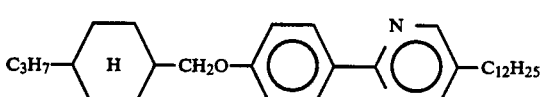 (4-134)
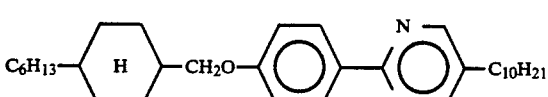 (4-135)
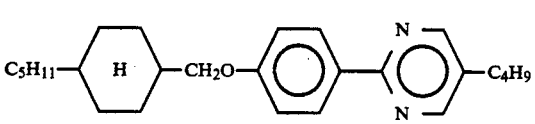 (4-136)
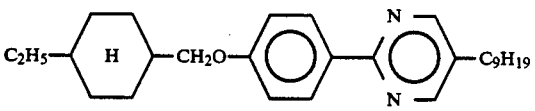 (4-137)
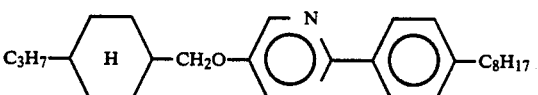 (4-138)
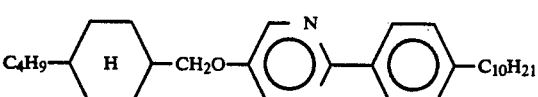 (4-139)
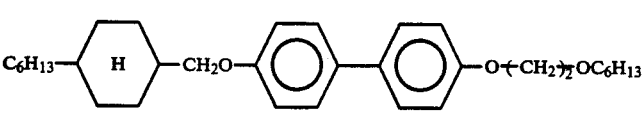 (4-140)
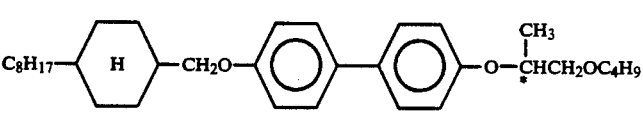 (4-141)
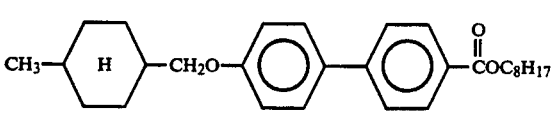 (4-142)

-continued
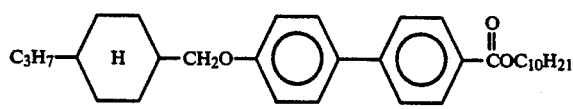 (4-143)
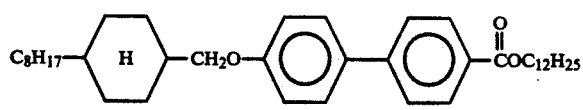 (4-144)
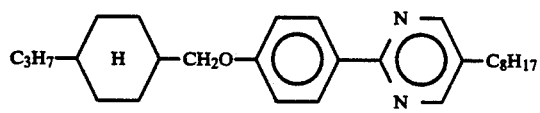 (4-145)
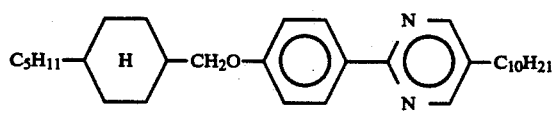 (4-146)
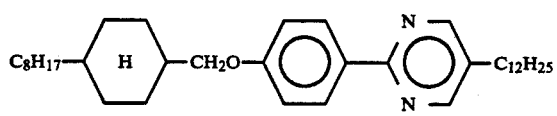 (4-147)
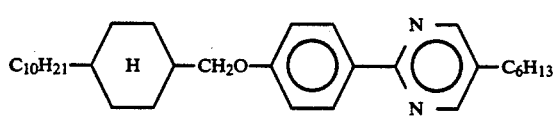 (4-148)
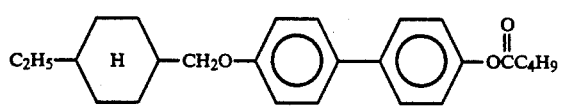 (4-149)
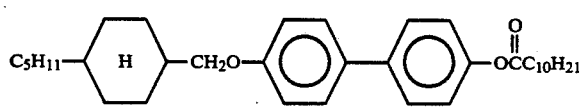 (4-150)
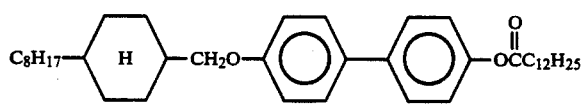 (4-151)
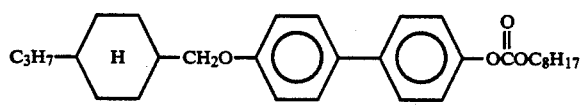 (4-152)
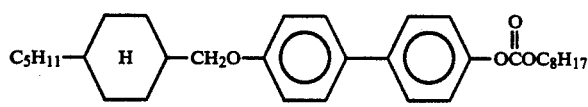 (4-153)
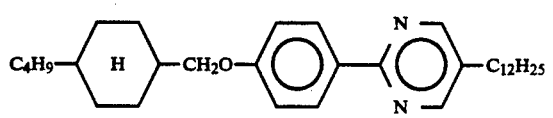 (4-154)
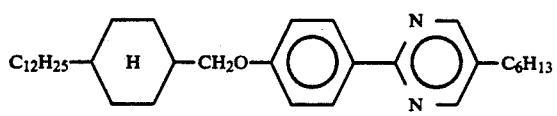 (4-155)

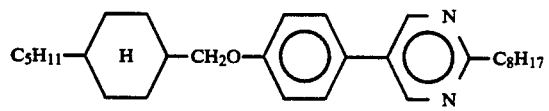 (4-156)
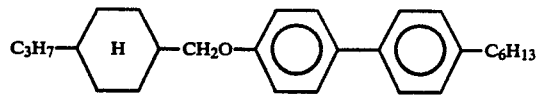 (4-157)
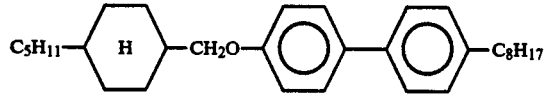 (4-158)
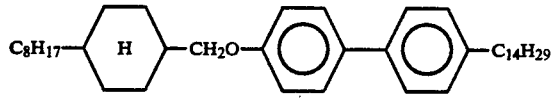 (4-159)
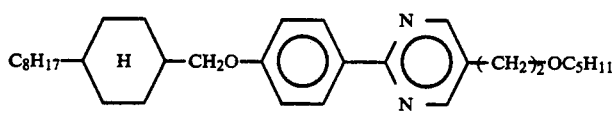 (4-160)
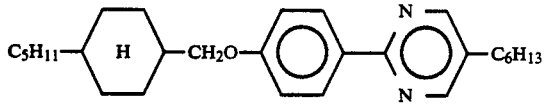 (4-161)
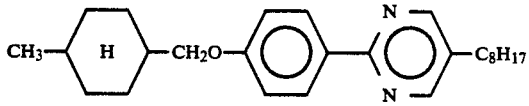 (4-162)
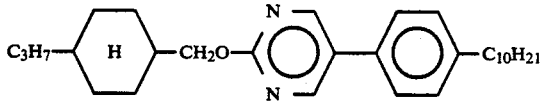 (4-163)
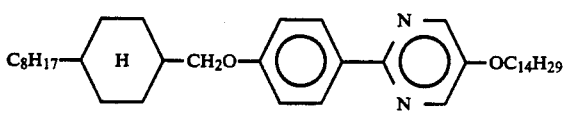 (4-164)
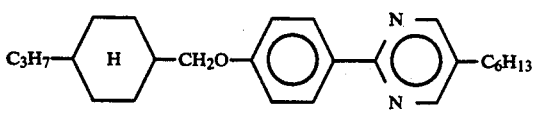 (4-165)
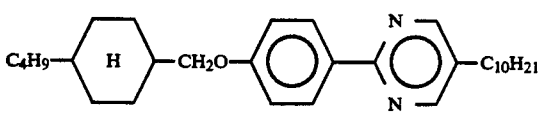 (4-166)
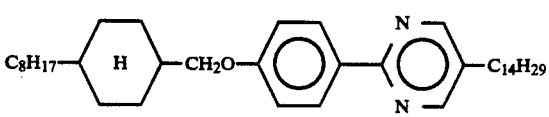 (4-167)
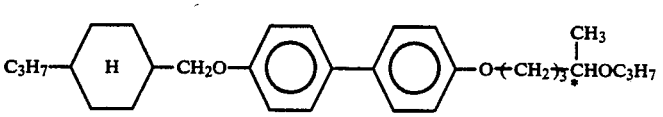 (4-168)

-continued
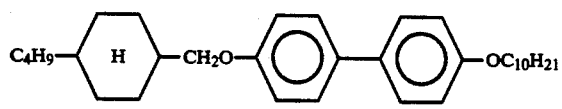 (4-169)
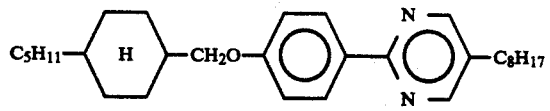 (4-170)
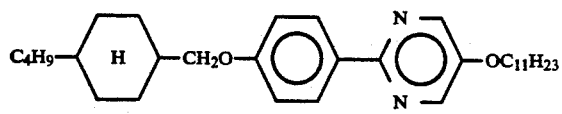 (4-171)
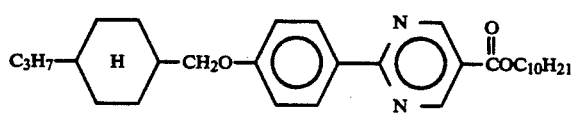 (4-172)
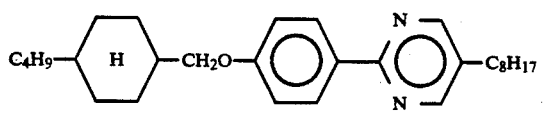 (4-173)
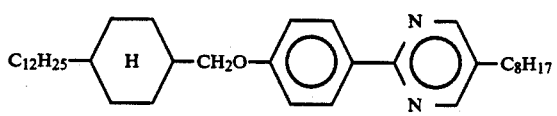 (4-174)
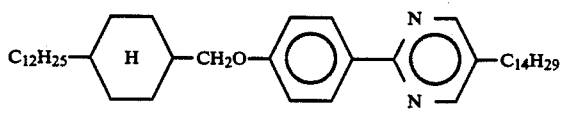 (4-175)
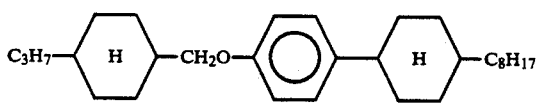 (4-176)
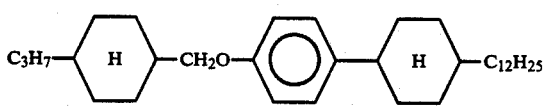 (4-177)
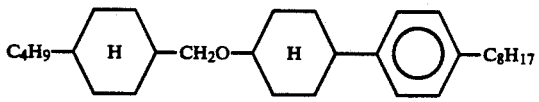 (4-178)
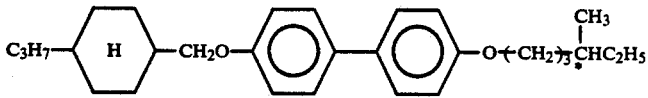 (4-179)
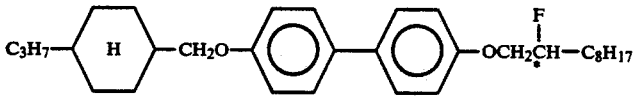 (4-180)
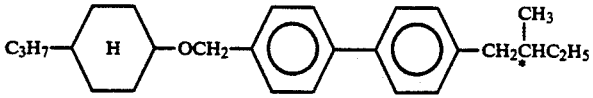 (4-181)

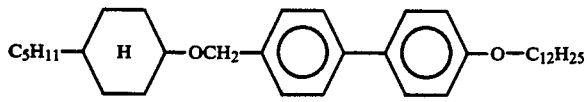

(4-182)

Representative examples of synthesis of the compound represented by the general formula (IV) are shown below.

SYNTHESIS EXAMPLE 5

Synthesis of Compound Example No. 4-4

1.0 g (2.94 mmol) of 5-dodecyl-2-(4'-hydroxyphenyl)-pyrimidine was dissolved in 4 ml of toluene and 4 ml of pyrimidine. To the solution was gradually added dropwise a solution of 0.55 g of trans-4-n-propylcyclohexanecarbonyl chloride (mfd. by Kanto Kagaku K. K.) in 4 ml of toluene below 5° C. on an iced water bath. After the addition, the mixture was stirred for 12 hours at room temperature and then injected into 100 ml of iced water, followed by acidification with 6N-hydrochloric acid, extraction with benzene and successive washing with water, 5 %-sodium bicarbonate aqueous solution and water. After drying with magnesium sulfate, the solvent was distilled off to obtain a cream-colored crude product, which was purified by column chromatography and recrystallized from a solvent mixture of ethanol/ethyl acetate, whereby 0.94 g of a white objective product. (Yield: 64.8 %)

After extraction with isopropyl ether, the organic layer was successively washed with water, aqueous sodium hydroxide solution and water and then dried with magnesium sulfate. After distilling off the solvent, the product was purified by silica gel column chromatography to obtain 3.5 g of trans-4-n-propylcyclohexylmethanol.

(III) 3.4 g (22.4 mmol) of the trans-4-n-propylcyclohexylmethanol was dissolved in 20 ml of pyridine. To the solution was added dropwise 5.3 g of p-toluenesulfonyl chloride dissolved in 20 ml of pyridine while being cooled below 5° C. on an iced water bath. After 10 hours of stirring at room temperature, the reaction mixture was injected into 200 ml of iced water, acidified with 6N-hydrochloric acid aqueous solution and then extracted with isopropyl ether. The organic layer was repeatedly washed with water until the washing liquid became neutral and then dried with magnesium sulfate. After distilling off the solvent, trans-4-propylcyclohexylmethyl-p-toluenesulfonate was obtained.

(IV) 6.3 g (20.2 mmol) of 5-decyl-2-(4'-hydroxyphenyl)pyrimidine was dissolved in 40 ml of dimethyl- Phase transition temperature (°C.):

$$\text{Cryst.} \xrightarrow[61.5]{64.9} \text{Sm3} \xrightarrow[75.4]{76.3} \text{SmC} \xrightarrow[107.4]{108.1} \text{N} \xrightarrow[152.0]{152.8} \text{Iso.}$$

SYNTHESIS EXAMPLE 6

Synthesis of Compound Example No. 4-72

(I) 10 g (53.6 mmol) of trans-4-n-propylcyclohexanecarbonyl chloride was dissolved in 30 ml of ethanol, and a small amount of triethylamine was added thereto, followed by 10 hours of stirring at room temperature. The reaction mixture was injected into 100 ml of iced water, acidified with 6N-hydrochloric acid aqueous solution and extracted with isopropyl ether. The organic layer was repeatedly washed with water until the washing liquid became neutral and then dried with magnesium sulfate. After distilling off the solvent, the product was purified by silica gel column chromatography to obtain 9.9 g of trans-4-n-propylcyclohexanecarboxylic acid-ethyl-ester.

(II) 0.73 g (19.1 mmol) of aluminum lithium hydride was added to 30 ml of dry ether and subjected to 1 hour of heat-refluxing. After cooling to about 10° C. on an iced water bath, a solution of 5 g (25.5 mmol) of the trans-4-n-propylcyclohexanecarboxylic acid-ethyl-ester was gradually added dropwise thereto. After the addition, the mixture was stirred for 1 hour at room temperature and heat-refluxed for 1 hour. The product was treated with ethyl acetate and 6N-hydrochloric acid aqueous solution and then injected into 200 ml of iced water.

formamide, and 1.5 g of 85 %-potassium hydroxide was added thereto, followed by 1 hour of stirring at 100° C. to the mixture was further added 6.9 g of trans-4-n-propylcyclohexylmethyl-p-toluenesulfonate, followed by 4 hours of stirring at 100° C. After the reaction, the reaction product was injected into 200 ml of iced water and extracted with benzene. The organic layer was washed with water and dried with magnesium sulfate. After distilling off the solvent, the product was purified by silica gel column chromatography and recrystallized from an ethanol/ethyl acetate mixture solvent to obtain the above-mentioned Example Compound No. 4-72.

IR (cm$^{-1}$): 2920, 2840, 1608, 1584, 1428, 1258, 1164, 800

Phase transition temperature (°C.)

$$\text{Cryst.} \xrightarrow[62.9]{82.0} \text{Sm2} \xrightarrow[86.8]{91.3} \text{SmC} \xrightarrow[97.8]{98.6} \text{N} \xrightarrow[136.8]{137.6} \text{Iso.}$$

wherein Sm2 denotes a smectic phase (un-identified) other than SmA and SmC.

Further, in case where Z$_2$ is a single bond, the compound, for example, represented by the following formula:

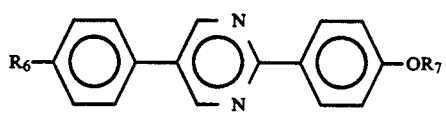

may be synthesized along the following reaction scheme.

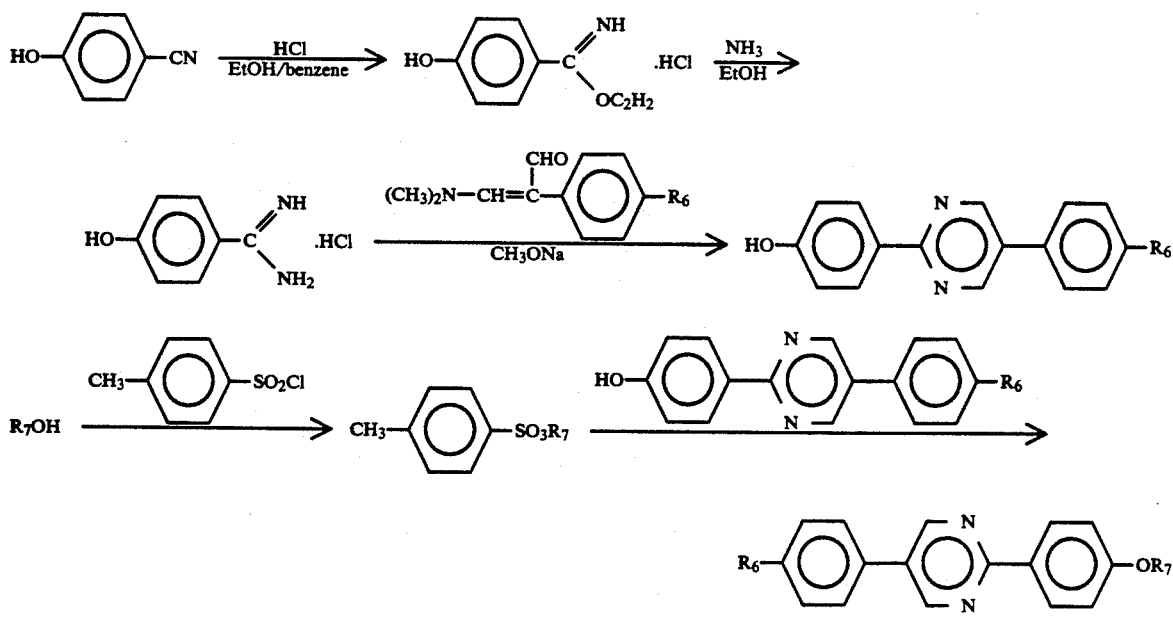

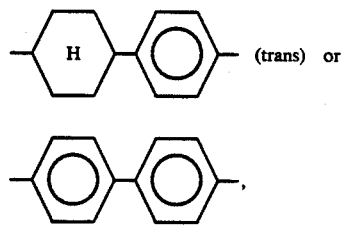

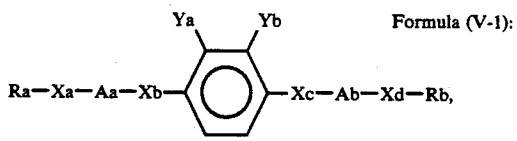

In a preferred embodiment, the ferroelectric chiral smectic liquid crystal composition according to the present invention further comprises a mesomorphic compound having a negative dielectric anisotropy, which is preferably selected from those represented by the following formulas (V-1) to (V-5):

Formula (V-1):

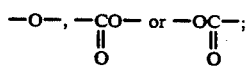

wherein Ra and Rb respectively denote a linear or branched alkyl group capable of having a substituent; Xa and Xd respectively denote a single bond $-O-$, $-\underset{\underset{O}{\|}}{C}O-$ or $-O\underset{\underset{O}{\|}}{C}-$;

Xb and Xc respectively denote a single bond, $-\underset{\underset{O}{\|}}{C}O-$, $-O\underset{\underset{O}{\|}}{C}-$ or $-CH_2CH_2-$;

Aa and Ab respectively denote a single bond,

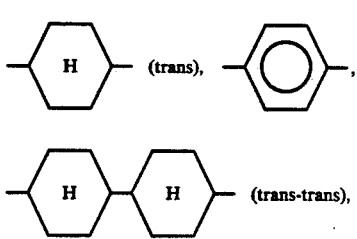

-continued

 (trans) or

with proviso that when Aa and Ab are both single bonds, Xb and Xc are both single bonds, and Xa and Xd are both single bonds or —O—, or Xa is $-\underset{\underset{O}{\|}}{C}O-$ and Xd is $-O\underset{\underset{O}{\|}}{C}-$;

and Ya and Yb are respectively cyano group, halogen or hydrogen with proviso that Ya and Yb cannot be hydrogen simultaneously;

Formula (V-2):

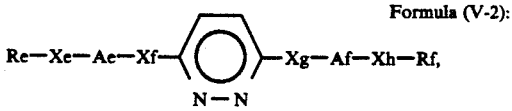

wherein Re and Rf respectively denote a linear or branched alkyl group capable of having a substituent; Xe and Xh are respectively a single bond, $-O-$, $-\underset{\underset{O}{\|}}{C}O-$ or $-O\underset{\underset{O}{\|}}{C}-$;

Xf and Xg are respectively $$-\underset{\underset{O}{\|}}{C}O-, \quad -O\underset{\underset{O}{\|}}{C}-$$

or a single bond; and Ae and Af are respectively

[phenyl ring], [cyclohexyl ring with H]

or a single bond with proviso that Ae and Af cannot be a single bond simultaneously;

Formula (V-3):

$$Ri-Xi-Ai-\underset{Z_3}{\overset{N-N}{\diagdown\diagup}}-\!\!\!\!\!\!\!\!\!\!\!\!\!\!\!\!\!\!\!\!\!\!\!\!\bigcirc\!\!\!\!\!\!\!-Xj-Aj-Xk-Rj,$$

wherein Ai is a single bond or

[phenyl ring];

Aj is a single bond,

[cyclohexyl with H] or [phenyl];

Ri and Rj are respectively a linear or branched alkyl group capable of having a substituent with proviso that Ri and Rj are linear alkyl groups when Aj is a single bond; $Z_3$ is —O— or —S—; Xi and Xk are respectively a single bond, $$-O-, \quad -\underset{\underset{O}{\|}}{C}O-, \quad -O\underset{\underset{O}{\|}}{C}- \text{ or } -O\underset{\underset{O}{\|}}{C}O-;$$

Xj is a single bond, $$-\underset{\underset{O}{\|}}{C}O-, \quad -O\underset{\underset{O}{\|}}{C}-, \quad -CH_2O- \text{ or } -OCH_2-$$

proviso that Xi is a single bond when Ai is a bond, Xj is not a single bond when Aj is

[cyclohexyl with H] or [phenyl], and Xk is a single bond when Aj is a single bond;

Formula (V-4):

$$Rl-Xl-Al-Xm-Am-\overset{CN}{\underset{}{\diagup\!\!\!\!\!\bigcirc\!\!\!\!\!\diagdown}}-Rm,$$

wherein Rl and Rm are respectively a linear or branched alkyl group capable of having a substituent; Al and Am are respectively a single bond,

[cyclohexyl with H] or [phenyl]

with proviso that Al and Am cannot be a single bond simultaneously; Xl is a single bond, $$-O-, \quad -\underset{\underset{O}{\|}}{C}O- \text{ or } -O\underset{\underset{O}{\|}}{C}-;$$

and Xm is a single bond, $$-\underset{\underset{O}{\|}}{C}O-, \quad -O\underset{\underset{O}{\|}}{C}-, \quad -CH_2O-, \quad -OCH_2-,$$

$-CH_2CH_2-$ or $-C\equiv C-$;

Formula (V-5):

$$Rn-Xn-An-Xo-\!\!\!\!\!\!\!\!\!\!\!\!\!\bigcirc\!\!\!\!\!\!\!\!-Z_4-Ao-Xp-Ap-Xq-Ro,$$

wherein Rn and Ro are respectively a linear or branched alkyl group capable of having a substituent; Xn and Xq are respectively a single bond, $$-O-, \quad -\underset{\underset{O}{\|}}{C}O- \text{ or } -O\underset{\underset{O}{\|}}{C}-;$$

Xo and Xp are respectively a single bond, $$-\underset{\underset{O}{\|}}{C}O-, \quad -O\underset{\underset{O}{\|}}{C}-, \quad -CH_2O-,$$

$-OCH_2-$ or $-CH_2CH_2-$; An and Ap are respectively a single bond,

[cyclohexyl with H] or [phenyl],

Ao is

[phenyl] or [cyclohexyl with H];

and $Z_4$ is $$-\underset{\underset{}{}}{\overset{CN}{C}}=CH- \text{ or } -\underset{\underset{}{}}{\overset{CN}{C}H}-CH_2-.$$

In the above formulas (V-1) to (V-5), the alkyl groups Ra - Ro may respectively have 1-18 carbon atoms, preferably 4-16 carbon atoms, further preferably 6-12 carbon atoms.

Specific examples of mesomorphic compounds represented by the general formulas (V-1) to (V-5) may respectively include those denoted by the structural formulas shown below.
Formula (V-1)
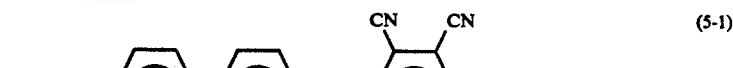
(5-1)
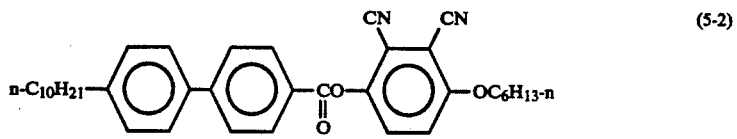
(5-2)
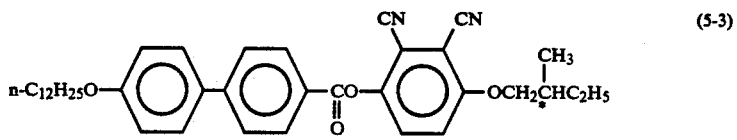
(5-3)
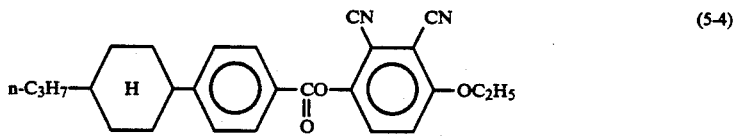
(5-4)
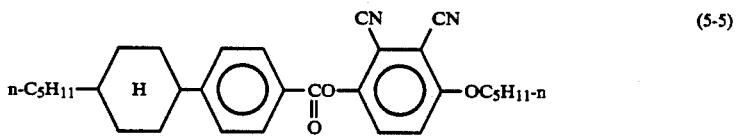
(5-5)
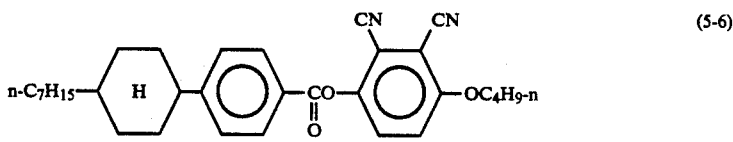
(5-6)
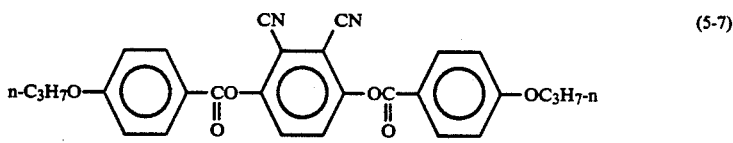
(5-7)
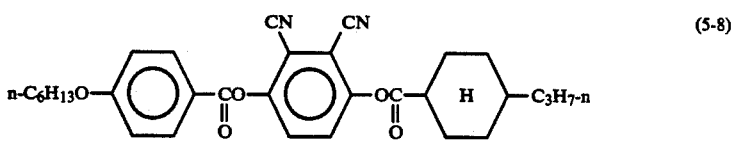
(5-8)
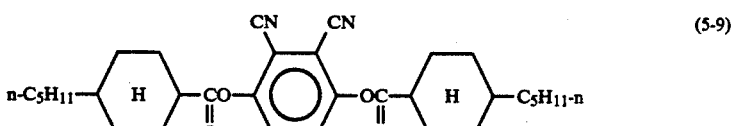
(5-9)
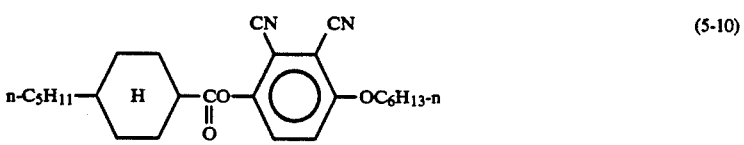
(5-10)

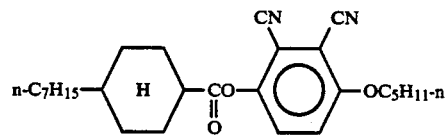 (5-11)
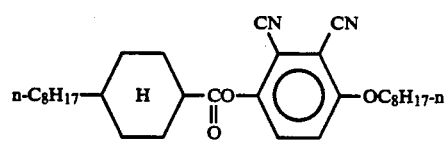 (5-12)
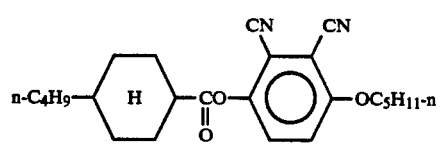 (5-13)
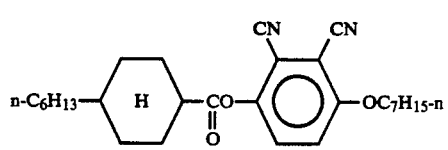 (5-14)
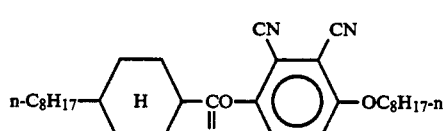 (5-15)
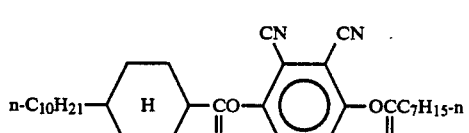 (5-16)
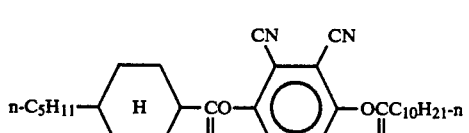 (5-17)
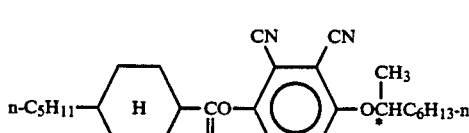 (5-18)
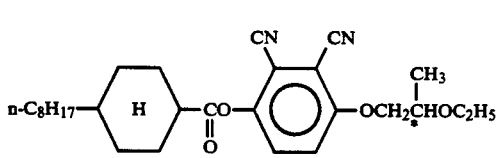 (5-19)
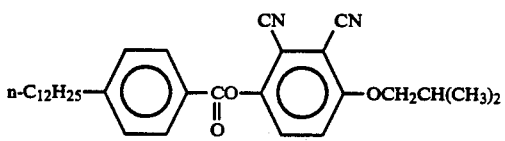 (5-20)
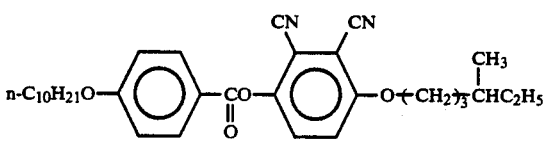 (5-21)

-continued
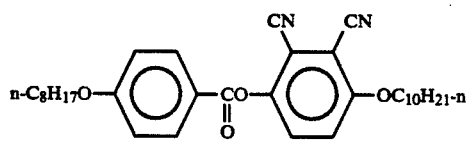 (5-22)
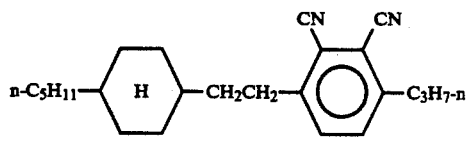 (5-23)
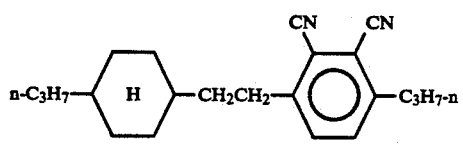 (5-24)
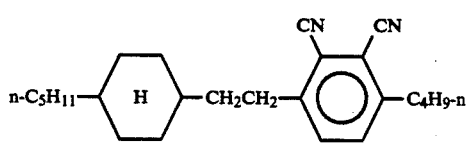 (5-25)
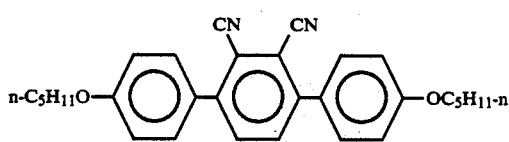 (5-26)
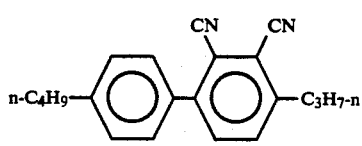 (5-27)
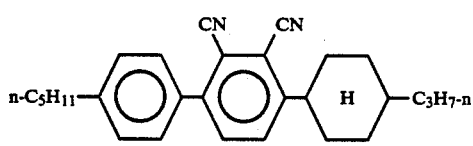 (5-28)
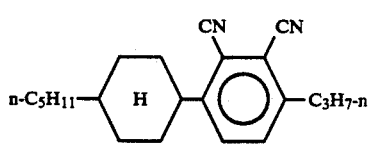 (5-29)
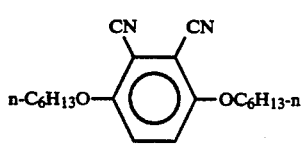 (5-30)
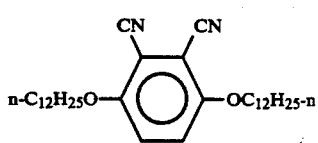 (5-31)
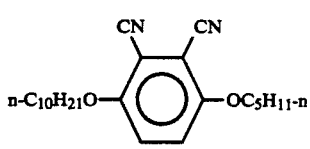 (5-32)

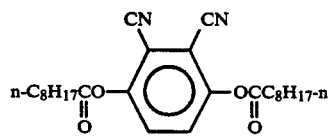 (5-33)
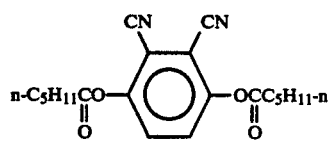 (5-34)
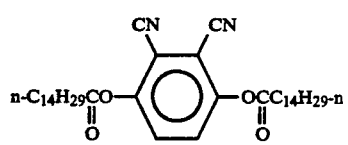 (5-35)
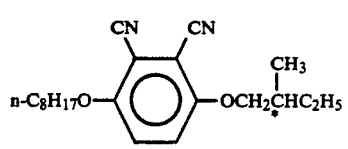 (5-36)
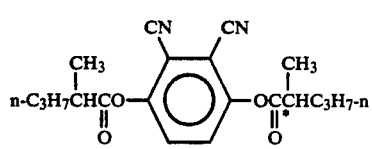 (5-37)
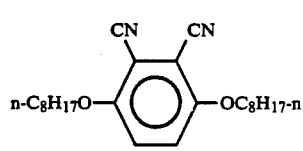 (5-38)
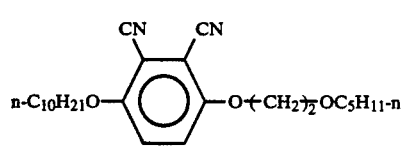 (5-39)
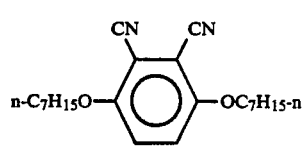 (5-40)
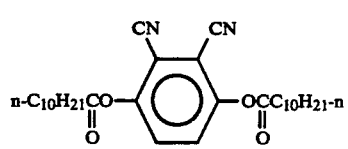 (5-41)
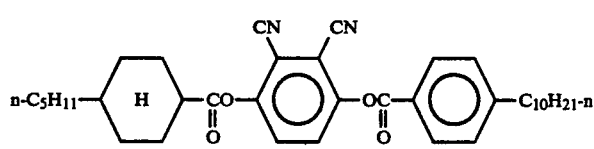 (5-42)
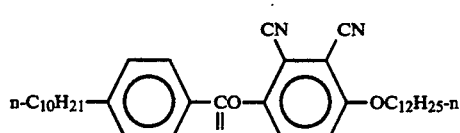 (5-43)

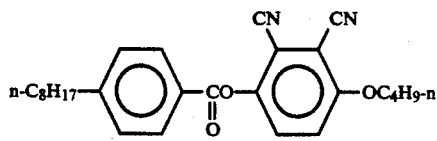 (5-44)
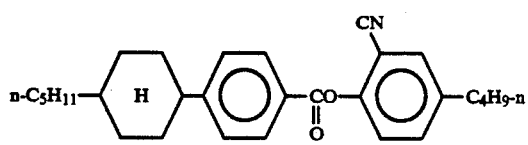 (5-45)
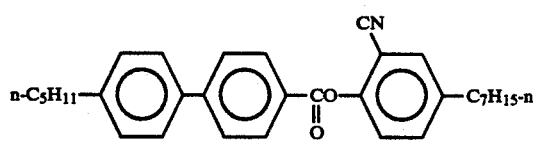 (5-46)
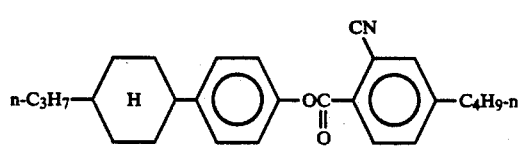 (5-47)
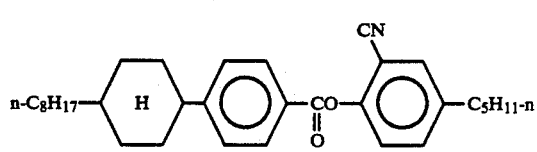 (5-48)
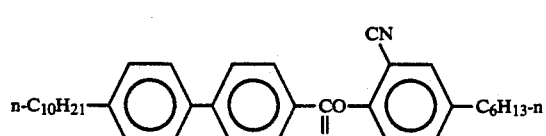 (5-49)
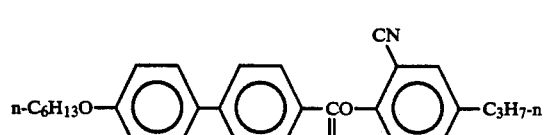 (5-50)
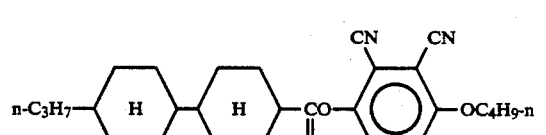 (5-51)
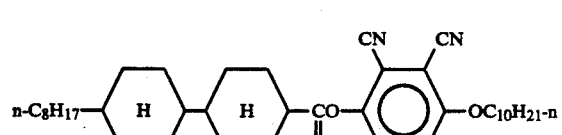 (5-52)
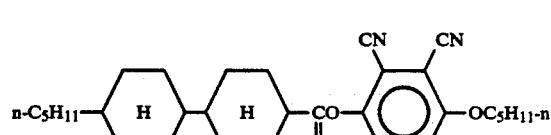 (5-53)
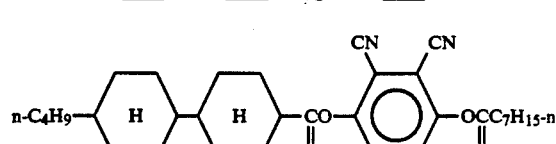 (5-54)

-continued
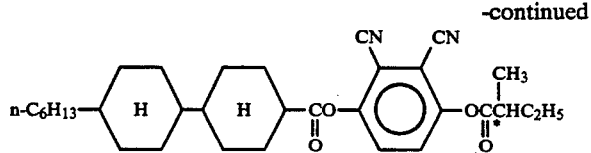 (5-55)
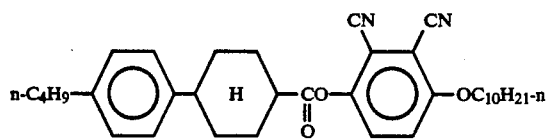 (5-56)
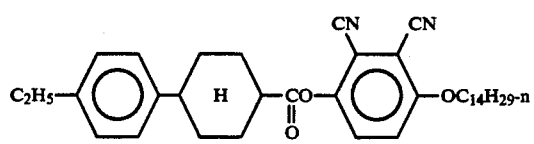 (5-57)
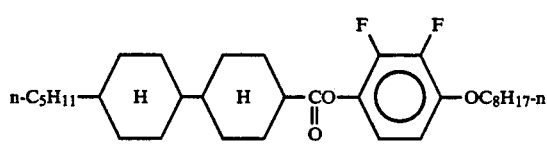 (5-58)
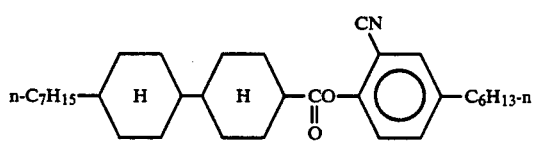 (5-59)
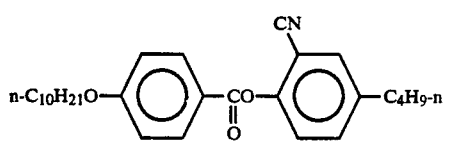 (5-60)
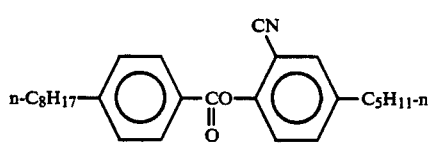 (5-61)
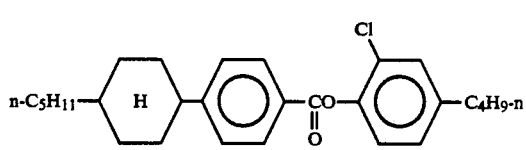 (5-62)
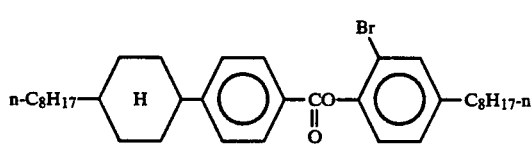 (5-63)
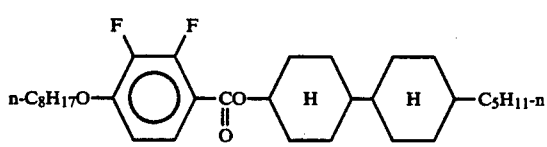 (5-64)
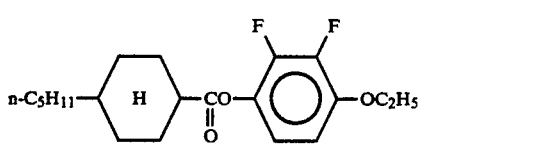 (5-65)

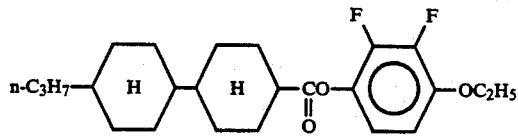 (5-66)
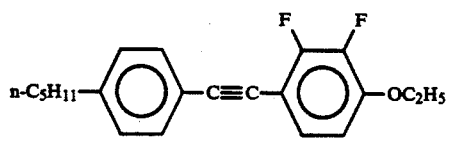 (5-67)
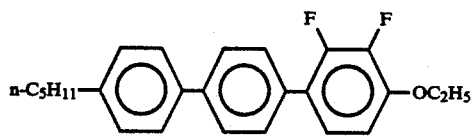 (5-68)
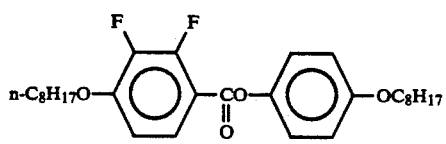 (5-69)
Formula (V-2)
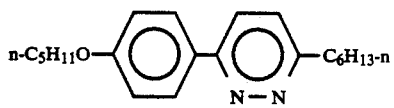 (5-70)
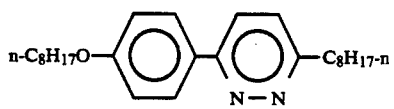 (5-71)
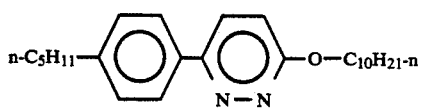 (5-72)
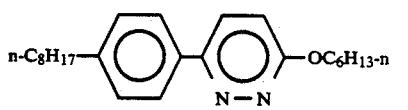 (5-73)
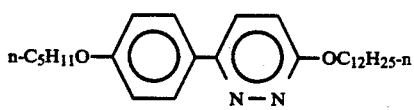 (5-74)
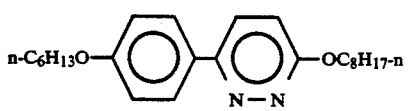 (5-75)
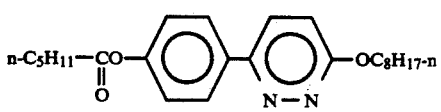 (5-76)
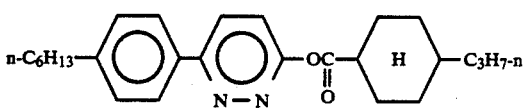 (5-77)

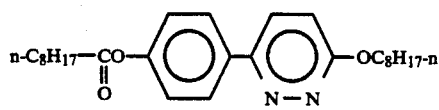 (5-78)
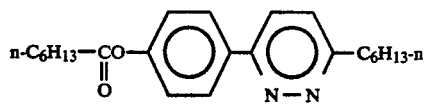 (5-79)
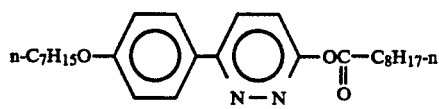 (5-80)
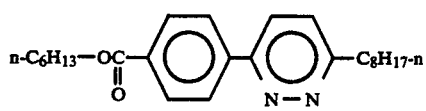 (5-81)
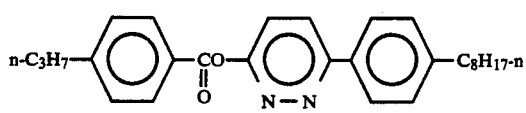 (5-82)
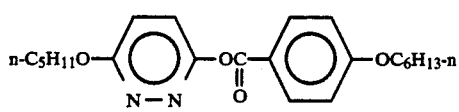 (5-83)
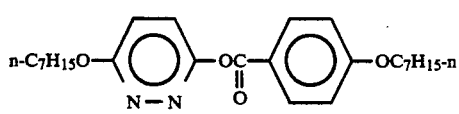 (5-84)
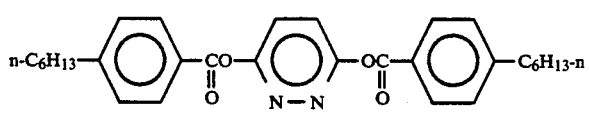 (5-85)
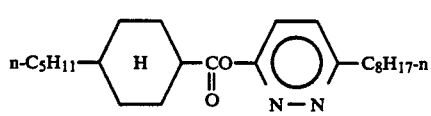 (5-86)
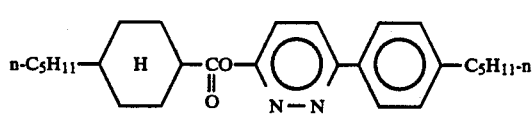 (5-87)
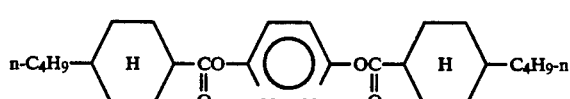 (5-88)
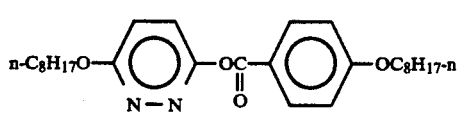 (5-89)
Formula (V-3)
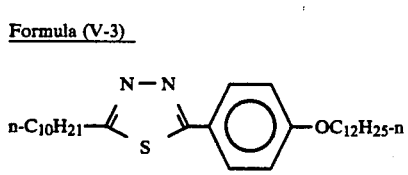 (5-90)

-continued
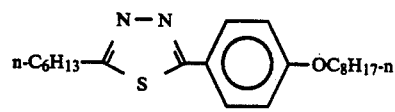 (5-91)
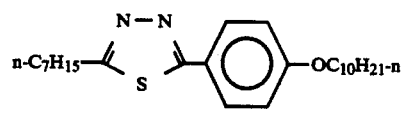 (5-92)
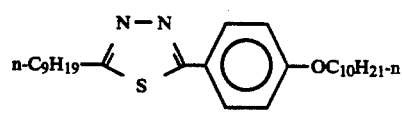 (5-93)
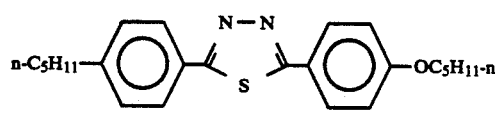 (5-94)
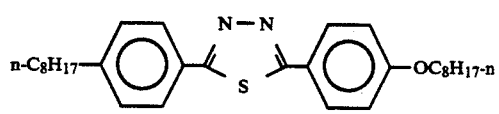 (5-95)
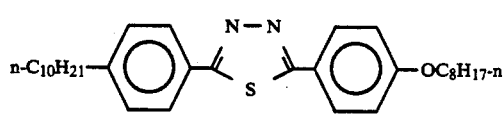 (5-96)
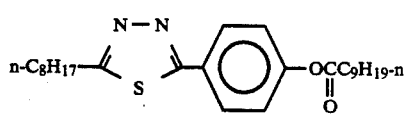 (5-97)
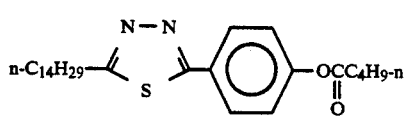 (5-98)
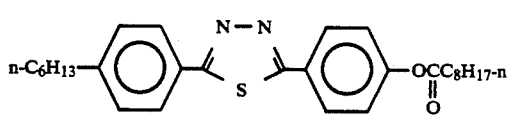 (5-99)
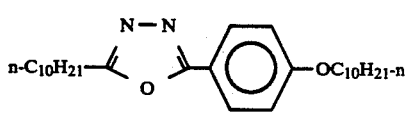 (5-100)
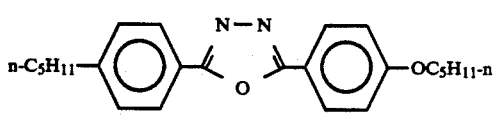 (5-101)
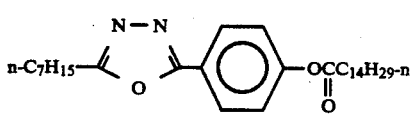 (5-102)
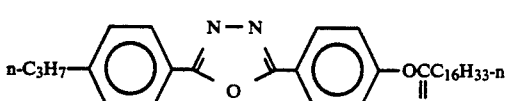 (5-103)

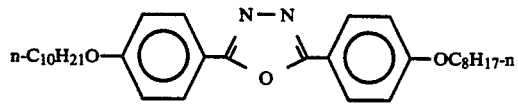 (5-104)
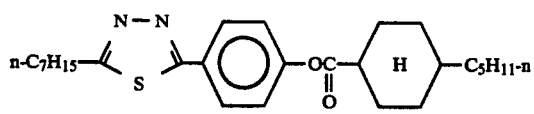 (5-105)
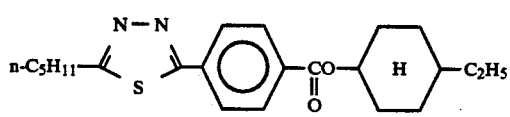 (5-106)
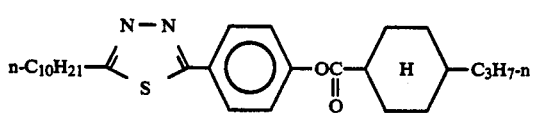 (5-107)
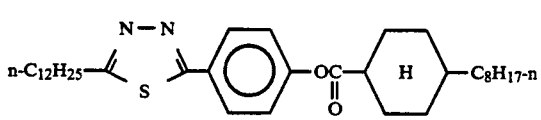 (5-108)
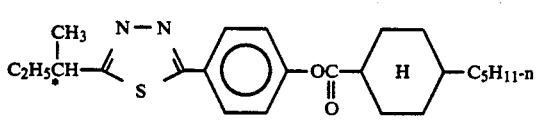 (5-109)
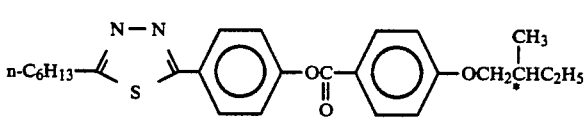 (5-110)
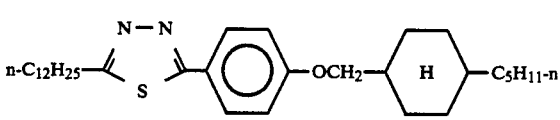 (5-111)
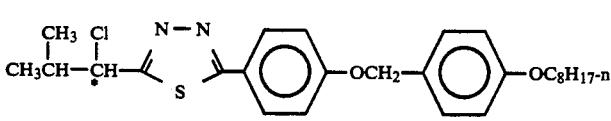 (5-112)
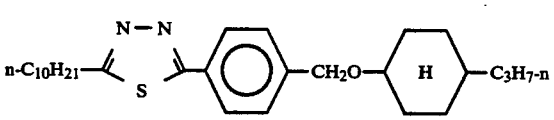 (5-113)
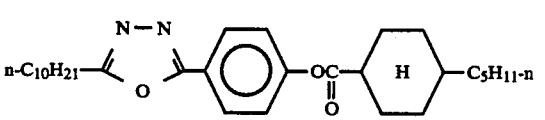 (5-114)
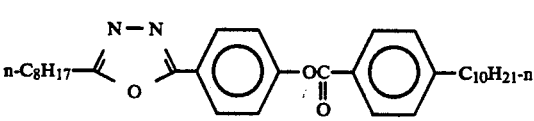 (5-115)
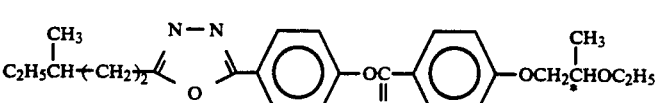 (5-116)

-continued
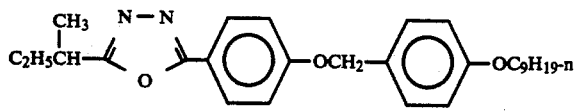 (5-117)
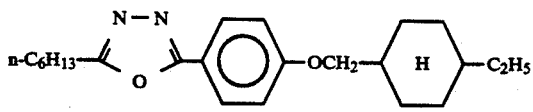 (5-118)
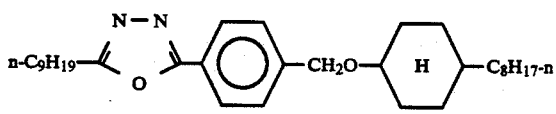 (5-119)
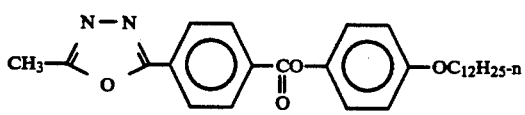 (5-120)
Formula (V-4)
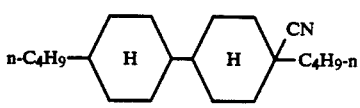 (5-121)
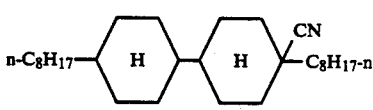 (5-122)
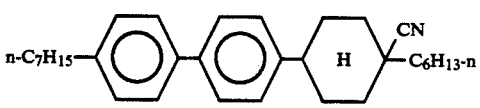 (5-123)
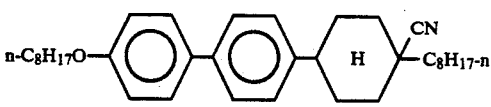 (5-124)
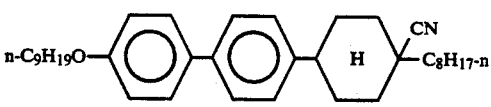 (5-125)
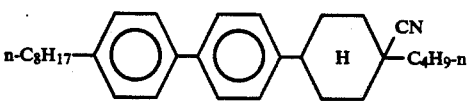 (5-126)
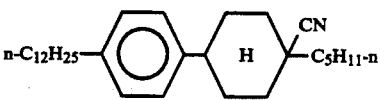 (5-127)
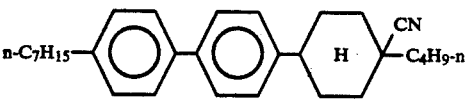 (5-128)
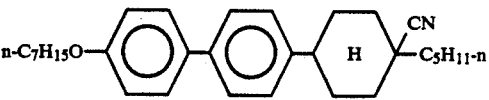 (5-129)

n-C₇H₁₅O—⟨Ph⟩—C≡C—⟨Ph⟩—⟨H⟩(CN)—C₅H₁₁-n  (5-130)

n-C₆H₁₃OC(O)—⟨Ph⟩—⟨Ph⟩—⟨H⟩(CN)—C₈H₁₇-n  (5-131)

n-C₁₀H₂₁—⟨Ph⟩—⟨Ph⟩—OC(O)—⟨H⟩(CN)—C₇H₁₅-n  (5-132)

n-C₁₂H₂₅O—⟨Ph⟩—⟨Ph⟩—OC(O)—⟨H⟩(CN)—C₄H₉-n  (5-133)

n-C₁₀H₂₁O—⟨Ph⟩—OC(O)—⟨H⟩(CN)—C₇H₁₅-n  (5-134)

n-C₇H₁₅—⟨Ph⟩—C(O)O—⟨Ph⟩—⟨H⟩(CN)—C₇H₁₅-n  (5-135)

n-C₅H₁₁O—⟨Ph⟩—C(O)O—⟨Ph⟩—⟨H⟩(CN)—C₄H₉-n  (5-136)

n-C₃H₇—⟨H⟩—C(O)O—⟨Ph⟩—⟨H⟩(CN)—C₅H₁₁-n  (5-137)

n-C₈H₁₇O—⟨Ph⟩—C(O)O—⟨Ph⟩—⟨H⟩(CN)—C₈H₁₇-n  (5-138)

n-C₇H₁₅O—⟨Ph⟩—CH₂O—⟨Ph⟩—⟨H⟩(CN)—C₇H₁₅-n  (5-139)

n-C₅H₁₁—⟨H⟩—CH₂O—⟨Ph⟩—⟨H⟩(CN)—C₈H₁₇-n  (5-140)

n-C₆H₁₃O—⟨Ph⟩—CH₂CH₂—⟨Ph⟩—⟨H⟩(CN)—C₇H₁₅-n  (5-141)

n-C₇H₁₅O—⟨Ph⟩—CH₂CH₂—⟨Ph⟩—⟨H⟩(CN)—C₅H₁₁-n  (5-142)

n-C₈H₁₇—⟨H⟩—C(O)O—⟨Ph⟩—OC(O)—⟨H⟩(CN)—C₈H₁₇-n  (5-143)

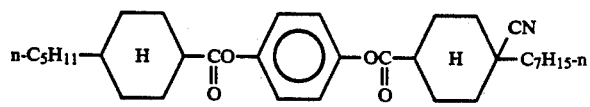 (5-144)
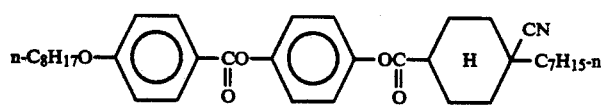 (5-145)
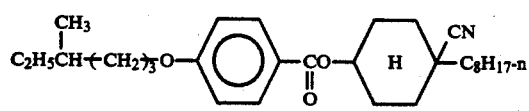 (5-146)
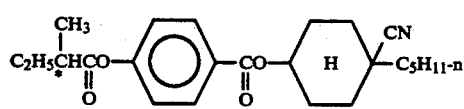 (5-147)
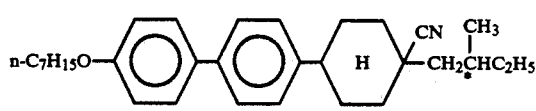 (5-148)
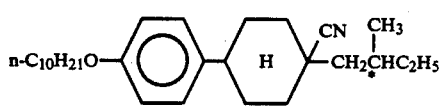 (5-149)
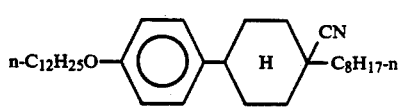 (5-150)
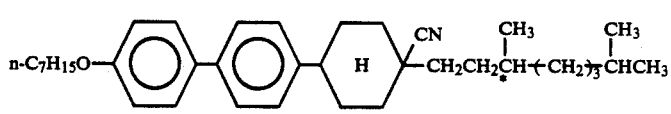 (5-151)
Formula (V-5)
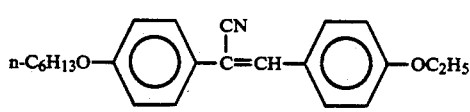 (5-152)
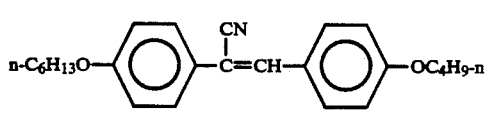 (5-153)
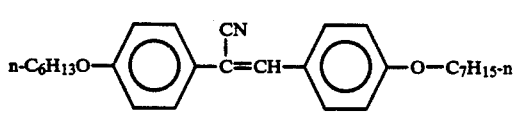 (5-154)
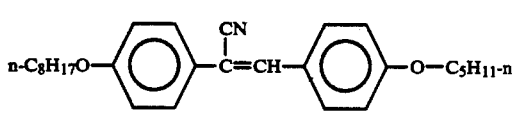 (5-155)
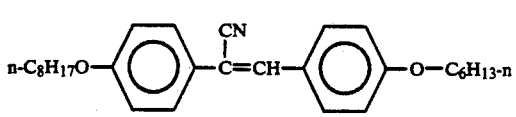 (5-156)

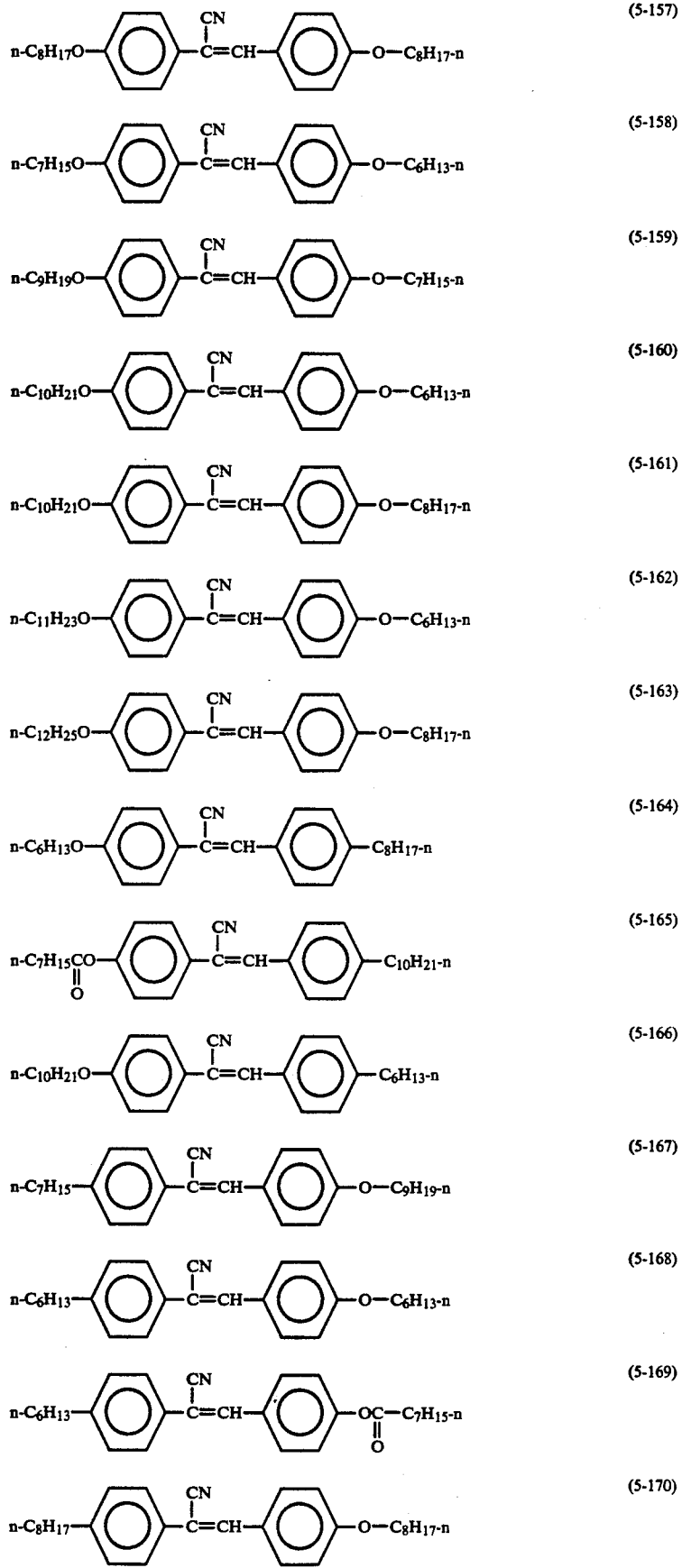

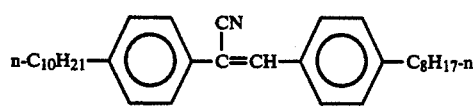 (5-171)
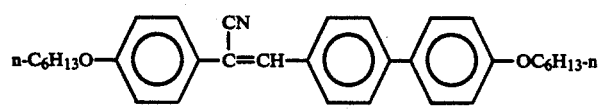 (5-172)
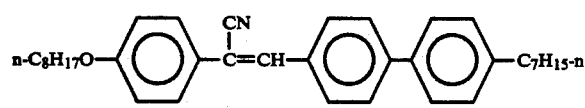 (5-173)
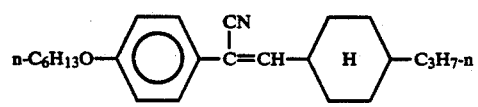 (5-174)
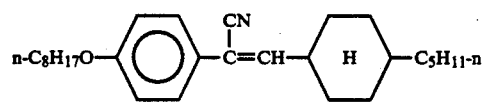 (5-175)
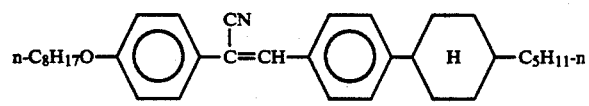 (5-176)
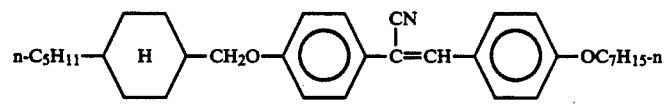 (5-177)
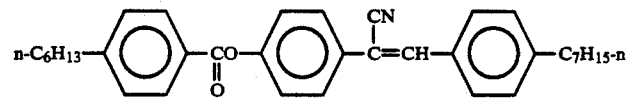 (5-178)
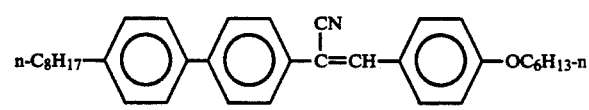 (5-179)
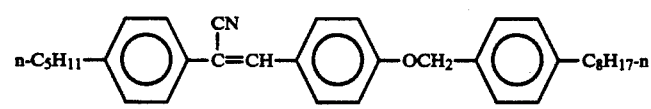 (5-180)
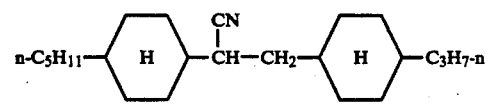 (5-181)
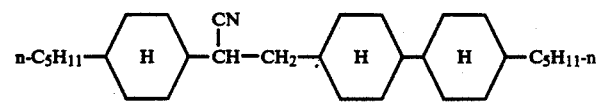 (5-182)
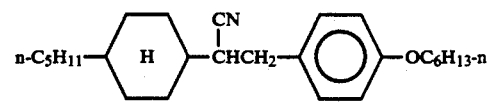 (5-183)

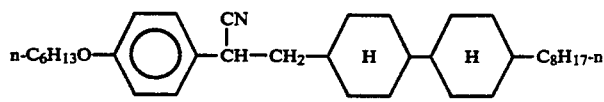
(5-184)

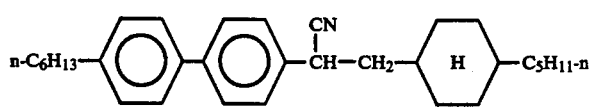
(5-185)

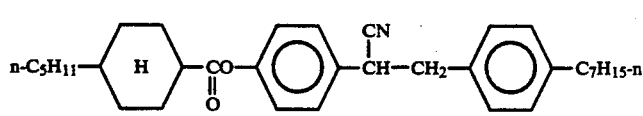
(5-186)

The mesomorphic compound having a negative dielectric anisotropy $\Delta\epsilon$ may preferably have $\Delta\epsilon<-2$, preferably $\Delta\epsilon<-5$, further preferably $\Delta\epsilon<-10$.

The liquid crystal composition according to the present invention may be obtained by mixing at least one species of the compound represented by the formula (II), at least one species of the compound represented by the formula (III), at least one species of the compound represented by any of the formulas (I) and (IV), optionally at least one species of a mesomorphic compound having a negative dielectric anisotropy, and another mesomorphic compound in appropriate proportions. The compounds of the formulas (I) and (IV) can be used in combination. The liquid crystal composition according to the present invention may preferably be formulated as a ferroelectric liquid crystal composition, particularly a ferroelectric chiral smectic liquid crystal composition.

Specific examples of another mesomorphic compound as described above may include those denoted by the following structure formulas.

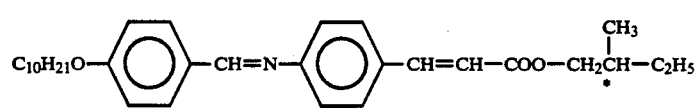
(1)

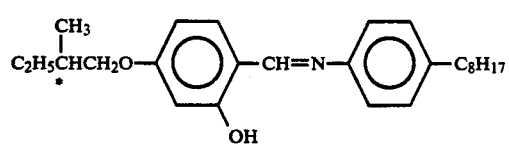
(2)

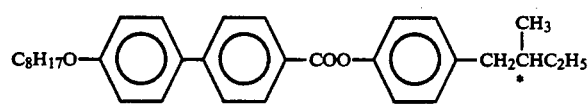
(3)

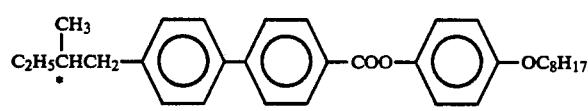
(4)

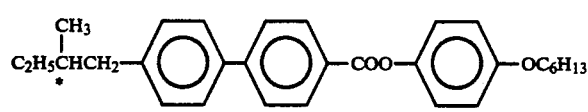
(5)

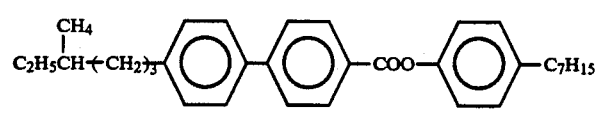
(6)

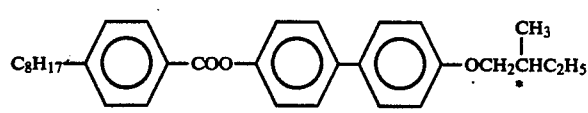
(7)

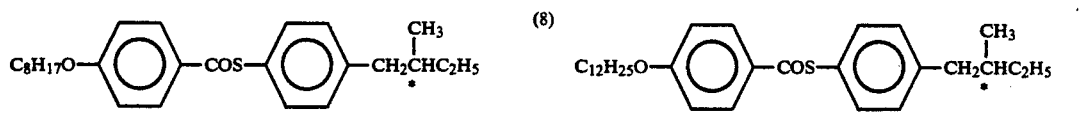
(8)

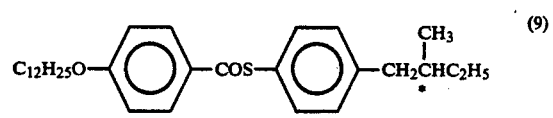
(9)

-continued
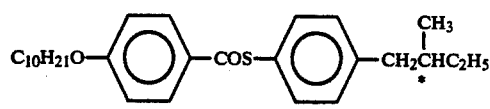 (10)
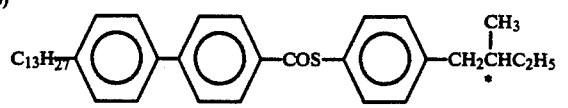 (11)
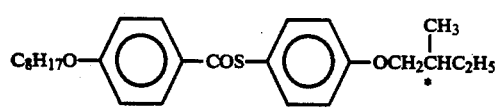 (12)
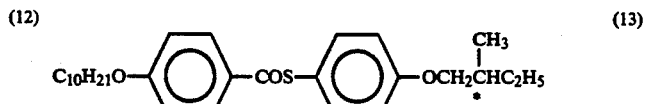 (13)
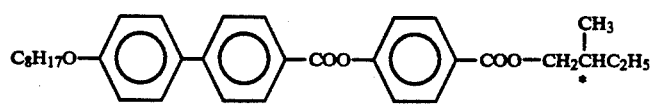 (14)
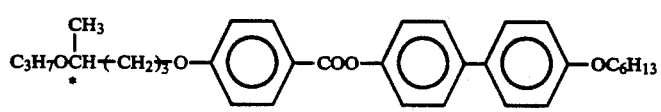 (15)
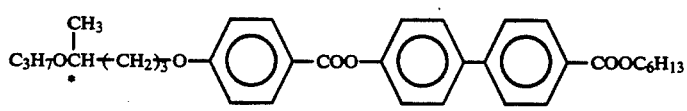 (16)
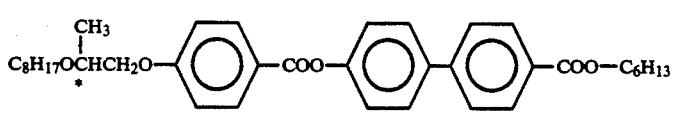 (17)
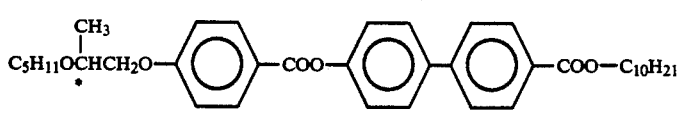 (18)
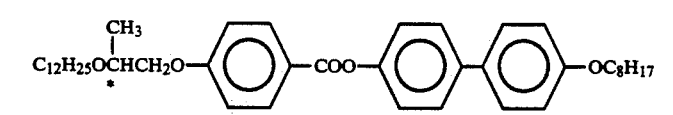 (19)
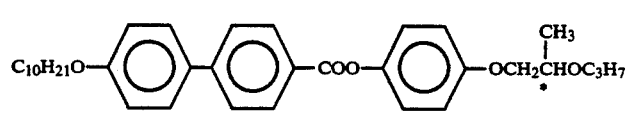 (20)
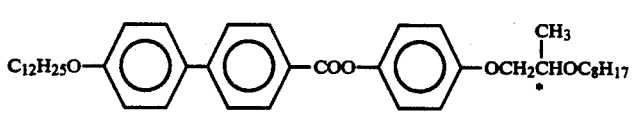 (21)
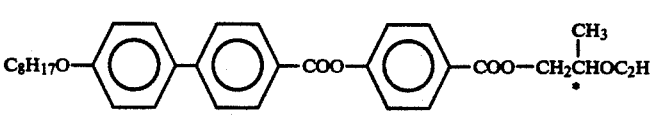 (22)
(23)
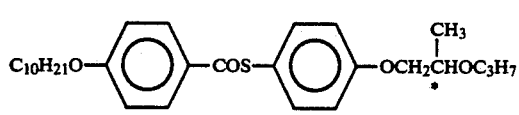 (24)
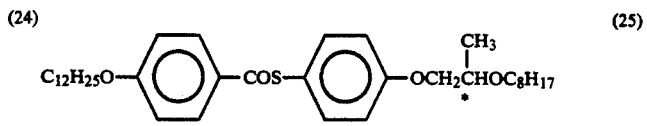 (25)

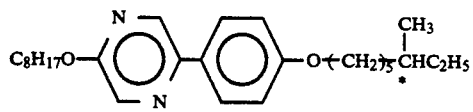 (26)
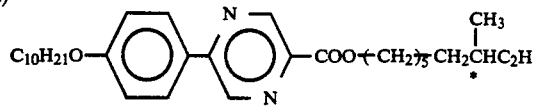 (27)
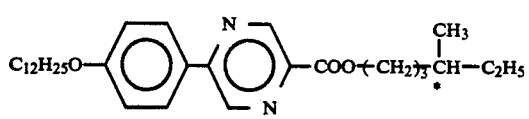 (28)
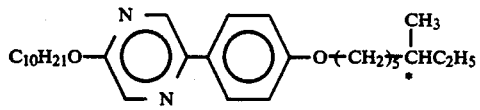 (29)
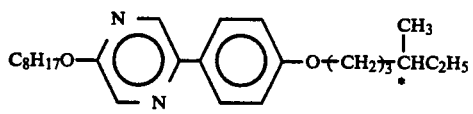 (30)
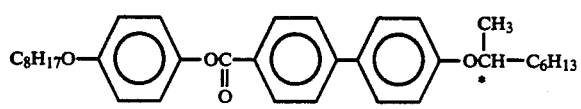 (31)
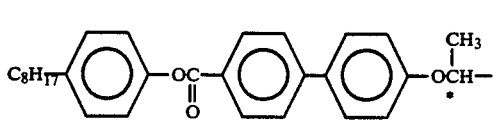 (32)
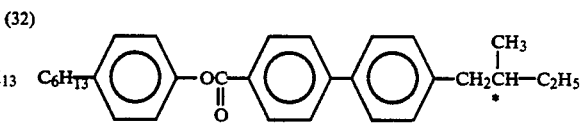 (33)
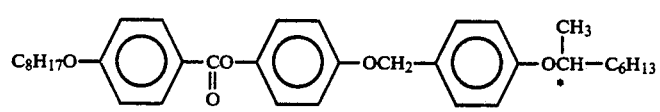 (34)
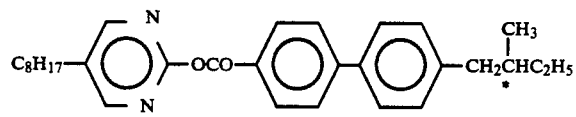 (35)
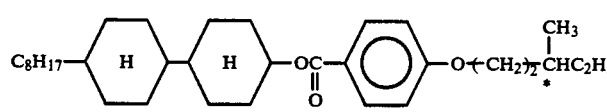 (36)
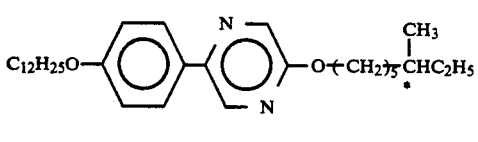 (37)
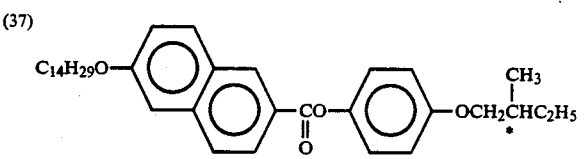 (38)
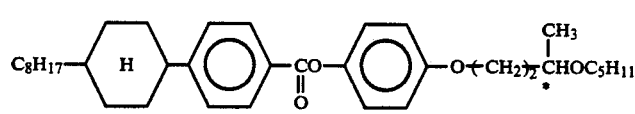 (39)
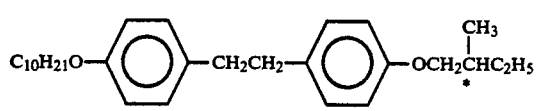 (40)
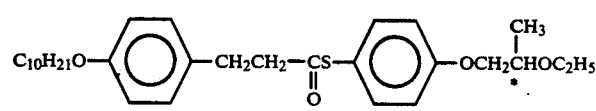 (41)
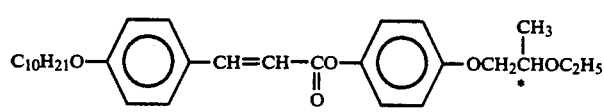 (42)

-continued
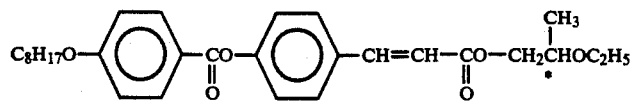 (43)
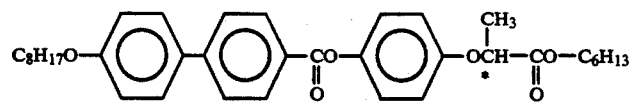 (44)
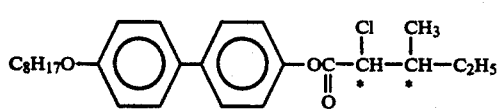 (45)
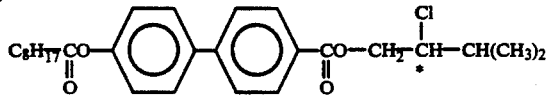 (46)
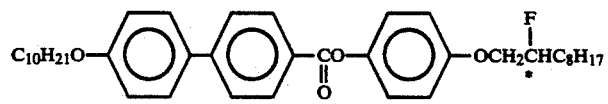 (47)
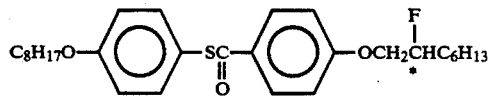 (48)
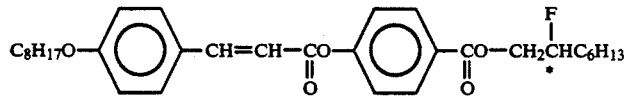 (49)
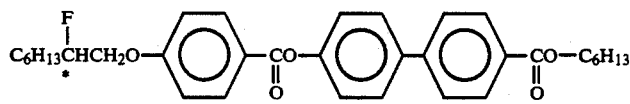 (50)
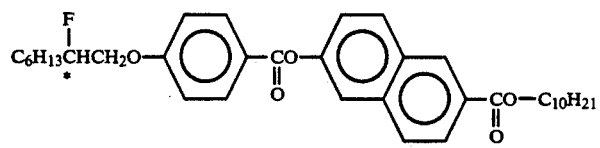 (51)
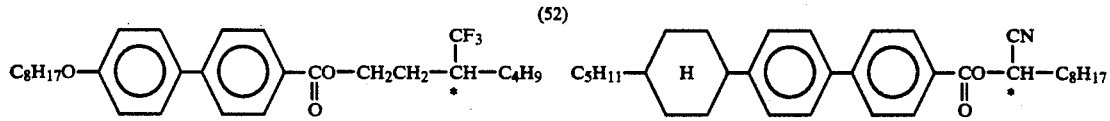 (52)
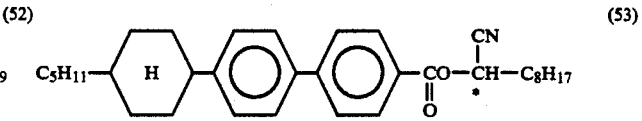 (53)
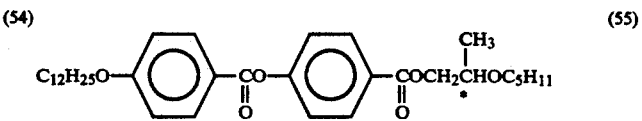 (54)
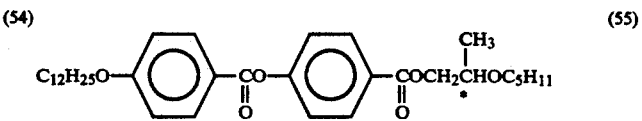 (55)
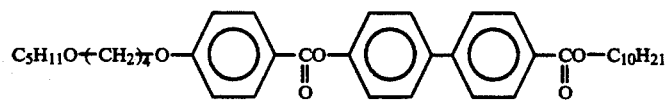 (56)
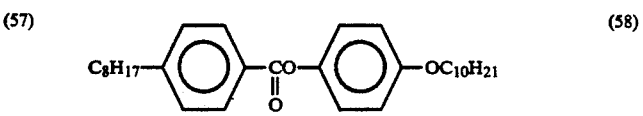 (57) (58)
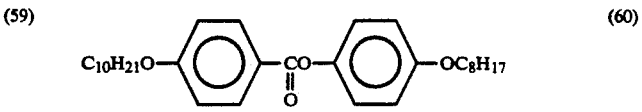 (59) (60)
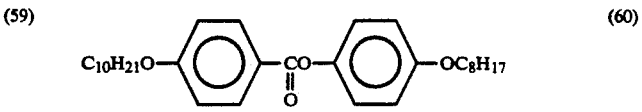
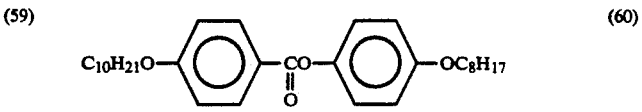

-continued
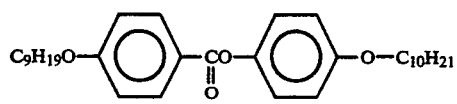 (61)
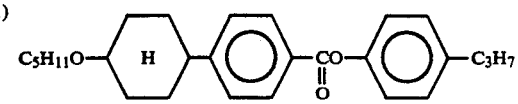 (62)
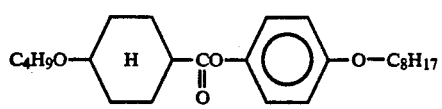 (63)
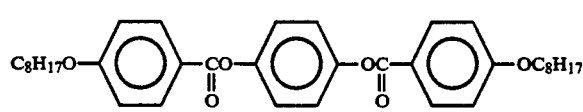 (64)
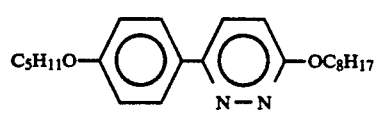 (65)
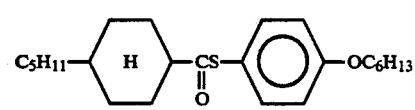 (66)
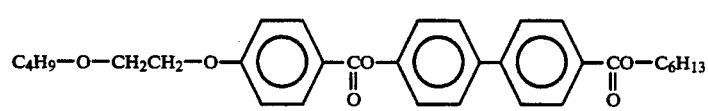 (67)
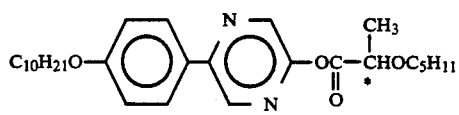 (68)
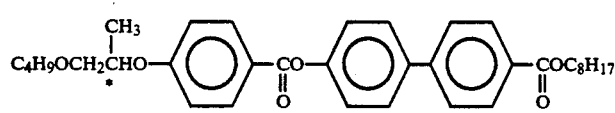 (69)
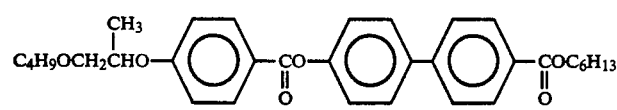 (70)
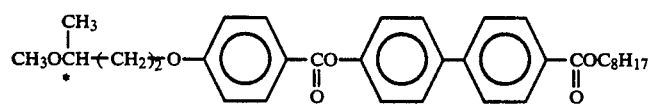 (71)
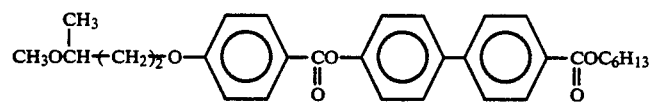 (72)
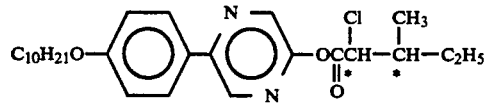 (73)
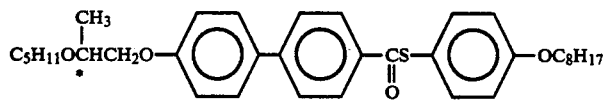 (74)
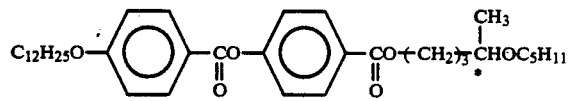 (75)
In formulating the liquid crystal composition according to the present invention, it is desirable to mix 1–300 wt. parts each, preferably 2–100 wt. parts each, of a compound represented by the formula (II), a compound represented by the formula (III) and a compound represented by either the formula (I) or (IV) with 100 wt.

parts of another mesomorphic compound as mentioned above which can be composed of two or more species.

Further, when two or more species of either one or two or all of the compounds represented by the formulas (II), (III) and either (I) or (IV) are used, the two or more species of the compound of the formula (II), (III), (I) or (IV) may be used in a total amount of 1–500 wt. parts, preferably 1–100 wt. parts, per 100 wt. parts of another mesomorphic compound as described above which can be composed of two or more species.

Further, the weight ratio of the compound of the formula (II)/the compound of the formula (III)/the compound of either the formula (I) or (IV) may desirably be 1–300/1–300/1–300, preferably 1–50/1–50/1–50. When two or more species each of the compounds of the formulas (II), (III) and (I) or (IV) are used, the weight ratio of the total amount of the compounds of the formula (II)/the total amounts of the compounds of the formula (III)/the total amounts of the compounds of the formula (I) or (IV) may desirably be 1–500/1–500/1–500, preferably 1–50/1–50/1–50.

Further, the total amounts of the compounds of the formulas (II), (III) and (I) or (IV) may desirably be 3–90 wt. parts, preferably 6–300 wt. parts, when one species each is selected from the formulas (II) (III) and either (I) or (IV), or 3–1500 wt. parts, preferably 6–300 wt. parts, when two or more species are selected from at least one of the formulas (II), (III) and either (I) or (IV), respectively, with respect to 100 wt. parts of the above-mentioned another mesomorphic compound which may be composed of two or more species.

Further, a mesomorphic compound having a negative dielectric anisotropy as described above can be contained in a proportion of 1–97 wt % of the liquid crystal composition of the present invention so as to provide a composition having a negative dielectric anisotropy. Particularly, when a mesomorphic compound having $\Delta \epsilon < -2$ is used, it may be contained in a proportion of 1–70 wt. %, preferably 1–50 wt. %, of the liquid crystal composition of the present invention.

Further, the total of the compounds of the formulas (II), (III) and either (I) or (IV) and the mesomorphic compound having a negative dielectric anisotropy can constitute 4–100 wt. % of the liquid crystal composition of the present invention.

The ferroelectric liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the ferroelectric liquid crystal device prepared as described above for explanation of the structure thereof.

Referring to FIG. 1, the ferroelectric liquid crystal device includes a ferroelectric liquid crystal layer 1 disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a selection of an organic insulating material or a precursor thereof in a concentration of 0.1 to 20 wt %, preferably 0.2–10 wt. %, by spinner coating, dip coating, screen printing, spray coating or roller coating, followed by curing or hardening under prescribed hardening condition (e.g., by heating). The insulating alignment control layer may have a thickness of ordinarily 30 Å–1 micron, preferably 30–3000 Å, further preferably 50–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a ferroelectric liquid crystal is sealed up to provide a ferroelectric liquid crystal layer 1 in a thickness of generally 0.5 to 20 microns, preferably 1 to 5 microns.

The ferroelectric liquid crystal provided by the composition of the present invention may desirably assume a SmC* phase (chiral smectic C phase) in a wide temperature range including room temperature (particularly, broad in a lower temperature side) and also shows wide drive voltage margin and drive temperature margin when contained in a device.

Particularly, in order to show a good alignment characteristic to form a uniform monodomain, the ferroelectric liquid crystal may show a phase transition series comprising isotropic phase—Ch phase (cholesteric phase)—SmA phase (smectic A phase)—SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
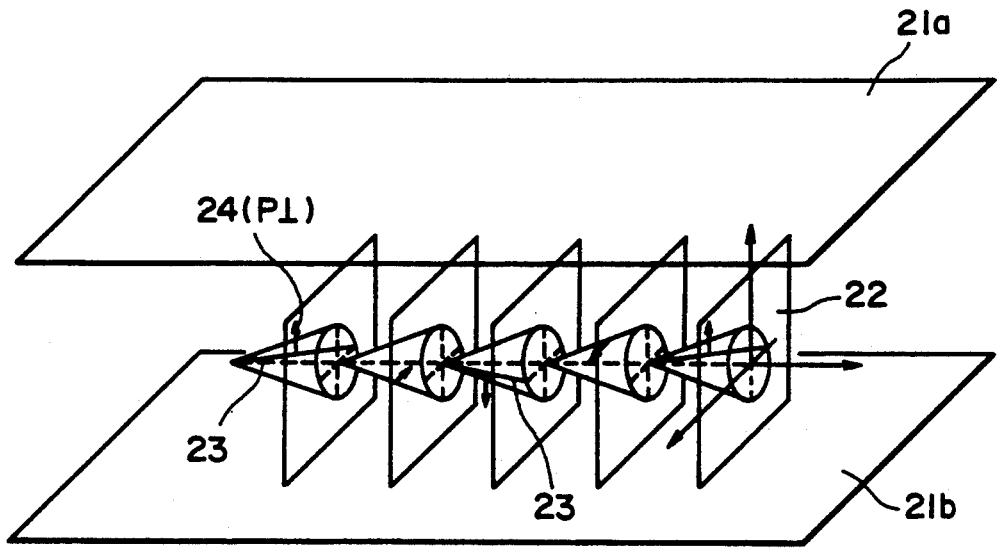
FIGS. 2 and 3 are schematic perspective views of a device cell embodiment for illustrating the operation principle of a ferroelectric liquid crystal device.

FIG. 2 is a schematic illustration of a ferroelectric liquid crystal cell (device) for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment ($P_\perp$) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments ($P_\perp$) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
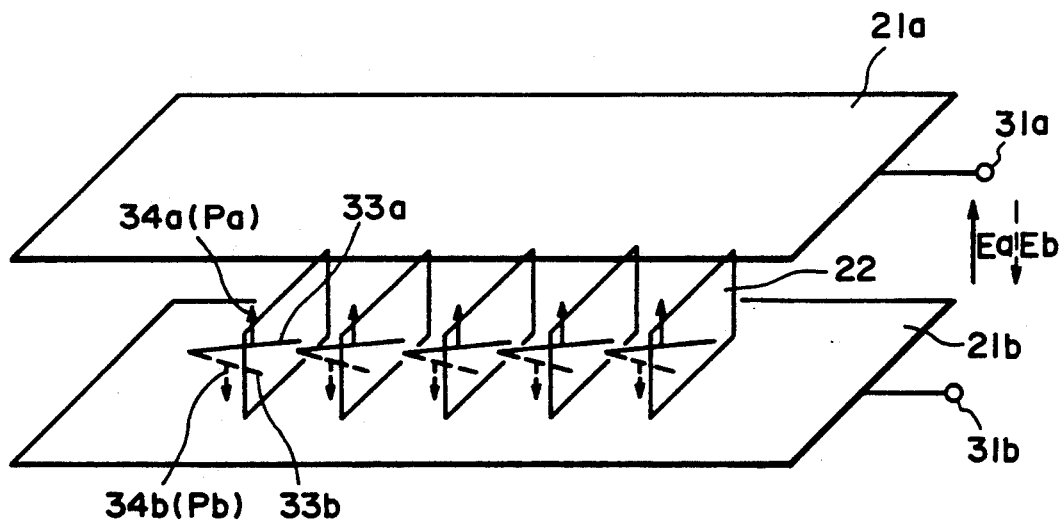
Figure 4:
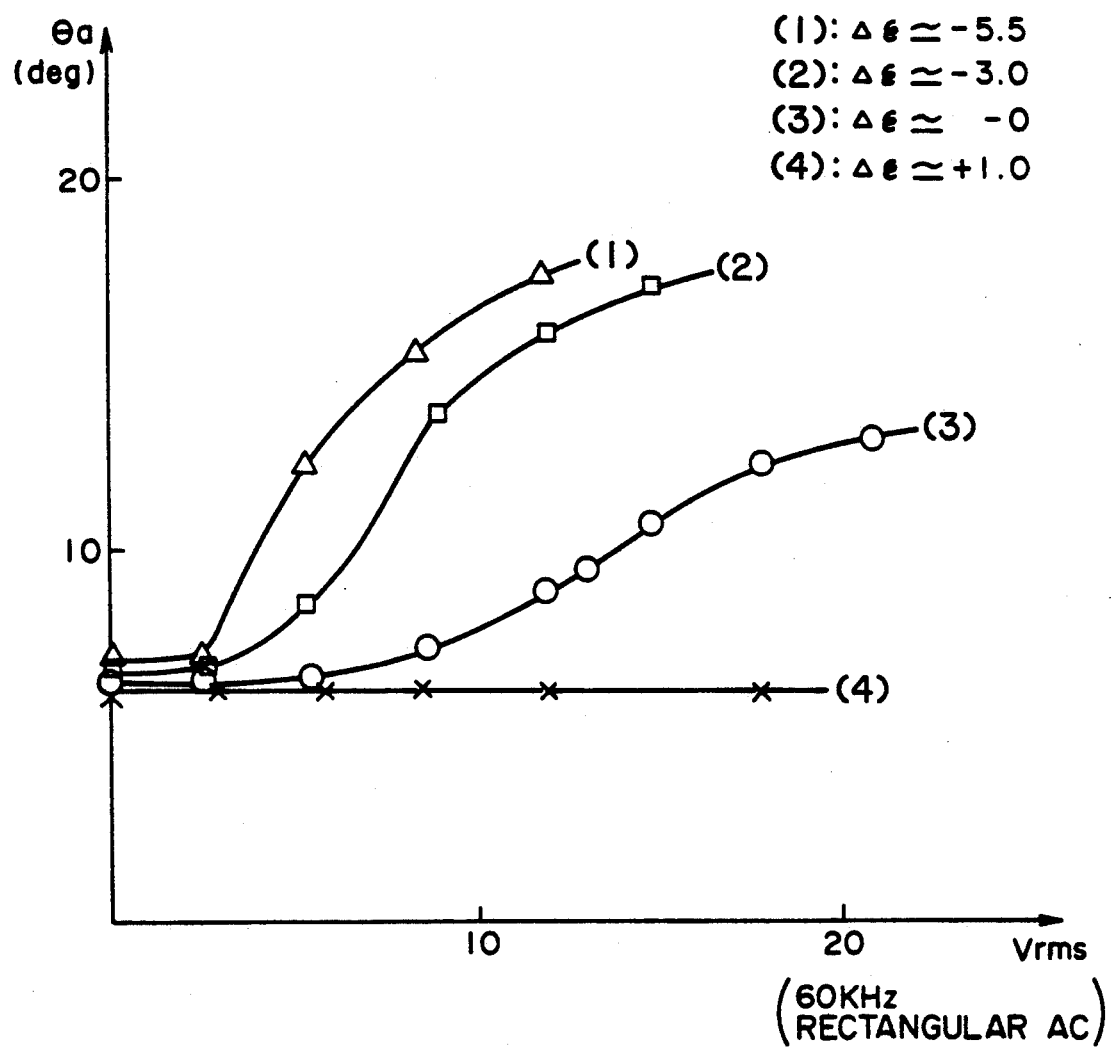
FIG. 4 is a graph showing changes in tilt angle $\theta a$ versus effective voltage Vrms with respect to several ferroelectric liquid crystals having different values of dielectric anisotropy $\Delta\epsilon$.

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

When such a ferroelectric liquid crystal device comprising a ferroelectric liquid crystal composition as described above between a pair of electrode plates is constituted as a simple matrix display device, the device may be driven by a driving method as disclosed in Japanese Laid-Open Patent Applications (KOKAI) Nos. 193426/1984, 193427/1984, 156046/1985, 156047/1985, etc.

Hereinbelow, the present invention will be explained more specifically with reference to examples. It is however to be understood that the present invention is not restricted to these examples.

EXAMPLE 1

A liquid crystal composition 1-A was prepared by mixing the following compounds in respectively indicated proportions.

| Ex. Compound No. | Structural formula | Wt. parts |
|---|---|---|
| 7 | $C_8H_{17}$—⟨O⟩—COO—⟨O⟩—⟨O⟩—OCH$_2$CHC$_2$H$_5$ with CH$_3$ branch (*) | 15 |
| 15 | $C_3H_7OCH$—$(CH_2)_3$—O—⟨O⟩—COO—⟨O⟩—⟨O⟩—OC$_6$H$_{13}$ with CH$_3$ branch (*) | 5 |
| 16 | $C_3H_7OCH$—$(CH_2)_3$—O—⟨O⟩—COO—⟨O⟩—⟨O⟩—COOC$_6$H$_{13}$ with CH$_3$ branch (*) | 10 |
| 57 | $C_{10}H_{21}O$—⟨O⟩—COO—⟨O⟩—OC$_8$H$_{17}$ | 5 |

-continued

| Ex. Compound No. | Structural formula | Wt. parts |
|---|---|---|
| 58 | $C_8H_{17}$—⟨⟩—COO—⟨⟩—$OC_{10}H_{21}$ | 8 |
| 59 | $C_{10}H_{21}O$—⟨⟩—COO—⟨⟩—$OC_6H_{13}$ | 5 |
| 60 | $C_{10}H_{21}$—⟨⟩—COO—⟨⟩—$OC_8H_{17}$ | 12 |
| 12 | $C_8H_{17}O$—⟨⟩—COS—⟨⟩—$OCH_2\overset{*}{C}H(CH_3)C_2H_5$ | 9 |
| 13 | $C_{10}H_{21}O$—⟨⟩—COS—⟨⟩—$OCH_2\overset{*}{C}H(CH_3)C_2H_5$ | 6 |
| 69 | $C_4H_9OCH_2\overset{*}{C}H(CH_3)O$—⟨⟩—⟨⟩—COO—⟨⟩—$COOC_8H_{17}$ | 5 |
| 55 | $C_{12}H_{25}O$—⟨⟩—COO—⟨⟩—$COOCH_2\overset{*}{C}H(CH_3)OC_5H_{11}$ | 15 |
| 75 | $C_{12}H_{25}O$—⟨⟩—COO—⟨⟩—$COO(CH_2)_3\overset{*}{C}H(CH_3)OC_5H_{11}$ | 5 |

A liquid crystal composition 1-B was prepared by mixing the following example compounds in the respectively indicated proportions with the above prepared composition 1-A.

| Ex. Comp. No. | Structural formula | Wt. parts |
|---|---|---|
| 1-23 | n-$C_8H_{17}$—⟨pyrimidine⟩—⟨⟩—$OC_9H_{19}$-n | 6 |
| 1-106 | n-$C_7H_{15}$—⟨pyrimidine⟩—⟨⟩—$O(CH_2)_3\overset{*}{C}H(CH_3)CH_2C_2H_5$ | 3 |
| 1-148 | n-$C_{12}H_{25}O$—⟨pyrimidine⟩—⟨⟩—$O(CH_2)_3\overset{*}{C}H(CH_3)CH_2C_2H_5$ | 3 |

-continued

| Ex. Comp. No. | Structural formula | Wt. parts |
|---|---|---|
| 2-2 | 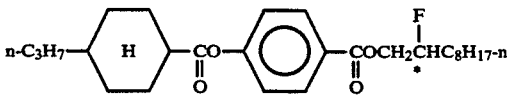 n-C$_3$H$_7$—〈H〉—CO—O—〈◯〉—COCH$_2$CHC$_8$H$_{17}$-n (with F substituent) ‖O ‖O | 4 |
| 3-27 | 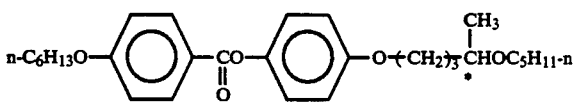 n-C$_6$H$_{13}$O—〈◯〉—CO—〈◯〉—O—(CH$_2$)$_3$CHOC$_5$H$_{11}$-n (with CH$_3$) ‖O | 5 |
| | Composition 1-A | 79 |

The above-prepared liquid crystal composition 1-B was used to prepare a liquid crystal device in combination with a blank cell prepared in the following manner.

Two 1.1 mm-thick glass plates were provided and respectively coated with an ITO film to form an electrode for voltage application, which was further coated with an insulating layer of vapor-deposited SiO$_2$. The insulating layer was further coated with a 1.0%-solution of polyimide resin precursor (SP-710, available from Toray K. K.) in dimethylacetamide by a spinner coater rotating at 2500 rpm for 15 seconds. Thereafter, the coating film was subjected to heat curing at 300° C. for 60 min. to obtain about 200 Å-thick film. The coating film was rubbed with acetate fiber-planted cloth. The thus treated two glass plates were washed with isopropyl alcohol. After silica beads with an average particle size of 1.5 microns were dispersed on one of the glass plates, the two glass plates were applied to each other with a bonding sealing agent (Lixon Bond, available from Chisso K. K.) so that their rubbed directions were parallel to each other and heated at 100° C. for 60 min. to form a blank cell. The cell gap was found to be about 1.5 microns as measured by a Berek compensator.

Then, the above-prepared liquid crystal composition 1-B was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of an optical response time (time from voltage application until the transmittance change reaches 90% of the maximum) at specified temperatures under the application of a peak-to-peak voltage Vpp of 25 volts. The results are shown below.

| | 10° C. | 25° C. | 40° C. |
|---|---|---|---|
| Response time | 964 μsec | 338 μsec | 127 μsec |

Further, a contrast of 13 was attained at 25° C. during the driving, and a clear switching function was observed. The bistability after termination of the voltage application was also good.

COMPARATIVE EXAMPLE 1

A liquid crystal composition 1-C was prepared by omitting Example compounds Nos. 1-23, 1-106 and 1-148 from the liquid crystal composition 1-B, i.e., by adding only Example compounds Nos. 2-2 and 3-27 to the liquid crystal composition 1-A, a liquid crystal composition 1-D was prepared by omitting Example compound No. 2-2 from the composition 1-B, i.e., by adding only Example compounds Nos. 1-23, 1-106, 1-148 and 3-27 to the composition 1-A, and a liquid crystal composition 1-E was prepared by omitting Example compound No. 3-27 from the composition 1-B, i.e., by adding only Example compounds Nos. 1-23, 1-106, 1-148 and 2-2 to the composition 1-A.

Ferroelectric liquid crystal devices 1-A, 1-C 1-D and 1-E were prepared by using the compositions 1-A, 1-C, 1-D and 1-E, respectively, instead of the composition 1-B, and subjected to measurement of optical response time, otherwise in the same manner as in Example 1. The results are shown below.

| | Response time | | |
|---|---|---|---|
| | 10° C. | 25° C. | 40° C. |
| 1-A | 1410 μsec | 435 μsec | 155 μsec |
| 1-C | 1012 μsec | 348 μsec | 130 μsec |
| 1-D | 1131 μsec | 378 μsec | 136 μsec |
| 1-E | 997 μsec | 345 μsec | 129 μsec |

As apparent from the above Example 1 and Comparative Example 1, the ferroelectric liquid crystal device containing the liquid crystal composition 1-B according to the present invention provided improved response speed and operation characteristic at a lower temperature and also provided a decreased temperature dependence of response speed (ratio of response time (10° C./40° C.)).

A liquid crystal composition 2-B was prepared by mixing the following example compounds in the indicated proportions with the liquid crystal composition 1-A prepared in Example 1.

| Ex. Comp. No. | Structural formula | wt. parts |
|---|---|---|
| 1-57 | 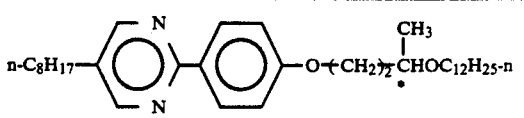 n-C$_8$H$_{17}$—〈N◯N〉—〈◯〉—O—(CH$_2$)$_2$CHOC$_{12}$H$_{25}$-n (with CH$_3$) | 4 |

| Ex. Comp. No. | Structural formula | wt. parts |
|---|---|---|
| 1-80 | n-$C_{10}H_{21}$—[pyridine]—[phenyl]—O—$(CH_2)_7$—$\overset{CH_3}{\underset{*}{C}H}$—$OC_2H_5$ | 4 |
| 1-141 | n-$C_{10}H_{21}O$—[pyridine]—[phenyl]—$\underset{O}{\overset{\parallel}{C}}$O—$CH_2\overset{CH_3}{\underset{*}{C}H}C_2H_5$ | 6 |
| 2-28 | n-$C_6H_{13}$—[pyridine]—[phenyl]—$OCH_2\overset{F}{\underset{*}{C}H}C_4H_9$-n | 10 |
| 3-24 | n-$C_{10}H_{21}O$—[phenyl]—$\underset{O}{\overset{\parallel}{C}}$O—[phenyl]—O—$(CH_2)_3$—$\overset{CH_3}{\underset{*}{C}H}CH_2C_2H_5$ | 8 |
| Composition 1-A | | 68 |

A ferroelectric liquid crystal device was prepared in the same manner as in Example 1 except that the above liquid crystal composition 2-B was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 711 μsec | 240 μsec | 92 μsec |

Further, a contrast of 13 was attained at 25° C. during the driving, and a clear switching function was observed. The bistability after termination of the voltage application was also good.

COMPARATIVE EXAMPLE 2

A liquid crystal composition 2-C was prepared by adding only Example compounds Nos. 1-57, 1-80, 1-141 and 3-24 and without adding Example compound No. 2-28 to the composition 1-A.

Ferroelectric liquid crystal devices were prepared by using the compositions 2-C and 1-A, respectively, instead of the composition 1-B, and subjected to measurement of optical response time, otherwise in the same manner as in Example 1. The results are shown below.

| | Response time | | |
|---|---|---|---|
| | 10° C. | 25° C. | 40° C. |
| 1-A | 1410 μsec | 435 μsec | 155 μsec |
| 2-C | 1175 μsec | 384 μsec | 136 μsec |

As apparent from the above Example 2 and Comparative Example 2, the ferroelectric liquid crystal device containing the liquid crystal composition 2-B according to the present invention provided improved response speed and operation characteristic at a lower temperature and also provided a decreased temperature dependence of response speed.

EXAMPLE 3

A liquid crystal composition 3-B was prepared by mixing the following example compounds in the indicated proportions with the liquid crystal composition 1-A prepared in Example 1.

| Ex. Comp. No. | Structural formula | wt. parts |
|---|---|---|
| 1-73 | n-$C_{12}H_{25}$—[pyridine]—[phenyl]—O—$(CH_2)_4$—$\overset{CH_3}{\underset{*}{C}H}OCH_3$ | 6 |
| 1-118 | n-$C_{10}H_{21}$—[pyridine]—[phenyl]—$\underset{O}{\overset{\parallel}{O}C}$—$(CH_2)_4$—$\overset{CH_3}{\underset{*}{C}H}C_2H_5$ | 4 |
| 2-63 | n-$C_{16}H_{33}$—[pyridine]—[phenyl]—$OCH_2\overset{F}{\underset{*}{C}H}$—$C_8H_{17}$-n | 10 |

| Ex. Comp. No. | Structural formula | wt. parts |
|---|---|---|
| 3-36 | 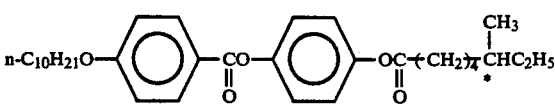 n-C$_{10}$H$_{21}$O—⟨⟩—CO—⟨⟩—OC—(CH$_2$)$_{\overline{2}}$*CHC$_2$H$_5$ with CH$_3$ branch, C=O groups | 5 |
| 3-41 | 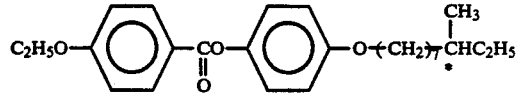 C$_2$H$_5$O—⟨⟩—CO—⟨⟩—O—(CH$_2$)$_{\overline{2}}$*CHC$_2$H$_5$ with CH$_3$ branch | 4 |
| | Composition 1-A | 71 |

A ferroelectric liquid crystal device was prepared in the same manner as in Example 1 except that the above liquid crystal composition 3-B was used, and the device was subjected to measurement of driving voltage margin and observation of switching states. In the device, a monodomain with a good and uniform alignment characteristic was observed. The results of the measurement are shown below.

|  | 10° C. | 25° C. | 40° C. |
|---|---|---|---|
| Response time | 763 μsec | 266 μsec | 98 μsec |

Further, a contrast of 13 was attained at 25° C. during the driving, and a clear switching function was observed. The bistability after termination of the voltage application was also good.

COMPARATIVE EXAMPLE 3

A liquid crystal composition 3-C was prepared by adding only Example compounds Nos. 1-73, 1-118, 3-36 and 3-41 and without adding Example compound No. 2-63 to the composition 1-A.

Ferroelectric liquid crystal devices were prepared by using the compositions 3-C and 1-A, respectively, instead of the composition 1-B, and subjected to measurement of optical response time, otherwise in the same manner as in Example 1. The results are shown below.

| | Response time | | |
|---|---|---|---|
| | 10° C. | 25° C. | 40° C. |
| 1-A | 1410 μsec | 435 μsec | 155 μsec |
| 3-C | 1080 μsec | 372 μsec | 139 μsec |

As apparent from the above Example 3 and Comparative Example 3, the ferroelectric liquid crystal device containing the liquid crystal composition 3-B according to the present invention provided improved response speed and operation characteristic at a lower temperature and also provided a decreased temperature dependence of response speed.

EXAMPLE 4

A liquid crystal composition 4-A was prepared by mixing the following compounds in respectively indicated proportions.

| Ex. Compound No. | Structural formula | Wt. parts |
|---|---|---|
| 57 | 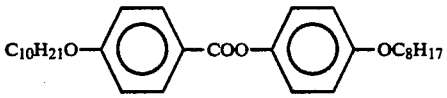 C$_{10}$H$_{21}$O—⟨⟩—COO—⟨⟩—OC$_8$H$_{17}$ | 7 |
| 58 | 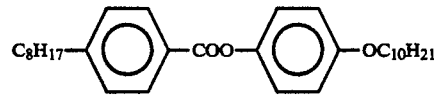 C$_8$H$_{17}$—⟨⟩—COO—⟨⟩—OC$_{10}$H$_{21}$ | 7 |
| 59 | 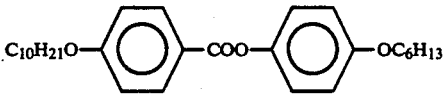 C$_{10}$H$_{21}$O—⟨⟩—COO—⟨⟩—OC$_6$H$_{13}$ | 10 |
| 60 | 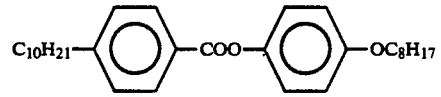 C$_{10}$H$_{21}$—⟨⟩—COO—⟨⟩—OC$_8$H$_{17}$ | 10 |
| 8 | 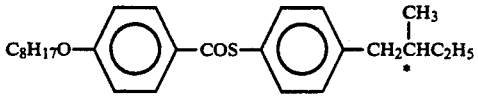 C$_8$H$_{17}$O—⟨⟩—COS—⟨⟩—CH$_2$*CHC$_2$H$_5$ with CH$_3$ branch | 4 |

-continued

| Ex. Compound No. | Structural formula | Wt. parts |
|---|---|---|
| 9 | $C_{12}H_{25}O-\phenyl-COS-\phenyl-CH_2\overset{*}{C}H(CH_3)C_2H_5$ | 4 |
| 12 | $C_8H_{17}O-\phenyl-COS-\phenyl-OCH_2\overset{*}{C}H(CH_3)C_2H_5$ | 4 |
| 13 | $C_{10}H_{21}O-\phenyl-COS-\phenyl-OCH_2\overset{*}{C}H(CH_3)C_2H_5$ | 4 |
| 16 | $C_3H_7O\overset{*}{C}H(CH_3)(CH_2)_3O-\phenyl-COO-\phenyl-\phenyl-COOC_6H_{13}$ | 10 |
| 69 | $C_4H_9OCH_2\overset{*}{C}H(CH_3)O-\phenyl-COO-\phenyl-\phenyl-COOC_8H_{17}$ | 15 |
| 71 | $CH_3O\overset{*}{C}H(CH_3)(CH_2)_2O-\phenyl-COO-\phenyl-\phenyl-COOC_8H_{17}$ | 10 |
| 55 | $C_{12}H_{25}O-\phenyl-COO-\phenyl-COO-CH_2\overset{*}{C}H(CH_3)OC_5H_{11}$ | 5 |
| 75 | $C_{12}H_{25}O-\phenyl-COO-\phenyl-COO-(CH_2)_3\overset{*}{C}H(CH_3)OC_5H_{11}$ | 10 |

A liquid crystal composition 4-B was prepared by mixing the following example compounds in the respectively indicated proportions with the above prepared composition 4-A.

| Ex. Comp. No. | Structural formula | wt. parts |
|---|---|---|
| 1-23 | $n\text{-}C_8H_{17}-\text{pyrimidine}-\phenyl-OC_9H_{19}\text{-}n$ | 5 |
| 1-106 | $n\text{-}C_7H_{15}-\text{pyrimidine}-\phenyl-O(CH_2)_3\overset{*}{C}H(CH_3)C_2H_5$ | 2 |
| 1-148 | $n\text{-}C_{12}H_{25}O-\text{pyrimidine}-\phenyl-O(CH_2)_3\overset{*}{C}H(CH_3)C_2H_5$ | 2 |

| Ex. Comp. No. | Structural formula | wt. parts |
|---|---|---|
| 2-2 | $n\text{-}C_3H_7\text{-}[H]\text{-}COO\text{-}[\bigcirc]\text{-}COOCH_2\overset{*}{C}H(F)C_8H_{17}\text{-}n$ | 5 |
| 3-27 | $n\text{-}C_6H_{13}O\text{-}[\bigcirc]\text{-}COO\text{-}[\bigcirc]\text{-}O\text{-}(CH_2)_3\overset{*}{C}H(CH_3)OC_5H_{11}\text{-}n$ | 4 |
| | Composition 4-A | 82 |

A ferroelectric liquid crystal device 4-B was prepared in the same manner as in Example 1 except that the liquid crystal composition 4-B was used instead of the composition 1-B. The device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time | 837 μsec | 292 μsec | 114 μsec |

Further, a contrast of 13 was attained at 25° C. during the driving, and a clear switching function was observed.

COMPARATIVE EXAMPLE 4

A liquid crystal composition 4-C was prepared by adding only Example compounds Nos. 2-2 and 3-27 and without adding Example compound No. 1-23, 1-148 or 1-106 to the composition 4-A; a liquid crystal composition 4-D was prepared by adding only Example compounds Nos. 1-23, 1-148, 1-106 and 3-27 and without adding Example compound No. 2-2 to the composition 4-A; and a liquid crystal composition 4-E was prepared by adding only Example compounds Nos. 1-23, 1-148, 1-106 and 2-2 and without adding Example compound No. 3-27 to the composition 4-A.

Ferroelectric liquid crystal devices were prepared by using the compositions 4-C, 4-D, 4-E and 4-A, respectively, instead of the composition 1-B, and subjected to measurement of optical response time, otherwise in the same manner as in Example 1. The results are shown below.

|  | Response time (μsec) | | |
|---|---|---|---|
|  | 10° C. | 25° C. | 40° C. |
| 4-A | 1260 μsec | 374 μsec | 137 μsec |
| 4-C | 936 μsec | 322 μsec | 120 μsec |
| 4-D | 1072 μsec | 359 μsec | 132 μsec |
| 4-E | 872 μsec | 303 μsec | 117 μsec |

As apparent from the above Example 4 and Comparative Example 4, the ferroelectric liquid crystal device containing the liquid crystal composition 4-B according to the present invention provided improved response speed and operation characteristic at a lower temperature and also provided a decreased temperature dependence of response speed.

EXAMPLE 5

A liquid crystal composition 5-B was prepared by mixing the following example compounds in the indicated proportions with the liquid crystal composition 4-A prepared in Example 4.

| Ex. Comp. No. | Structural formula | wt. parts |
|---|---|---|
| 1-21 | $n\text{-}C_7H_{15}\text{-}[\text{pyrimidine}]\text{-}[\bigcirc]\text{-}OC_9H_{19}\text{-}n$ | 5 |
| 1-46 | $n\text{-}C_8H_{17}\text{-}[\text{pyrimidine}]\text{-}[\bigcirc]\text{-}O(CH_2)_2O\text{-}C_4H_9\text{-}n$ | 5 |
| 1-72 | $n\text{-}C_{11}H_{23}\text{-}[\text{pyrimidine}]\text{-}[\bigcirc]\text{-}O(CH_2)_2\overset{*}{C}H(CH_3)OCH_3$ | 3 |
| 2-53 | $n\text{-}C_{12}H_{25}\text{-}[\text{pyrimidine}]\text{-}[\bigcirc]\text{-}OCH_2\overset{*}{C}H(F)\text{-}C_5H_{11}\text{-}n$ | 4 |

| Ex. Comp. No. | Structural formula | wt. parts |
|---|---|---|
| 3-49 | n-$C_{12}H_{25}O$—⟨phenyl⟩—CO—O—⟨phenyl⟩—$OCH_2\overset{*}{C}HC_2H_5$ (with $CH_3$) | 8 |
| | Composition 4-A | 75 |

A ferroelectric liquid crystal device was prepared in the same manner as in Example 1 except that the above liquid crystal composition 5-B was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 815 μsec | 285 μsec | 111 μsec |

Further, a contrast of 13 was attained at 25° C. during the driving, and a clear switching function was observed. The bistability after termination of the voltage application was also good.

COMPARATIVE EXAMPLE 5

A liquid crystal composition 5-C was prepared by adding only Example compound No. 2-53 and without adding Example compound No. 1-12, 1-14, 1-72 or 3-49 to the composition 4-A.

Ferroelectric liquid crystal devices were prepared by using the compositions 5-C and 4-A, respectively, instead of the composition 1-B, and subjected to measurement of optical response time, otherwise in the same manner as in Example 1. The results are shown below.

| | Response time (μsec) | | |
|---|---|---|---|
| | 10° C. | 25° C. | 40° C. |
| 4-A | 1260 | 374 | 137 |
| 5-C | 869 | 300 | 113 |

As apparent from the above Example 5 and Comparative Example 5, the ferroelectric liquid crystal device containing the liquid crystal composition 5-B according to the present invention provided improved response speed and operation characteristic at a lower temperature and also provided a decreased temperature dependence of response speed.

EXAMPLE 6

A liquid crystal composition 6-B was prepared by mixing the following example compounds in the indicated proportions with the liquid crystal composition 4-A prepared in Example 4.

| Ex. Comp. No. | Structural formula | wt. parts |
|---|---|---|
| 1-97 | n-$C_{12}H_{25}$—⟨pyrimidine⟩—⟨phenyl⟩—O$(CH_2)_2\overset{*}{C}HC_2H_5$ (with $CH_3$) | 6 |
| 1-138 | n-$C_{12}H_{25}O$—⟨pyrimidine⟩—⟨phenyl⟩—O$(CH_2)_3\overset{*}{C}HC_2H_5$ (with $CH_3$) | 3 |
| 1-140 | n-$C_6H_{13}O$—⟨pyrimidine⟩—⟨phenyl⟩—OC(O)—$\overset{*}{C}HC_2H_5$ (with $CH_3$) | 3 |
| 2-12 | n-$C_4H_9$—⟨cyclohexyl⟩—CO—O—⟨phenyl⟩—$OCH_2\overset{*}{C}H$—$C_8H_{17}$-n (with F) | 4 |
| 3-42 | n-$C_8H_{17}O$—⟨phenyl⟩—CO—O—⟨phenyl⟩—$O\overset{*}{C}HC_6H_{13}$-n (with $CH_3$) | 6 |
| | Composition 4-A | 78 |

A ferroelectric liquid crystal device was prepared in the same manner as in Example 1 except that the above liquid crystal composition 6-B was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time | 682 μsec | 244 μsec | 93 μsec |

Further, a contrast of 13 was attained at 25° C. during the driving, and a clear switching function was observed. The bistability after termination of the voltage application was also good.

COMPARATIVE EXAMPLE 6

A liquid crystal composition 6-C was prepared by adding only Example compounds Nos. 1-97, 1-138 and 1-140 and without adding Example compound No. 2-12 or 3-42 to the composition 4-A.

Ferroelectric liquid crystal devices were prepared by using the compositions 6-C and 4-A, respectively, instead of the composition 1-B, and subjected to measurement of optical response time, otherwise in the same manner as in Example 1. The results are shown below.

|  | Response time | | |
|---|---|---|---|
|  | 10° C. | 25° C. | 40° C. |
| 4-A | 1260 μsec | 374 μsec | 137 μsec |
| 6-C | 1044 μsec | 357 μsec | 132 μsec |

As apparent from the above Example 6 and Comparative Example 6, the ferroelectric liquid crystal device containing the liquid crystal composition 6-B according to the present invention provided improved response speed and operation characteristic at a lower temperature and also provided a decreased temperature dependence of response speed.

EXAMPLE 7

A liquid crystal composition 7-A was prepared by mixing the following compounds in respectively indicated proportions.

| Ex. Compound No. | Structural formula | Wt. parts |
|---|---|---|
| 26 | $C_8H_{17}O$—[pyrimidine]—[phenyl]—$O(CH_2)_3CHC_2H_5$ with $CH_3$ | 4 |
| 27 | $C_{10}H_{21}O$—[phenyl]—[pyrimidine]—$COO(CH_2)_3CHC_2H_5$ with $CH_3$ | 2 |
| 28 | $C_{12}H_{25}O$—[phenyl]—[pyrimidine]—$COO(CH_2)_3CHC_2H_5$ with $CH_3$ | 3 |
| 29 | $C_{10}H_{21}O$—[pyrimidine]—[phenyl]—$O(CH_2)_3CHC_2H_5$ with $CH_3$ | 3 |
| 30 | $C_8H_{17}$—[pyrimidine]—[phenyl]—$O(CH_2)_3CHC_2H_5$ with $CH_3$ | 3 |
| 37 | $C_{12}H_{25}O$—[phenyl]—[pyrimidine]—$O(CH_2)_3CHC_2H_5$ with $CH_3$ | 5 |
| 57 | $C_{10}H_{21}O$—[phenyl]—COO—[phenyl]—$OC_8H_{17}$ | 9 |
| 58 | $C_8H_{17}$—[phenyl]—COO—[phenyl]—$OC_{10}H_{21}$ | 10 |

-continued

| Ex. Compound No. | Structural formula | Wt. parts |
|---|---|---|
| 59 | C₁₀H₂₁O—⟨⟩—COO—⟨⟩—OC₆H₁₃ | 6 |
| 60 | C₁₀H₂₁—⟨⟩—COO—⟨⟩—OC₈H₁₇ | 15 |
| 7 | C₈H₁₇—⟨⟩—COO—⟨⟩—⟨⟩—OCH₂CH*C₂H₅ with CH₃ | 5 |
| 15 | C₃H₇OCH*(CH₂)₃O—⟨⟩—COO—⟨⟩—⟨⟩—OC₆H₁₃ with CH₃ | 5 |
| 69 | C₄H₉OCH₂CH*O—⟨⟩—COO—⟨⟩—⟨⟩—COOC₈H₁₇ with CH₃ | 14 |
| 71 | CH₃OCH*(CH₂)₂O—⟨⟩—COO—⟨⟩—⟨⟩—COOC₈H₁₇ with CH₃ | 16 |

A liquid crystal composition 7-B was prepared by mixing the following example compounds in the respectively indicated proportions with the above prepared composition 7-A.

A ferroelectric liquid crystal device 7-B was prepared in the same manner as in Example 1 except that the liquid crystal composition 7-B was used instead of the composition 1-B. The device was subjected to mea-

| Ex. Comp. No. | Structural formula | Wt. parts |
|---|---|---|
| 1-23 | n-C₈H₁₇—⟨N=N⟩—⟨⟩—OC₉H₁₉-n | 6 |
| 1-106 | n-C₇H₁₅—⟨N=N⟩—⟨⟩—O(CH₂)₃CH*C₂H₅ with CH₃ | 3 |
| 1-148 | n-C₁₂H₂₅O—⟨N=N⟩—⟨⟩—O(CH₂)₃CH*C₂H₅ with CH₃ | 3 |
| 2-2 | n-C₃H₇—⟨H⟩—COO—⟨⟩—COOCH₂CH*C₈H₁₇-n with F | 6 |
| 3-27 | n-C₆H₁₃O—⟨⟩—CO—⟨⟩—O(CH₂)₃CH*OC₅H₁₁-n with CH₃ | 6. |
| Composition 7-A | | 76 | surement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time | 580 μsec | 219 μsec | 89 μsec |

Further, a contrast of 13 was attained at 25° C. during the driving, and a clear switching function was observed. The bistability after termination of the voltage application was also good.

COMPARATIVE EXAMPLE 7

A liquid crystal composition 7-C was prepared by adding only Example compounds Nos. 1-23, 1-106, 1-148 and 3-27 and without adding Example compound No. 3-2 to the composition 7-A.

Ferroelectric liquid crystal devices were prepared by using the compositions 7-C and 7-A, respectively, instead of the composition 1-B, and subjected to measurement of optical response time, otherwise in the same manner as in Example 1. The results are shown below.

| | Response time (μsec) | | |
|---|---|---|---|
| | 10° C. | 25° C. | 40° C. |
| 7-A | 872 | 285 | 115 |
| 7-C | 759 | 205 | 108 |

As apparent from the above Example 7 and Comparative Example 7, the ferroelectric liquid crystal device containing the liquid crystal composition 7-B according to the present invention provided improved response speed and operation characteristic at a lower temperature and also provided a decreased temperature dependence of response speed.

EXAMPLE 8

A liquid crystal composition 8-B was prepared by mixing the following example compounds in the indicated proportions with the liquid crystal composition 7-A prepared in Example 7.

| Ex. Comp. No. | Structural formula | wt. parts |
|---|---|---|
| 1-21 | n-C$_7$H$_{15}$—[pyrimidine]—[phenyl]—OC$_9$H$_{19}$-n | 4 |
| 1-46 | n-C$_8$H$_{17}$—[pyrimidine]—[phenyl]—O(CH$_2$)$_2$OC$_4$H$_9$-n | 4 |
| 1-72 | n-C$_{11}$H$_{23}$—[pyrimidine]—[phenyl]—O(CH$_2$)$_2$CH(CH$_3$)OCH$_3$ | 6 |
| 2-53 | n-C$_{12}$H$_{25}$—[pyrimidine]—[phenyl]—OCH$_2$CH(F)—C$_5$H$_{11}$-n* | 6 |
| 3-49 | n-C$_{12}$H$_{25}$O—[phenyl]—CO—O—[phenyl]—OCH$_2$CH(CH$_3$)C$_2$H$_5$* | 8 |
| Composition 7-A | | 72 |

A ferroelectric liquid crystal device was prepared in the same manner as in Example 1 except that the above liquid crystal composition 8-B was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time | 527 μsec | 198 μsec | 82 μsec |

Further, a contrast of 12 was attained at 25° C. during the driving, and a clear switching function was observed. The bistability after termination of the voltage application was also good.

COMPARATIVE EXAMPLE 8

A liquid crystal composition 8-C was prepared by adding only Example compounds Nos. 2-53 and 3-49 and without adding Example compound No. 1-21, 1-46 or 1-72 to the composition 7-A.

Ferroelectric liquid crystal devices were prepared by using the compositions 8-C and 7-A, respectively, instead of the composition 1-B, and subjected to measurement of optical response time, otherwise in the same manner as in Example 1. The results are shown below.

| | Response time (μsec) | | |
|---|---|---|---|
| | 10° C. | 25° C. | 40° C. |
| 7-A | 872 | 285 | 115 |
| 8-C | 583 | 211 | 83 |

As apparent from the above Example 8 and Comparative Example 8, the ferroelectric liquid crystal device containing the liquid crystal composition 8-B according to the present invention provided improved response speed and operation characteristic at a lower temperature and also provided a decreased temperature dependence of response speed.

EXAMPLE 9

A liquid crystal composition 9-B was prepared by mixing the following example compounds in the indicated proportions with the liquid crystal composition 7-A prepared in Example 7.

| Ex. Comp. No. | Structural formula | wt. parts |
|---|---|---|
| 1-7 | n-$C_5H_{11}$—[pyrimidine]—[phenyl]—$COC_7H_{15}$-n | 6 |
| 1-38 | n-$C_9H_{19}O$—[pyrimidine]—[phenyl]—$OC_{11}H_{23}$-n | 6 |
| 2-20 | n-$C_4H_9$—[H]—CO—[phenyl]—$OCH_2\overset{*}{C}HC_5H_{11}$-n (F) | 6 |
| 2-78 | n-$C_{10}H_{21}$—[pyrimidine]—[phenyl]—CO—$CH_2\overset{*}{C}HC_6H_{13}$-n (F) | 2 |
| 3-21 | n-$C_9H_{19}O$—[phenyl]—CO—[phenyl]—$OCH_2\overset{*}{C}HC_2H_5$ ($CH_3$) | 6 |
| 3-33 | n-$C_5H_{11}CO$—[phenyl]—CO—[phenyl]—$(CH_2)_3\overset{*}{C}HC_2H_5$ ($CH_3$) | 4 |
| Composition 7-A | | 70 |

A ferroelectric liquid crystal device was prepared in the same manner as in Example 1 except that the above liquid crystal composition 9-B was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 485 μsec | 185 μsec | 77 μsec |

Further, a contrast of 12 was attained at 25° C. during the driving, and a clear switching function was observed. The bistability after termination of the voltage application was also good.

COMPARATIVE EXAMPLE 9

A liquid crystal composition 9-C was prepared by adding only Example compounds Nos. 3-21 and 3-33 and without adding Example compound No. 1-7, 1-38, 2-78 or 2-20 to the composition 7-A.

Ferroelectric liquid crystal devices were prepared by using the compositions 9-C and 7-A, respectively, instead of the composition 1-B, and subjected to measurement of optical response time, otherwise in the same manner as in Example 1. The results are shown below.

| | Response time | | |
|---|---|---|---|
| | 10° C. | 25° C. | 40° C. |
| 7-A | 872 μsec | 285 μsec | 115 μsec |
| 9-C | 835 μsec | 280 μsec | 116 μsec |

As apparent from the above Example 9 and Comparative Example 9, the ferroelectric liquid crystal device containing the liquid crystal composition 9-B according to the present invention provided improved response speed and operation characteristic at a lower temperature and also provided a decreased temperature dependence of response speed.

EXAMPLES 10-17

Liquid crystal compositions 10-B to 17-B were prepared by replacing the example compounds and the liquid crystal compositions used in Examples 1, 4 and 7 with example compounds and liquid crystal compositions shown in the following Table 1. Ferroelectric liquid crystal devices were prepared by respectively using these compositions instead of the composition 1-B, and subjected to measurement of optical response time and observation of switching states. In the devices, a monodomain with a good and uniform alignment characteristic was observed. The results of the measurement are shown in the following Table 1.

As is apparent from the results shown in the following Table 1, the ferroelectric liquid crystal devices containing the liquid crystal compositions 10-B to 17-B provided improved response speed and a decreased temperature dependence of the response speed.

TABLE 1

| Ex. No. (Comp. No.) | Example compound No. or liquid crystal composition No. (weight parts) | | | | | | | | Response time ($\mu$sec) | | |
|---|---|---|---|---|---|---|---|---|---|---|---|
| | | | | | | | | | 10° C. | 25° C. | 40° C. |
| 10 | 1-9 | 1-42 | 1-132 | 2-30 | 2-65 | 3-23 | | 1-A | 785 | 269 | 99 |
| (10-B) | (6) | (3) | (4) | (5) | (4) | (4) | | (75) | | | |
| 11 | 1-2 | 1-70 | 1-71 | 2-73 | 3-14 | 3-39 | | 1-A | 827 | 290 | 110 |
| (11-B) | (6) | (3) | (3) | (8) | (3) | (3) | | (71) | | | |
| 12 | 1-113 | 1-135 | 1-142 | 2-17 | 2-58 | 3-17 | | 1-A | 711 | 245 | 91 |
| (12-B) | (4) | (4) | (4) | (5) | (5) | (6) | | (72) | | | |
| 13 | 1-36 | 1-73 | 1-133 | 2-71 | 3-40 | 3-42 | | 4-A | 815 | 279 | 107 |
| (13-B) | (8) | (5) | (3) | (7) | (4) | (2) | | (71) | | | |
| 14 | 1-32 | 1-95 | 1-129 | 2-6 | 2-18 | 3-30 | | 4-A | 738 | 259 | 97 |
| (14-B) | (6) | (4) | (4) | (2) | (8) | (6) | | (70) | | | |
| 15 | 1-86 | 1-136 | 1-158 | 2-3 | 3-37 | 3-53 | | 4-A | 548 | 188 | 70 |
| (15-B) | (5) | (6) | (6) | (4) | (5) | (2) | | (72) | | | |
| 16 | 1-22 | 1-67 | 1-137 | 1-107 | 2-40 | 2-10 | 3-22 | 7-A | 475 | 178 | 74 |
| (16-B) | (7) | (5) | (4) | (4) | (5) | (5) | (4) | (66) | | | |
| 17 | 1-64 | 1-102 | 1-120 | 2-8 | 3-38 | 3-48 | | 7-A | 608 | 228 | 93 |
| (17-B) | (5) | (4) | (4) | (5) | (2) | (3) | | (77) | | | |

EXAMPLE 18

A liquid crystal composition 18-A was prepared by mixing the following compounds in respectively indicated proportions.

| Ex. Compound No. | Structural formula | Wt. parts |
|---|---|---|
| 7 | $C_8H_{17}$—⬡—COO—⬡—⬡—OCH$_2$$\overset{*}{C}$HC$_2$H$_5$ (with CH$_3$) | 15 |
| 15 | C$_3$H$_7$O$\overset{*}{C}$H(CH$_3$)(CH$_2$)$_3$O—⬡—COO—⬡—⬡—OC$_6$H$_{13}$ | 5 |
| 16 | C$_3$H$_7$O$\overset{*}{C}$H(CH$_3$)(CH$_2$)$_3$O—⬡—COO—⬡—⬡—COOC$_6$H$_{13}$ | 10 |
| 57 | C$_{10}$H$_{21}$O—⬡—COO—⬡—OC$_8$H$_{17}$ | 6 |
| 58 | C$_8$H$_{17}$—⬡—COO—⬡—OC$_{10}$H$_{21}$ | 8 |
| 59 | C$_{10}$H$_{21}$O—⬡—COO—⬡—OC$_6$H$_{13}$ | 6 |

-continued

| Ex. Compound No. | Structural formula | Wt. parts |
|---|---|---|
| 60 | $C_{10}H_{21}$—◯—COO—◯—$OC_8H_{17}$ | 12 |
| 12 | $C_8H_{17}O$—◯—COS—◯—$OCH_2\overset{*}{C}H(CH_3)C_2H_5$ | 6 |
| 13 | $C_{10}H_{21}O$—◯—COS—◯—$OCH_2\overset{*}{C}H(CH_3)C_2H_5$ | 9 |
| 55 | $C_{12}H_{25}O$—◯—COO—◯—$COOCH_2\overset{*}{C}H(CH_3)OC_5H_{11}$ | 10 |
| 75 | $C_{12}H_{25}O$—◯—COO—◯—$COO(CH_2)_3\overset{*}{C}H(CH_3)OC_5H_{11}$ | 5 |
| 47 | $C_{10}H_{21}O$—◯—◯—COO—◯—$OCH_2\overset{*}{C}H(F)C_8H_{17}$ | 3 |
| 51 | $C_6H_{13}\overset{*}{C}H(F)CH_2O$—◯—COO—◯◯—$COOC_{10}H_{21}$ | 5 |

A liquid crystal composition 18-B was prepared by mixing the following example compounds in the respectively indicated proportions with the above prepared composition 18-A.

| Ex. Comp. No. | Structural formula | Wt. parts |
|---|---|---|
| 4-5 | $n$-$C_3H_7$—(pyrimidine)—◯—◯—$OC_{11}H_{23}$-$n$ | 4 |
| 4-73 | $n$-$C_3H_7$—(cyclohexyl-H)—CO-O—◯—(pyrimidine)—$C_{11}H_{23}$-$n$ | 6 |
| 2-42 | $n$-$C_{10}H_{21}$—(pyrimidine)—◯—$OCH_2\overset{*}{C}H(F)$—$C_8H_{17}$-$n$ | 8 |
| 3-23 | $n$-$C_{12}H_{25}O$—◯—CO-O—◯—$O(CH_2)_2\overset{*}{C}H(CH_3)C_2H_5$ | 6 |
| | Composition 18-A | 76 |

A ferroelectric liquid crystal device was prepared in the same manner as in Example 1 except that the above liquid crystal composition 18-B was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time | 825 μsec | 284 μsec | 107 μsec |

Further, a contrast of 12 was attained at 25° C. during the driving, and a clear switching function was voltage application was also good.

COMPARATIVE EXAMPLE 18

A liquid crystal composition 18-C was prepared by adding only Example compounds Nos. 2-42 and 3-23 and without adding Example compound No. 4-5 or 4-73 to the composition 18-A; a liquid crystal composition 18-D was prepared by adding only Example compounds Nos. 4-5, 4-73 and 2-42 and without adding Example compound No. 2-42 to the composition 18-A; and a liquid crystal composition 18-E was prepared by adding only Example compounds Nos. 4-5, 4-73 and 2-42 and without adding Example compound No. 3-23 to the composition 18-A.

Ferroelectric liquid crystal devices were prepared by using the compositions 18-C, 18-D and 18-E and 18-A, respectively, instead of the composition 18-B, and subjected to measurement of optical response time, otherwise in the same manner as in Example 18. The results are shown below.

| | Response time | | |
|---|---|---|---|
| | 10° C. | 25° C. | 40° C. |
| 18-A | 1360 μsec | 430 μsec | 147 μsec |
| 18-C | 936 μsec | 322 μsec | 117 μsec |
| 18-D | 1164 μsec | 369 μsec | 128 μsec |
| 18-E | 871 μsec | 298 μsec | 110 μsec |

As apparent from the above Example 18 and Comparative Example 18, the ferroelectric liquid crystal device containing the liquid crystal composition 18-B according to the present invention provided improved response speed and operation characteristic at a lower temperature and also provided a decreased temperature dependence of response speed.

EXAMPLE 19

A liquid crystal composition 19-B was prepared by mixing the following example compounds in the indicated proportions with the liquid crystal composition 18-A prepared in Example 18.

| Ex. Comp. No. | Structural formula | wt. parts |
|---|---|---|
| 4-10 | n-C$_8$H$_{17}$—(pyrimidine)—(phenyl)—(phenyl)—C$_5$H$_{11}$-n | 6 |
| 4-151 | n-C$_8$H$_{17}$—(H cyclohexyl)—CH$_2$O—(phenyl)—(phenyl)—OC(=O)—C$_{12}$H$_{25}$-n | 6 |
| 2-32 | n-C$_8$H$_{17}$—(pyrimidine)—(phenyl)—O—CH$_2$CH(F)—C$_7$H$_{15}$-n | 4 |
| 2-14 | n-C$_8$H$_{17}$—(H cyclohexyl)—CO(=O)—(phenyl)—O—CH$_2$CH(F)—C$_6$H$_{13}$-n | 4 |
| 3-7 | n-C$_6$H$_{13}$—(phenyl)—CO(=O)—(phenyl)—O—(CH$_2$)$_3$CH(CH$_3$)C$_2$H$_5$ | 5 |
| Composition 18-A | | 75 |

A ferroelectric liquid crystal device was prepared in the same manner as in Example 1 except that the above liquid crystal composition 19-B was used, and the device was subjected to measurement of driving voltage margin and observation of switching states. In the device, a monodomain with a good and uniform alignment characteristic was observed. The results of the measurement are shown below.

|  | 10° C. | 25° C. | 40° C. |
|---|---|---|---|
| Response time | 757 μsec | 263 μsec | 100 μsec |

Further, a contrast of 13 was attained at 25° C. during the driving, and a clear switching function was observed. The bistability after termination of the voltage application was also good.

COMPARATIVE EXAMPLE 19

A liquid crystal composition 19-C was prepared by adding only Example compounds Nos. 4-10, 4-151 and 3-7 and without adding Example compound No. 2-32 or 2-14 to the composition 18-A.

Ferroelectric liquid crystal devices were prepared by using the compositions 19-C and 18-A, respectively, instead of the composition 1-B, and subjected to measurement of optical response time, otherwise in the same manner as in Example 1. The results are shown below.

|  | Response time | | |
| --- | --- | --- | --- |
|  | 10° C. | 25° C. | 40° C. |
| 18-A | 1360 μsec | 430 μsec | 147 μsec |
| 19-C | 1183 μsec | 384 μsec | 134 μsec |

As apparent from the above Example 19 and Comparative Example 19, the ferroelectric liquid crystal device containing the liquid crystal composition 19-B according to the present invention provided improved response speed and operation characteristic at a lower temperature and also provided a decreased temperature dependence of response speed.

EXAMPLE 20

A liquid crystal composition 20-B was prepared by mixing the following example compounds in the indicated proportions with the liquid crystal composition 18-A prepared in Example 18.

vice, a monodomain with a good and uniform alignment characteristic was observed. The results of the measurement are shown below.

|  | 10° C. | 25° C. | 40° C. |
| --- | --- | --- | --- |
| Response time | 719 μsec | 249 μsec | 91 μsec |

Further, a contrast of 14 was attained at 25° C. during the driving, and a clear switching function was observed. The bistability after termination of the voltage application was also good.

COMPARATIVE EXAMPLE 20

A liquid crystal composition 20-C was prepared by adding only Example compounds Nos. 4-115, 4-147, 3-42 and 3-50 and without adding Example compound No. 2-6 to the composition 18-A.

Ferroelectric liquid crystal devices were prepared by using the compositions 20-C and 18-A, respectively, instead of the composition 1-B, and subjected to measurement of optical response time, otherwise in the same manner as in Example 1. The results are shown below.

|  | Response time | | |
| --- | --- | --- | --- |
|  | 10° C. | 25° C. | 40° C. |
| 18-A | 1360 μsec | 430 μsec | 147 μsec |
| 20-C | 1007 μsec | 339 μsec | 118 μsec |

As apparent from the above Example 20 and Comparative Example 20, the ferroelectric liquid crystal device containing the liquid crystal composition 20-B

| Ex. Comp. No. | Structural formula | wt. parts |
| --- | --- | --- |
| 4-115 | 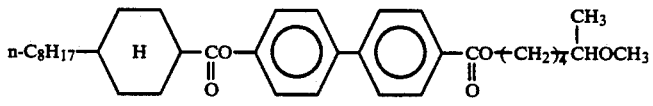 | 6 |
| 4-147 | 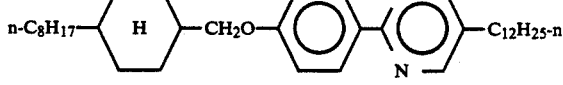 | 4 |
| 2-6 | 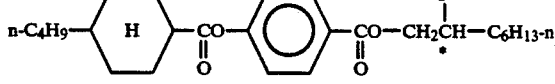 | 9 |
| 3-42 | 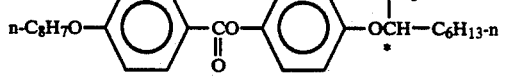 | 4 |
| 3-50 | 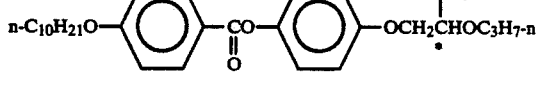 | 3 |
| Composition 18-A | | 74 |

A ferroelectric liquid crystal device was prepared in the same manner as in Example 1 except that the above liquid crystal composition 20-B was used, and the device was subjected to measurement of driving voltage margin and observation of switching states. In the deaccording to the present invention provided improved response speed and operation characteristic at a lower temperature and also provided a decreased temperature dependence of response speed.

EXAMPLE 21

A liquid crystal composition 21-A was prepared by mixing the following compounds in respectively indicated proportions.

| Ex. Compound No. | Structural formula | Wt. parts |
|---|---|---|
| 57 | 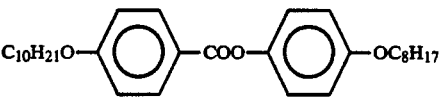 $C_{10}H_{21}O$—⟨⟩—COO—⟨⟩—$OC_8H_{17}$ | 6 |
| 58 | 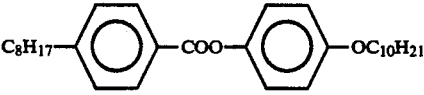 $C_8H_{17}$—⟨⟩—COO—⟨⟩—$OC_{10}H_{21}$ | 8 |
| 59 | 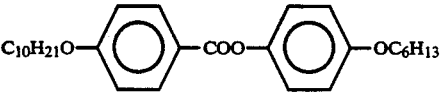 $C_{10}H_{21}O$—⟨⟩—COO—⟨⟩—$OC_6H_{13}$ | 9 |
| 60 | 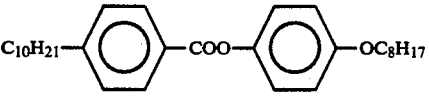 $C_{10}H_{21}$—⟨⟩—COO—⟨⟩—$OC_8H_{17}$ | 12 |
| 8 | 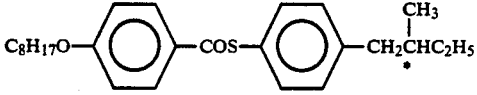 $C_8H_{17}O$—⟨⟩—COS—⟨⟩—$CH_2\overset{*}{C}H(CH_3)C_2H_5$ | 3 |
| 9 | 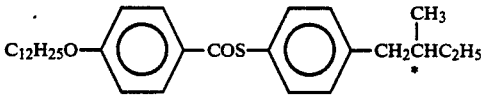 $C_{12}H_{25}O$—⟨⟩—COS—⟨⟩—$CH_2\overset{*}{C}H(CH_3)C_2H_5$ | 3 |
| 12 | 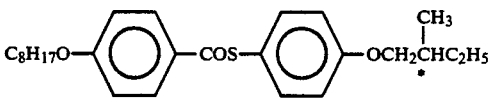 $C_8H_{17}O$—⟨⟩—COS—⟨⟩—$OCH_2\overset{*}{C}H(CH_3)C_2H_5$ | 3 |
| 13 | 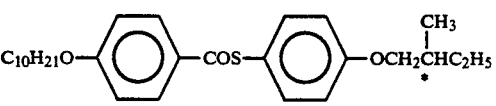 $C_{10}H_{21}O$—⟨⟩—COS—⟨⟩—$OCH_2\overset{*}{C}H(CH_3)C_2H_5$ | 3 |
| 16 | 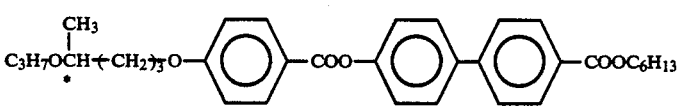 $C_3H_7O\overset{*}{C}H(CH_3)(CH_2)_3O$—⟨⟩—COO—⟨⟩—⟨⟩—$COOC_6H_{13}$ | 15 |
| 69 | 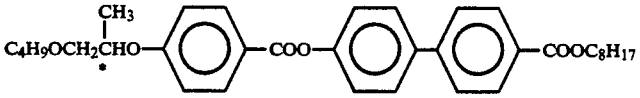 $C_4H_9OCH_2\overset{*}{C}H(CH_3)O$—⟨⟩—COO—⟨⟩—⟨⟩—$COOC_8H_{17}$ | 15 |
| 71 | 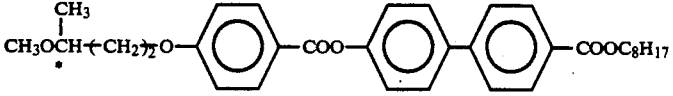 $CH_3O\overset{*}{C}H(CH_3)(CH_2)_2O$—⟨⟩—COO—⟨⟩—⟨⟩—$COOC_8H_{17}$ | 8 |
| 55 | 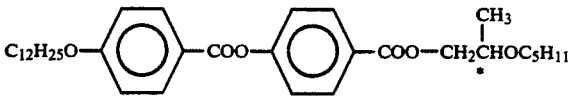 $C_{12}H_{25}O$—⟨⟩—COO—⟨⟩—COO—$CH_2\overset{*}{C}H(CH_3)OC_5H_{11}$ | 9 |

-continued

| Ex. Compound No. | Structural formula | Wt. parts |
|---|---|---|
| 75 | $C_{12}H_{25}O$—⟨phenyl⟩—COO—⟨phenyl⟩—COO—$(CH_2)_3$—$\overset{*}{C}H(CH_3)$—$OC_5H_{11}$ | 6 |

A liquid crystal composition 21-B was prepared by mixing the following example compounds in the respectively indicated proportions with the above prepared composition 21-A.

| Ex. Comp. No. | Structural formula | wt. parts |
|---|---|---|
| 4-5 | $n\text{-}C_3H_7$—⟨pyrimidine⟩—⟨phenyl⟩—⟨phenyl⟩—$OC_{11}H_{23}\text{-}n$ | 3 |
| 4-73 | $n\text{-}C_3H_7$—⟨cyclohexyl-H⟩—$\underset{O}{\overset{\|}{C}}$O—⟨phenyl⟩—⟨pyrimidine⟩—$C_{11}H_{23}\text{-}n$ | 6 |
| 2-42 | $n\text{-}C_{10}H_{21}$—⟨pyrimidine⟩—⟨phenyl⟩—$OCH_2\overset{*}{C}H(F)$—$C_8H_{17}\text{-}n$ | 7 |
| 3-23 | $n\text{-}C_{12}H_{25}O$—⟨phenyl⟩—$\underset{O}{\overset{\|}{C}}$O—⟨phenyl⟩—$O(CH_2)_2\overset{*}{C}H(CH_3)CHC_2H_5$ | 7 |
| Composition 21-A | | 77 |

A ferroelectric liquid crystal device 21-B was prepared in the same manner as in Example 1 except that the liquid crystal composition 21-B was used instead of the composition 1-B. The device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 743 μsec | 264 μsec | 102 μsec |

Further, a contrast of 12 was attained at 25° C. during the driving, and a clear switching function was observed.

COMPARATIVE EXAMPLE 21

A liquid crystal composition 21-C was prepared by adding only Example compounds Nos. 2-42 and 3-23 and without adding Example compound No. 4-5 or 4-73 to the composition 21-A; a liquid crystal composition 21-D was prepared by adding only Example compounds Nos. 4-5, 4-73 and 3-23 and without adding Example compound No. 2-42 to the composition 21-A; and a liquid crystal composition 21-E was prepared by adding only Example compounds Nos. 4-5, 4-73 and 2-42 and without adding Example compound No. 3-23 to the composition 21-A.

Ferroelectric liquid crystal devices were prepared by using the compositions 21-C, 21-D, 21-E and 21-A, respectively, instead of the composition 1-B, and subjected to measurement of optical response time, otherwise in the same manner as in Example 1. The results are shown below.

| | Response time (μsec) | | |
|---|---|---|---|
| | 10° C. | 25° C. | 40° C. |
| 21-A | 1155 μsec | 362 μsec | 133 μsec |
| 21-C | 820 μsec | 284 μsec | 104 μsec |
| 21-D | 1004 μsec | 326 μsec | 115 μsec |
| 21-E | 801 μsec | 283 μsec | 108 μsec |

As apparent from the above Example 21 and Comparative Example 21, the ferroelectric liquid crystal device containing the liquid crystal composition 21-B according to the present invention provided improved response speed and operation characteristic at a lower temperature and also provided a decreased temperature dependence of response speed.

EXAMPLE 22

A liquid crystal composition 22-B was prepared by mixing the following example compounds in the indicated proportions with the liquid crystal composition 21-A prepared in Example 21.

| Ex. Comp. No. | Structural formula | wt. parts |
| --- | --- | --- |
| 4-69 | n-$C_3H_7$—[H]—CO-O—[phenyl]—[pyrimidine N,N]—$C_{10}H_{21}$-n | 5 |
| 4-105 | n-$C_3H_7$—[H]—CO-O—[phenyl]—[phenyl]—O$C_8H_{17}$-n | 5 |
| 2-36 | n-$C_9H_{19}$—[pyrimidine N,N]—[phenyl]—OCH$_2$CH(F)*—$C_7H_{15}$-n | 7 |
| 2-72 | n-$C_7H_{15}$—[pyrimidine N,N]—[phenyl]—CO-O—CH$_2$CH(F)*—$C_5H_{11}$-n | 2 |
| 3-38 | n-$C_6H_{13}$O—[phenyl]—CO-O—[phenyl]—OCH$_2$CH(CH$_3$)*$C_2H_5$ | 6 |
| Composition 21-A | | 75 |

A ferroelectric liquid crystal device was prepared in the same manner as in Example 1 except that the above liquid crystal composition 22-B was used, and the device was subjected to measurement of optical response time and observation of switching states. In the device, a monodomain with a good and uniform alignment characteristic was observed. The results of the measurement are shown below.

|  | 10° C. | 25° C. | 40° C. |
| --- | --- | --- | --- |
| Response time | 827 μsec | 292 μsec | 112 μsec |

Further, a contrast of 13 was attained at 25° C. during the driving, and a clear switching function was observed. The bistability after termination of the voltage application was also good.

COMPARATIVE EXAMPLE 22

A liquid crystal composition 22-C was prepared by adding only Example compounds Nos. 2-36 and 2-72 and without adding Example compound No. 4-69, 4-105 or 3-38 to the composition 21-A.

Ferroelectric liquid crystal devices were prepared by using the compositions 22-C and 21-A, respectively, instead of the composition 1-B, and subjected to measurement of optical response time, otherwise in the same manner as in Example 1. The results are shown below.

|  | Response time (μsec) | | |
| --- | --- | --- | --- |
|  | 10° C. | 25° C. | 40° C. |
| 21-A | 1155 | 362 | 133 |
| 22-C | 905 | 303 | 110 |

As apparent from the above Example 22 and Comparative Example 22, the ferroelectric liquid crystal device containing the liquid crystal composition 22-B according to the present invention provided improved response speed and operation characteristic at a lower temperature and also provided a decreased temperature dependence of response speed.

EXAMPLE 23

A liquid crystal composition 23-B was prepared by mixing the following example compounds in the indicated proportions with the liquid crystal composition 21-A prepared in Example 21.

| Ex. Comp. No. | Structural formula | wt. parts |
| --- | --- | --- |
| 4-11 | n-$C_7H_{15}$—[pyrimidine N,N]—[phenyl]—[phenyl]—$C_6H_{13}$-n | 6 |
| 4-34 | n-$C_{10}H_{21}$—[phenyl]—[pyrimidine N,N]—[phenyl]—O$C_5H_{11}$-n | 4 |

-continued

| Ex. Comp. No. | Structural formula | wt. parts |
|---|---|---|
| 2-21 | n-C$_3$H$_7$—[H]—CO—O—[phenyl]—OCH$_2$CH(F)—C$_8$H$_{17}$-n | 8 |
| 2-2 | n-C$_3$H$_7$—[H]—CO—O—[phenyl]—CO—O—CH$_2$CH(F)—C$_8$H$_{17}$-n | 2 |
| 3-22 | n-C$_{10}$H$_{21}$O—[phenyl]—CO—O—[phenyl]—OCH$_2$CH(CH$_3$)CH$_2$C$_2$H$_5$ | 7 |
| Composition 21-A | | 73 |

A ferroelectric liquid crystal device was prepared in the same manner as in Example 1 except that the above liquid crystal composition 23-B was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 724 μsec | 260 μsec | 101 μsec |

Further, a contrast of 13 was attained at 25° C. during the driving, and a clear switching function was observed. The bistability after termination of the voltage application was also good.

COMPARATIVE EXAMPLE 23

A liquid crystal composition 23-C was prepared by adding only Example compounds Nos. 4-11 and 4-34 and without adding Example compound No. 2-21, 2-2 or 3-60 to the composition 21-A.

Ferroelectric liquid crystal devices were prepared by using the compositions 23-C and 21-A, respectively, instead of the composition 1-B, and subjected to measurement of optical response time, otherwise in the same manner as in Example 1. The results are shown below.

| | Response time | | |
|---|---|---|---|
| | 10° C. | 25° C. | 40° C. |
| 21-A | 1155 μsec | 362 μsec | 133 μsec |
| 23-C | 1004 μsec | 344 μsec | 127 μsec |

As apparent from the above Example 23 and Comparative Example 23, the ferroelectric liquid crystal device containing the liquid crystal composition 23-B according to the present invention provided improved response speed and operation characteristic at a lower temperature and also provided a decreased temperature dependence of response speed.

EXAMPLE 24

A liquid crystal composition 24-A was prepared by mixing the following compounds in respectively indicated proportions.

| Ex. Compound No. | Structural formula | Wt. parts |
|---|---|---|
| 26 | C$_8$H$_{17}$O—[pyrimidine(N,N)]—[phenyl]—O(CH$_2$)$_5$CH(CH$_3$)CH$_2$C$_2$H$_5$ | 4 |
| 27 | C$_{10}$H$_{21}$O—[phenyl]—[pyrimidine(N,N)]—COO(CH$_2$)$_5$CH(CH$_3$)CH$_2$C$_2$H$_5$ | 4 |
| 28 | C$_{12}$H$_{25}$O—[phenyl]—[pyrimidine(N,N)]—COO(CH$_2$)$_5$CH(CH$_3$)CH$_2$C$_2$H$_5$ | 6 |
| 29 | C$_{10}$H$_{21}$O—[pyrimidine(N,N)]—[phenyl]—O(CH$_2$)$_5$CH(CH$_3$)CH$_2$C$_2$H$_5$ | 6 |

| Ex. Compound No. | Structural formula | Wt. parts |
|---|---|---|
| 30 | 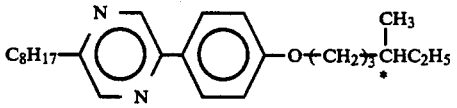 | 4 |
| 37 | 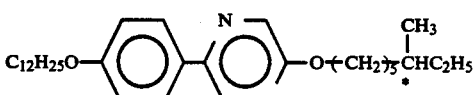 | 6 |
| 57 | 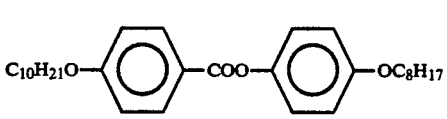 | 2 |
| 58 | 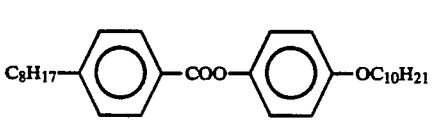 | 5 |
| 59 | 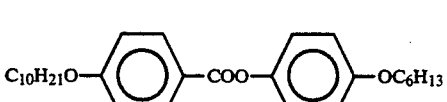 | 4 |
| 60 | 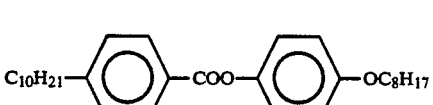 | 9 |
| 7 | 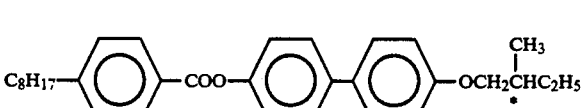 | 10 |
| 15 | 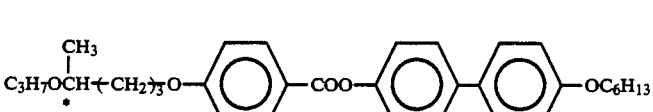 | 5 |
| 69 | 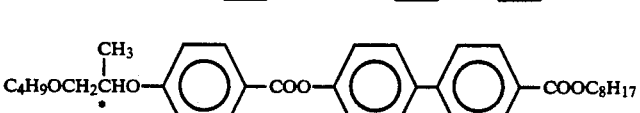 | 12 |
| 71 | 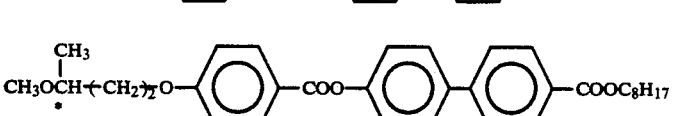 | 8 |
| 32 | 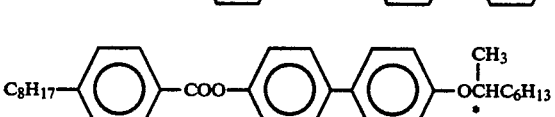 | 5 |
| 75 | 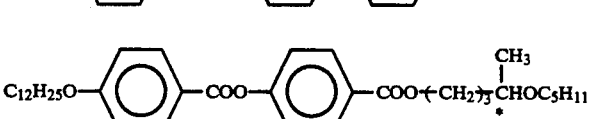 | 10 |
A liquid crystal composition 24-B was prepared by mixing the following example compounds in the respectively indicated proportions with the above prepared composition 24-A.

| Ex. Comp. No. | Structural formula | Wt. parts |
|---|---|---|
| 4-5 | n-C$_3$H$_7$–[pyrimidine]–[phenyl]–[phenyl]–OC$_{11}$H$_{23}$-n | 4 |
| 4-73 | n-C$_3$H$_7$–[H cyclohexyl]–COO–[phenyl]–[pyrimidine]–C$_{11}$H$_{23}$-n | 7 |
| 2-42 | n-C$_{10}$H$_{21}$–[pyrimidine]–[phenyl]–OCH$_2$CH(F)–C$_8$H$_{17}$-n * | 5 |
| 3-23 | n-C$_{12}$H$_{25}$O–[phenyl]–COO–[phenyl]–O–(CH$_2$)$_2$–CH(CH$_3$)–CH$_2$C$_2$H$_5$ * | 5 |
| Composition 24-A | | 79 |

A ferroelectric liquid crystal device 24-B was prepared in the same manner as in Example 1 except that the liquid crystal composition 24-B was used instead of the composition 1-B. The device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 542 μsec | 201 μsec | 83 μsec |

Further, a contrast of 14 was attained at 25° C. during the driving, and a clear switching function was observed. The bistability after termination of the voltage application application was also good.

COMPARATIVE EXAMPLE 24

A liquid crystal composition 24-C was prepared by adding only Example compounds Nos. 4-5, 4-73 and 3-23 and without adding Example compound No. 2-42 to the composition 24-A.

Ferroelectric liquid crystal devices were prepared by using the compositions 24-C and 24-A, respectively, instead of the composition 1-B, and subjected to measurement of optical response time, otherwise in the same manner as in Example 1. The results are shown below.

| | Response time (μsec) | | |
|---|---|---|---|
| | 10° C. | 25° C. | 40° C. |
| 24-A | 762 | 246 | 98 |
| 24-C | 663 | 235 | 91 |

As apparent from the above Example 24 and Comparative Example 24, the ferroelectric liquid crystal device containing the liquid crystal composition 24-B according to the present invention provided improved response speed and operation characteristic at a lower temperature and also provided a decreased temperature dependence of response speed.

EXAMPLE 25

A liquid crystal composition 25-B was prepared by mixing the following example compounds in the indicated proportions with the liquid crystal composition 24-A prepared in Example 24.

| Ex. Comp. No. | Structural formula | wt. parts |
|---|---|---|
| 4-69 | n-C$_3$H$_7$–[H cyclohexyl]–COO–[phenyl]–[pyrimidine]–C$_{10}$H$_{21}$-n | 6 |
| 4-105 | n-C$_3$H$_7$–[H cyclohexyl]–COO–[phenyl]–[phenyl]–OCO–C$_8$H$_{17}$-n | 3 |

| Ex. Comp. No. | Structural formula | wt. parts |
|---|---|---|
| 2-36 | n-$C_9H_{19}$—[pyrimidine]—[phenyl]—$OCH_2\overset{*}{C}H(F)$—$C_7H_{15}$-n | 6 |
| 2-72 | n-$C_7H_{15}$—[pyrimidine]—[phenyl]—$CO-O-CH_2\overset{*}{C}H(F)$—$C_5H_{11}$-n | 2 |
| 3-38 | n-$C_6H_{13}O$—[phenyl]—$CO-O$—[phenyl]—$OCH_2\overset{*}{C}H(CH_3)C_2H_5$ | 5 |
| Composition 24-A | | 78 |

A ferroelectric liquid crystal device was prepared in the same manner as in Example 1 except that the above liquid crystal composition 25-B was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time | 529 μsec | 196 μsec | 82 μsec |

Further, a contrast of 12 was stirred at 25° C. during the driving, and a clear switching function was observed. The bistability after termination of the voltage application was also good.

COMPARATIVE EXAMPLE 25

A liquid crystal composition 25-C was prepared by adding only Example compounds Nos. 2-36, 2-72, and 3-38 and without adding Example compound No. 4-69 or 4-105 to the composition 24-A.

Ferroelectric liquid crystal device were prepared by using the compositions 25-C and 24-A, respectively, instead of the composition 1-B, and subjected to measurement of optical response time, otherwise in the same manner as in Example 1. The results are shown below.

| | Response time (μsec) | | |
|---|---|---|---|
| | 10° C. | 25° C. | 40° C. |
| 24-A | 762 | 246 | 98 |
| 25-C | 563 | 202 | 81 |

As apparent from the above Example 25 and Comparative Example 25, the ferroelectric liquid crystal device containing the liquid crystal composition 25-B according to the present invention provided improved response speed and operation characteristic at a lower temperature and also provided a decreased temperature dependence of response speed.

EXAMPLE 26

A liquid crystal composition 26-B was prepared by mixing the following example compounds in the indicated proportions with the liquid crystal composition 24-A prepared in Example 24.

| Ex. Comp. No. | Structural formula | wt. parts |
|---|---|---|
| 4-82 | n-$C_5H_{11}$—[H]—$CO-O$—[phenyl]—[pyrimidine]—$C_{16}H_{33}$-n | 5 |
| 4-165 | n-$C_3H_7$—[H]—$CH_2O$—[phenyl]—[pyrimidine]—$C_6H_{13}$-n | 5 |
| 2-77 | n-$C_9H_{19}$—[pyrimidine]—[phenyl]—$CO-O-CH_2\overset{*}{C}H(F)$—$C_6H_{13}$-n | 2 |
| 2-12 | n-$C_4H_9$—[H]—$CO-O$—[phenyl]—$OCH_2\overset{*}{C}H(F)$—$C_8H_{17}$-n | 6 |

| Ex. Comp. No. | Structural formula | wt. parts |
|---|---|---|
| 3-29 | n-$C_6H_{13}$CO-○-CO-○-OCHC$_6$H$_{13}$-n with CH$_3$ group (ester linkages) | 6 |
| | Composition 24-A | 76 |

A ferroelectric liquid crystal device was prepared in the same manner as in Example 1 except that the above liquid crystal composition 26-B was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 423 μsec | 162 μsec | 66 μsec |

Further, a contrast of 13 was attained at 25° C. during the driving, and a clear switching function was observed. The bistability after termination of the voltage application was also good.

COMPARATIVE EXAMPLE 26

A liquid crystal composition 26-C was prepared by adding only Example compound No. 3-29 and without adding Example compound No. 4-82, 4-165, 2-77 or 2-12 to the composition 24-A.

Ferroelectric liquid crystal devices were prepared by using the compositions 26-C and 24-A, respectively, instead of the composition 1-B, and subjected to measurement of optical response time, otherwise in the same manner as in Example 1. The results are shown below.

| | Response time | | |
|---|---|---|---|
| | 10° C. | 25° C. | 40° C. |
| 24-A | 762 μsec | 246 μsec | 98 μsec |
| 26-C | 561 μsec | 199 μsec | 78 μsec |

As apparent from the above Example 26 and Comparative Example 26, the ferroelectric liquid crystal device containing the liquid crystal composition 26-B according to the present invention provided improved response speed and operation characteristic at a lower temperature and also provided a decreased temperature dependence of response speed.

EXAMPLES 27–33

Liquid crystal compositions 27-B to 33-B were prepared by replacing the example compounds and the liquid crystal compositions used in Examples 18, 21 and 24 with example compounds and liquid crystal compositions shown in the following Table 2. Ferroelectric liquid crystal devices were prepared by respectively using these compositions instead of the composition 1-B, and subjected to measurement of optical response time and observation of switching states. In the devices, a monodomain with a good and uniform alignment characteristic was observed. The results of the measurement are shown in the following Table 2.

TABLE 2

| Ex. No (Comp. No.) | Example compound No. or liquid crystal composition No. (weight parts) | | | | | | | Response time (μsec) | | |
|---|---|---|---|---|---|---|---|---|---|---|
| | | | | | | | | 10° C. | 25° C. | 40° C. |
| 27 (27-B) | 4-19 (5) | 4-161 (4) | 4-179 (4) | 2-17 (7) | 3-51 (4) | 3-2 (3) | 18-A (73) | 796 | 275 | 104 |
| 28 (28-B) | 4-3 (4) | 4-117 (5) | 2-40 (2) | 2-3 (6) | 3-9 (5) | | 18-A (78) | 715 | 247 | 91 |
| 29 (29-B) | 4-27 (3) | 4-14 (5) | 4-106 (4) | 2-79 (8) | 3-39 (4) | 3-58 (4) | 21-A (72) | 773 | 273 | 108 |
| 30 (30-B) | 4-32 (6) | 4-146 (4) | 2-61 (5) | 2-81 (2) | 3-69 (6) | 3-32 (4) | 21-A (73) | 885 | 300 | 116 |
| 31 (31-B) | 4-12 (6) | 4-70 (4) | 4-166 (4) | 2-31 (4) | 2-11 (5) | 3-21 (6) | 21-A (71) | 645 | 238 | 96 |
| 32 (32-B) | 4-77 (6) | 4-122 (3) | 4-158 (4) | 2-66 (8) | 3-28 (4) | | 24-A (75) | 432 | 165 | 69 |
| 33 (33-B) | 4-28 (8) | 4-149 (5) | 2-13 (8) | 3-49 (4) | 3-83 (4) | | 24-A (71) | 500 | 188 | 77 |

As is apparent from the results shown in the above Table 2, the ferroelectric liquid crystal devices containing the liquid crystal compositions 27-B to 33-B provided improved response speed and a decreased temperature dependence of the response speed.

EXAMPLE 34

A liquid crystal composition 34-B was prepared by mixing the following example compound in the indicated proportion with the liquid crystal composition 1-B prepared in Example 1.

| Ex. Comp. No. | Structural formula | wt. parts |
|---|---|---|
| 5-10 | n-$C_5H_{11}$—⟨H⟩—CO—⟨CN, CN⟩—$OC_6H_{13}$-n (O) | 10 |
| | Composition 1-B | 90 |

A ferroelectric liquid crystal device was prepared in the same manner as in Example 1 except that the above liquid crystal composition was used, and the device was subjected to measurement of optical response time in the same manner as in Example 1 to obtain the following results.

| | Response time | |
|---|---|---|
| 10° C. | 25° C. | 40° C. |
| 1211 μsec | 407 μsec | 146 μsec |

Then, the tilt angle of the above device was measured under right-angle cross nicols at 25° C. to provide 7.3 degrees. Further, the tilt angle of the device was again measured while being subjected to application of rectangular waveforms of ±8 V and a frequency of 60 KHz and found to be 13.3 degrees. The transmittance measured at that time was 12.8%, and a contrast of 53:1 was attained.

COMPARATIVE EXAMPLE 34

A liquid crystal composition 34-C was prepared in the same manner as in Example 34 except that the liquid crystal composition 1-A prepared in Example 1 was used instead of the composition 1-B to be mixed with the example compound No. 5-10 in the same proportions.

Ferroelectric liquid crystal devices were prepared by using the compositions 34-C, 1-A and 1-B respectively and subjected to measurement of optical response time, otherwise in the same manner as in Example 1. Further, the tilt angles of these devices were measured in the same manner as in Example 34. The results are shown below.

| | Response time | | |
|---|---|---|---|
| | 10° C. | 25° C. | 40° C. |
| 1-A | 1410 μsec | 435 μsec | 155 μsec |
| 1-B | 964 μsec | 338 μsec | 127 μsec |
| 34-C | 1830 μsec | 550 μsec | 178 μsec |

| | Tilt angle (25° C.) | |
|---|---|---|
| Comp. | Initial (no electric field) | Under AC appln. (60 KHz, ±8 V, rectangular) |
| 1-A | 7.6 degrees | 8.0 degrees |
| 1-B | 7.5 degrees | 7.7 degrees |
| 34-C | 7.5 degrees | 13.6 degrees |

As apparent from Example 34 and Comparative Example 34, the liquid crystal composition 34-B obtained by mixing a mesomorphic compound having a negative dielectric anisotropy (example compound No. 5-10) with the liquid crystal composition 1-B according to the present invention provided an improved response characteristic and also provided a remarkably improved display characteristic when used in a display method utilizing AC application (or AC stabilization).

EXAMPLE 35

A liquid crystal composition 35-B was prepared by mixing the following example compounds in the respectively indicated proportions with the liquid crystal composition 1-B prepared in Example 1.

| Ex. Comp. No. | Structural formula | wt. parts |
|---|---|---|
| 5-90 | n-$C_{10}H_{21}$—⟨N—N, S⟩—⟨⟩—$OC_{12}H_{25}$ | 5 |
| 5-12 | n-$C_8H_{17}$—⟨H⟩—CO—⟨CN, CN⟩—$OC_8H_{17}$-n (O) | 5 |
| 5-122 | n-$C_8H_{17}$—⟨H⟩—⟨H⟩(CN)—$C_8H_{17}$-n | 2 |
| 5-70 | n-$C_6H_{13}$—⟨⟩(N—N)—⟨⟩—$OC_5H_{11}$-n | 3 |

| Ex. Comp. No. | Structural formula | wt. parts |
|---|---|---|
| 5-107 | n-$C_{10}H_{21}$—[N=N/S thiadiazole]—[phenyl]—OC(=O)—[H cyclohexyl]—$C_3H_7$-n | 3 |
| 5-111 | n-$C_{12}H_{25}$—[N=N/S thiadiazole]—[phenyl]—$OCH_2$—[H cyclohexyl]—$C_5H_{11}$-n | 1 |
| 5-167 | n-$C_9H_{19}O$—[phenyl]—CH=C(CN)—[phenyl]—$C_7H_{15}$ | 1 |
| Composition 1-B | | 80 |

A ferroelectric liquid crystal device was prepared in the same manner as in Example 1 except that the above liquid crystal composition was used, and the device was subjected to measurement of optical response time in the same manner as in Example 1 to obtain the following results.

| | 10° C. | 25° C. | 40° C. |
|---|---|---|---|
| Response time | 1100 μsec | 395 μsec | 140 μsec |

Then, the tilt angle of the above device was measured under right-angle cross nicols at 25° C. to provide 8.6 degrees. Further, the tilt angle of the device was again measured while being subjected to application of rectangular waveforms of ±8 V and a frequency of 60 KHz and found to be 12.7 degrees. The transmittance measured at that time was 12.8%, and a contrast of 53:1 was attained.

COMPARATIVE EXAMPLE 35

A liquid crystal composition 35-C was prepared in the same manner as in Example 35 except that the liquid crystal composition 1-A prepared in Example 1 was used instead of the composition 1-B to be mixed with the other example compounds in the same proportions.

Ferroelectric liquid crystal devices were prepared by using the compositions 35-C, 1-A and 1-B respectively and subjected to measurement of driving voltage margin, otherwise in the same manner as in Example 1. Further, the tilt angles of these devices were measured in the same manner as in Example 35. The results are shown below.

| | Response time | | |
|---|---|---|---|
| | 10° C. | 25° C. | 40° C. |

-continued

| | | | |
|---|---|---|---|
| 1-A | 1410 μsec | 435 μsec | 155 μsec |
| 1-B | 964 μsec | 338 μsec | 127 μsec |
| 35-C | 1805 μsec | 538 μsec | 190 μsec |

| | Tilt angle (25° C.) | |
|---|---|---|
| Comp. | Initial (no electric field) | Under AC appln. (60 KHz, ±8 V, rectangular) |
| 1-A | 7.6 degrees | 8.0 degrees |
| 1-B | 7.5 degrees | 7.7 degrees |
| 35-C | 8.0 degrees | 12.9 degrees |

As apparent from Example 35 and Comparative Example 35, the liquid crystal composition 35-B obtained by mixing mesomorphic compounds having a negative dielectric anisotropy with the liquid crystal composition 1-B according to the present invention provided an improved responsive characteristic and also provided a remarkably improved display characteristic when used in a display method utilizing AC application (or AC stabilization).

EXAMPLE 36

A liquid crystal composition 36-B was prepared by mixing the following example compound in the indicated proportion with the liquid crystal composition 18-B prepared in Example 18.

| Ex. Comp. No. | Structural formula | wt. parts |
|---|---|---|
| 5-10 | n-$C_5H_{11}$—[H cyclohexyl]—CO(=O)—[phenyl with CN, CN]—$OC_6H_{13}$-n | 10 |
| Composition 18-B | | 90 |

A ferroelectric liquid crystal device was prepared in the same manner as in Example 1 except that the above liquid crystal composition was used, and the device was subjected to measurement of optical response time in the same manner as in Example 1 to obtain the following results.

| Response time | | |
|---|---|---|
| 10° C. | 25° C. | 40° C. |
| 1000 μsec | 330 μsec | 122 μsec |

Then, the tilt angle of the above device was measured under right-angle cross nicols at 25° C. to provide 7.1 degrees. Further, the tilt angle of the device was again measured while being subjected to application of rectangular waveforms of ±8 V and a frequency of 60 KHz and found to be 13.0 degrees. The transmittance measured at that time was 12.3%, and a contrast of 50:1 was attained.

COMPARATIVE EXAMPLE 36

A liquid crystal composition 36-C was prepared in the same manner as in Example 36 except that the liquid crystal composition 18-A prepared in Example 18 was used instead of the composition 18-B to be mixed with the example compound No. 5-10 in the same proportions.

Ferroelectric liquid crystal devices were prepared by using the compositions 36-C, 18-A and 18-B respectively and subjected to measurement of optical response time, otherwise in the same manner as in Example 1. Further, the tilt angles of these devices were measured in the same manner as in Example 36. The results are shown below.

| | Response time | | |
|---|---|---|---|
| | 10° C. | 25° C. | 40° C. |
| 18-A | 1360 μsec | 430 μsec | 147 μsec |
| 18-B | 825 μsec | 284 μsec | 107 μsec |
| 36-C | 1785 μsec | 530 μsec | 170 μsec |

| | Tilt angle (25° C.) | |
|---|---|---|
| Comp. | Initial (no electric field) | Under AC appln. (60 KHz, ±8 V, rectangular) |
| 18-A | 7.3 degrees | 7.5 degrees |
| 18-B | 7.2 degrees | 7.3 degrees |
| 36-C | 7.0 degrees | 13.0 degrees |

As apparent from Example 36 and Comparative Example 36, the liquid crystal composition 36-B obtained by mixing a mesomorphic compound having a negative dielectric anisotropy (example compound No. 5-10) with the liquid crystal composition 1-B according to the present invention provided an improved response characteristic and also provided a remarkably improved display characteristic when used in a display method utilizing AC application (or AC stabilization).

EXAMPLE 37

A liquid crystal composition 37-B was prepared by mixing the following example compounds in the respectively indicated proportions with the liquid crystal composition 18-B prepared in Example 18.

| Ex. Comp. No. | Structural formula | wt. parts |
|---|---|---|
| 5-90 | 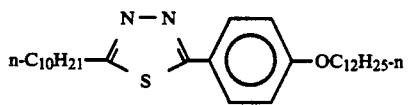 | 5 |
| 5-12 | 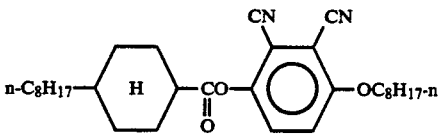 | 5 |
| 5-122 | 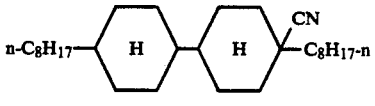 | 2 |
| 5-70 | 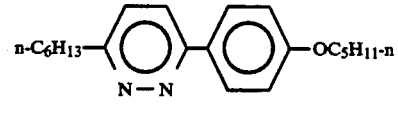 | 3 |
| 5-107 | 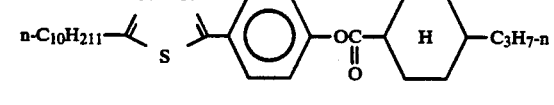 | 3 |
| 5-111 | 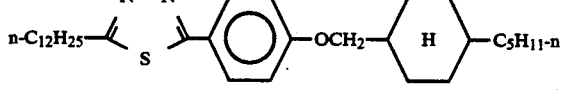 | 1 |
| 5-167 | 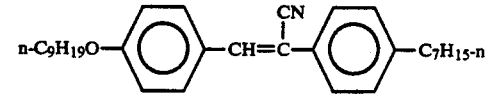 | 1 |

| Ex. Comp. No. | Structural formula | wt. parts |
|---|---|---|
| | Composition 18-B | 80 |

A ferroelectric liquid crystal device was prepared in the same manner as in Example 1 except that the above liquid crystal composition was used, and the device was subjected to measurement of optical response time in the same manner as in Example 1 to obtain the following results.

| | 10° C. | 25° C. | 40° C. |
|---|---|---|---|
| Response time | 930 μsec | 320 μsec | 118 μsec |

Then, the tilt angle of the above device was measured under right-angle cross nicols at 25° C. to provide 8.0 degrees. Further, the tilt angle of the device was again measured while being subjected to application of rectangular waveforms of ±8 V and a frequency of 60 KHz and found to be 12.1 degrees. The transmittance measured at that time was 11.9%, and a contrast of 47:1 was attained.

COMPARATIVE EXAMPLE 37

A liquid crystal composition 37-C was prepared in the same manner as in Example 37 except that the liquid crystal composition 18-A prepared in Example 18 was used instead of the composition 18-B to be mixed with the other example compounds in the same proportions.

Ferroelectric liquid crystal devices were prepared by using the compositions 37-C, 18-A and 18-B respectively and subjected to measurement of driving voltage margin, otherwise in the same manner as in Example 1. Further, the tilt angles of these devices were measured in the same manner as in Example 37. The results are shown below.

| | Response time | | |
|---|---|---|---|
| | 10° C. | 25° C. | 40° C. |
| 18-A | 1360 μsec | 430 μsec | 147 μsec |
| 18-B | 825 μsec | 284 μsec | 107 μsec |
| 37-C | 1652 μsec | 503 μsec | 165 μsec |

| | Tilt angle (25° C.) | |
|---|---|---|
| Comp. | Initial (no electric field) | Under AC appln. (60 KHz, ±8 V, rectangular) |
| 18-A | 7.3 degrees | 7.5 degrees |
| 18-B | 7.2 degrees | 7.3 degrees |
| 37-C | 7.0 degrees | 13.0 degrees |

As apparent from Example 37 and Comparative Example 37, the liquid crystal composition 37-B obtained by mixing mesomorphic compounds having a negative dielectric anisotropy with the liquid crystal composition 18-B according to the present invention provided an improved responsive characteristic and also provided a remarkably improved display characteristic when used in a display method utilizing AC application (or AC stabilization).

For example, the dielectric anisotropy $\Delta\epsilon$ of a mesomorphic compound or a liquid crystal composition referred to herein may be measured in the following manner.

A 5 micron-thick homogeneous alignment cell having an electrode of 0.7 cm² in area and a homogeneous alignment layer (rubbed polyimide) on both substrates, and a 5 micron-thick homeotropic alignment cell having an electrode of 0.7 cm² in area and a homeotropic alignment layer (aligning agent: "ODS-E" available from Chisso K. K.) on both substrates, are provided. The respective cells are filled with a sample liquid crystal material (compound or composition) to prepare liquid crystal devices. The capacitances of the liquid crystal layers are measured by applying a sine wave with a frequency of 100 KHz and amplitudes of ±0.5 V to the respective devices at a prescribed temperature set for the liquid crystal material, and the dielectric constants $\epsilon_{11}$ and $\epsilon_\perp$ are obtained from the measured capacitance values of the respective devices, whereby the dielectric anisotropy $\Delta\epsilon$ is calculated by the equation of $\Delta\epsilon = \epsilon_{11} - \epsilon_\perp$.

EXAMPLE 38

A blank cell was prepared in the same manner as in Example 1 except for omitting the SiO₂ layer to form an alignment control layer composed of the polyimide resin layer alone on each electrode plate. Five ferroelectric liquid crystal devices were prepared by filling such a blank cell with liquid crystal compositions 18-B, 18-A, 18-C, 18-D and 18-E, respectively, prepared in Example 18 and Comparative Example 18. These liquid crystal devices were subjected to measurement of optical response time in the same manner as in Example 1. The results are shown below.

| | Response time (μsec) | | |
|---|---|---|---|
| | 10° C. | 25° C. | 40° C. |
| 18-B | 820 | 264 | 92 |
| 18-A | 1340 | 415 | 138 |
| 18-C | 918 | 312 | 112 |
| 18-D | 1145 | 349 | 118 |
| 18-E | 863 | 279 | 104 |

As is apparent from the above Example 38, also in the case of a different device structure, the device containing the ferroelectric liquid crystal composition 18-B according to the present invention provided improved operation characteristic at a lower temperature and also a decreased temperature dependence of response speed.

As described hereinabove, the ferroelectric liquid crystal composition according to the present invention provides a liquid crystal device which shows a good switching characteristic, an improved operation characteristic and a decreased temperature dependence of response speed. Further, the liquid crystal composition according to the present invention further containing a mesomorphic compound having a negative dielectric anisotropy, provides a liquid crystal device which retains the above-mentioned characteristics and further shows a remarkably improved display characteristic when used in a driving method utilizing AC stabilization.

What is claimed is:

1. A ferroelectric chiral smectic liquid crystal composition, comprising:
   at least one compound represented by the following formula (II):

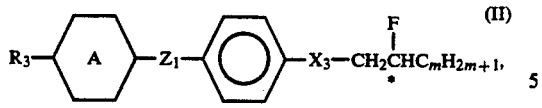 (II)

wherein R₃ denotes a linear or branched alkyl group having 1-18 carbon atoms wherein R₃ is optionally substituted with alkoxy group; X₃ denotes a single bond,

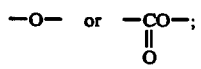

Z₁ denotes a single bond or

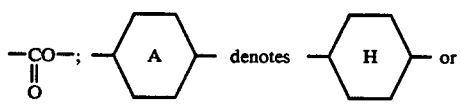; A denotes 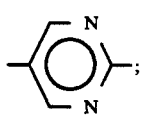;

and m is 1-12;
at least one compound represented by the following formula (III):

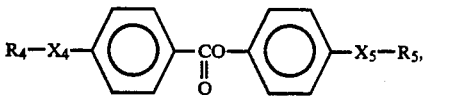 (III)

wherein R₄ and R₅ denote a linear or branched alkyl group having 1-18 carbon atoms, at least one of R₄ and R₅ being optically active; X₄ denotes a single bond,

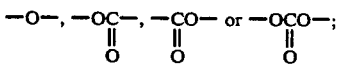

and X₅ denotes a single bond,

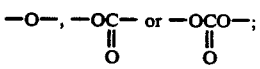

and
at least one compound represented by the following formula (I) or (IV):

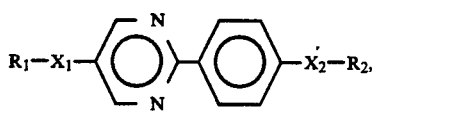 (I)

wherein R₁ and R₂ denote a linear or branched alkyl group having 1-18 carbon atoms; X₁ and X₂ denote a single bond,

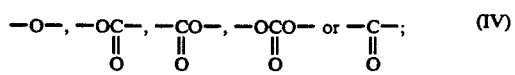 (IV)

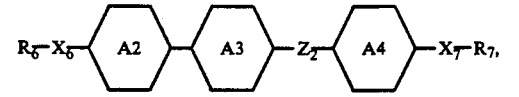

wherein R₆ and R₇ denote a linear or branched alkyl group having 1-18 carbon atoms wherein R₆ is optionally substituted with alkoxycarbonyl group or halogen; X₆ and X₇ denote a single bond,

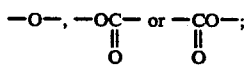

Z₂ denotes

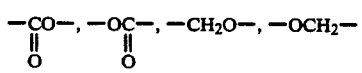

or a single bond;

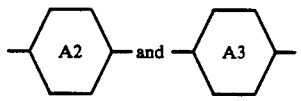

denote

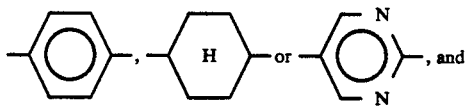, and

denotes

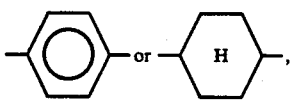, with proviso that at least one of

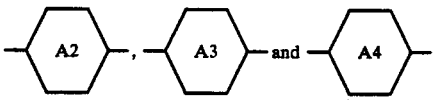

is

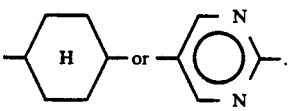.

2. A composition according to claim 1, which further comprises a mesomorphic compound having a negative dielectric anisotropy.

3. A composition according to claim 2, wherein said mesomorphic compound has a dielectric anisotropy Δε of below −2.

4. A composition according to claim 3, wherein said mesomorphic compound has a dielectric anisotropy Δε of below −5.

5. A composition according to claim 4, wherein said mesomorphic compound having a negative dielectric anisotropy has a dielectric anisotropy Δε of below −10.

6. A composition according to claim 2, wherein said mesomorphic compound is represented by any of the following Formulae (V-1) to (V-5);

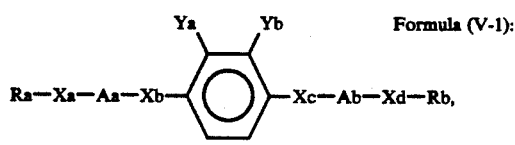

Formula (V-1):

wherein Ra and Rb denote a linear or branched alkyl group wherein Rb is optionally substituted with alkoxy group; Xa and Xd denote a single bond,

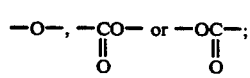

Xb and Xc denote a single bond,

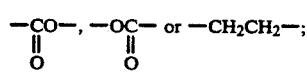

Aa and Ab denote a single bond,

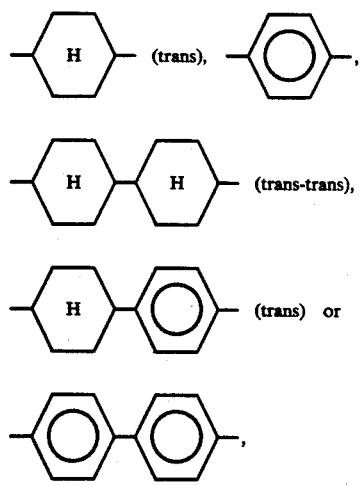

with proviso that when Aa and Ab are both single bonds, Xb and Xc are both single bonds, and Xa and Sd are both single bonds or —O—, or Xa is

and Xd is

and Ya and Yb are cyano group, halogen or hydrogen with proviso that Ya and Yb cannot be hydrogen simultaneously;

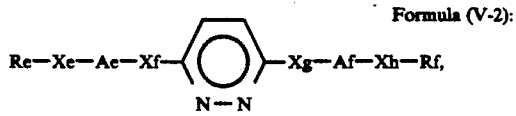

Formula (V-2):

wherein Re and Rf denote a linear or branched alkyl group; Xe and Hh are a single bond,

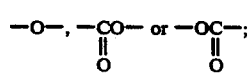

Xf and Xg are respectively

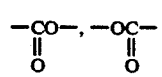

or a single bond; and Ae and Af are

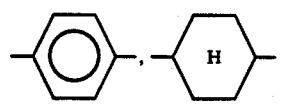

or a single bond with proviso that Ae and Af cannot be a single bond simultaneously;

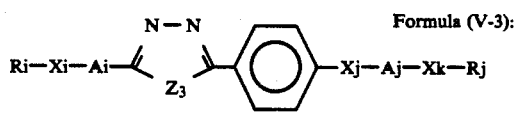

Formula (V-3):

wherein Ai is a single bond or

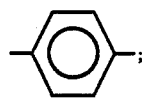

Aj is a single bond,

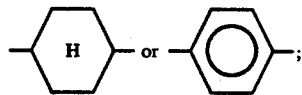

Ri and Rj are a linear or branched alkyl group wherein Ri is optionally substituted with Cl radical and Rj is optionally substituted with alkoxy group with proviso that Ri and Rj are linear alkyl groups when Aj is a single bond; $Z_3$ is —O— or —S—; Xi and Xk are a single bond,

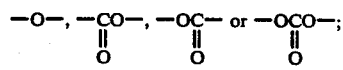

Xj is a singel bond,

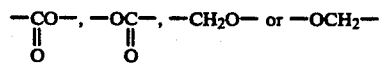

with proviso that Xi is a single bond when Ai is a single bond, Xj is not a single bond when Aj is

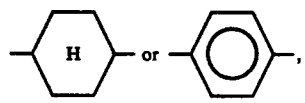

and Xk is a single bond when Aj is a single bond;

Formula (V-4):

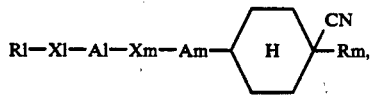

wherein Rl and Rm are a linear or branched alkyl group; Al and Am are a single bond,

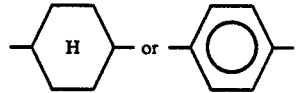

with proviso that Al and Am cannot be a single bond simultaneously; Xl is a single bond,

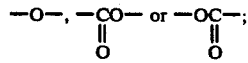

and Xm is a single bond,

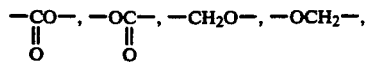

—CH$_2$CH$_2$— or —C≡C—;

Formula (V-5):

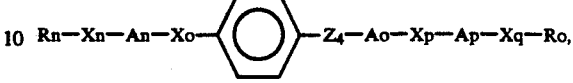

wherein Rn and Ro are a linear or branched alkyl group; Xn and Xq are a single bond,

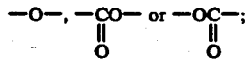

Xo and Xp are a single bond,

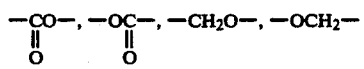

or —CH$_2$CH$_2$—; An and Ap are a single bond,

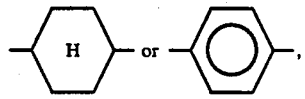

Ao is

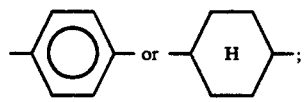

and Z$_4$ is

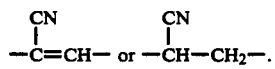

7. A liquid crystal device, comprising a pair of electrode plates and a ferroelectric liquid crystal composition according to any one of claims 1-6 disposed between the electrode plates.

* * * * *

UNITED STATES PATENT AND TRADEMARK OFFICE
CERTIFICATE OF CORRECTION

PATENT NO. : 5,292,453
DATED : March 8, 1994
INVENTOR(S) : KENJI SHINJO, ET AL.

It is certified that error appears in the above-identified patent and that said Letters Patent is hereby corrected as shown below:

IN [57] ABSTRACT

Page 2, Column 1, Line 13, "point and" should be deleted.
    Page 2, Column 1, Line 14, "non-selected" should be deleted.

COLUMN 1

Line 64, "lines are," should read --lines,-- and "is" should be deleted.
    Line 66, "selected" should read --selected point and non-selected--.

COLUMN 2

Line 22, "U.S. Pat. No. 4367924," should read --U.S. Pat. No. 4,367,924,--.

COLUMN 4

Line 22, "(I) $\Delta\epsilon \neq -5.5$, (II) $\Delta\epsilon \neq -3.0$," should read --(I) $\Delta\epsilon = -5.5$, (II) $\Delta\epsilon = -3.0$,
    Line 23, "(III) $\Delta\epsilon \neq -0$, (IV) $\Delta\epsilon \neq 1.0$." should read --(III) $\Delta\epsilon = -0$, (IV) $\Delta\epsilon = 1.0$.--.

COLUMN 6

Line 2, "$\Delta\epsilon(2 < |\Delta\epsilon 10)$" should read --$\Delta\epsilon(2 < |\Delta\epsilon| \leq 10)$--.
    Line 14, "$(2 < |\Delta\epsilon \leq 10)$," should read --$(2 < |\Delta\epsilon| \leq 10)$,--.

COLUMN 7

Line 47, "—O—," should be deleted.

UNITED STATES PATENT AND TRADEMARK OFFICE
CERTIFICATE OF CORRECTION

PATENT NO. : 5,292,453
DATED : March 8, 1994
INVENTOR(S) : KENJI SHINJO, ET AL.

It is certified that error appears in the above-identified patent and that said Letters Patent is hereby corrected as shown below:

COLUMN 8

Line 6, "bond" should read --bond;--.

COLUMN 10

Line 60, "group" should read --group.--.
  Line 66, "optically" should read --(optically--.

COLUMN 14

Line 7, "(IV-v)" should read --(IV-vi)--.

COLUMN 27

Formula (1-170),
  " 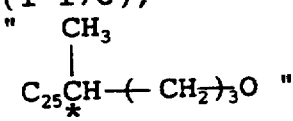 "    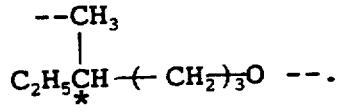 --.

COLUMN 40

Line 8, "900," should read --2900,-- and
          "1250 260," should read --1250, 1260,--.
  Line 21, "Iso," should read --Iso.--.

COLUMN 43

Formula (3-46), "$C_{19}H_{19}$" should read --$C_9H_{19}$--.

UNITED STATES PATENT AND TRADEMARK OFFICE
CERTIFICATE OF CORRECTION

PATENT NO. : 5,292,453
DATED : March 8, 1994
INVENTOR(S) : KENJI SHINJO, ET AL.

It is certified that error appears in the above-identified patent and that said Letters Patent is hereby corrected as shown below:

COLUMN 45

Formula (2-75), "(2-75)" should read --(3-75)--.

COLUMN 46

Line 29, "⟶" should read -- $\xrightarrow{KOH}$ --.

COLUMN 75

Line 28, "whereby" should read --yielding--.

COLUMN 121

Line 8, "1-100 wt. parts," should read --2-100 wt. parts,--.
Line 25, "formulas (II)(III)" should read
  --formulas (II), (III)--.

COLUMN 148

TABLE 1, under "Response time (μsec)",
  "178" should read --179--.

COLUMN 151

Line 15, "was voltage" should read --was observed. The bistability after termination of the voltage--.

COLUMN 163

Ex. Compound No. 32, "COO" should read --OCO--.

UNITED STATES PATENT AND TRADEMARK OFFICE
CERTIFICATE OF CORRECTION

PATENT NO. : 5,292,453
DATED : March 8, 1994
INVENTOR(S) : KENJI SHINJO, ET AL.

Page 4 of 5

It is certified that error appears in the above-identified patent and that said Letters Patent is hereby corrected as shown below:

COLUMN 165

Line 45, "application application" should read --application--.
Line 50, "3-23and" should read --3-23 and--.

COLUMN 167

Line 34, "stirred" should read --attained--.
Line 44, "device" should read --devices--.

COLUMN 170

TABLE 2, under "Response time (μsec)", "885" should read --855--.

COLUMN 176

Ex. Compound No. 5-107, "n-$C_{10}H_{211}$" should read --n-$C_{10}H_{21}$--.

COLUMN 181

Line 11, "having a negative dielectric" should be deleted.
Line 12, "anisotropy" should be deleted.(first occurrence).
Line 61, "and Sd" should read --and Xd--.

COLUMN 182

Line 17, "and Hh" should read --and Xh--.

UNITED STATES PATENT AND TRADEMARK OFFICE
CERTIFICATE OF CORRECTION

PATENT NO. : 5,292,453
DATED : March 8, 1994
INVENTOR(S) : KENJI SHINJO, ET AL.

It is certified that error appears in the above-identified patent and that said Letters Patent is hereby corrected as shown below:

COLUMN 183

Line 7, "singel" should read --single--.

Signed and Sealed this

Seventeenth Day of January, 1995

Attest:

BRUCE LEHMAN

Attesting Officer

Commissioner of Patents and Trademarks